US012644132B2

(12) United States Patent
Zolotukhin et al.

(10) Patent No.: US 12,644,132 B2
(45) Date of Patent: Jun. 2, 2026

(54) AAV3B VARIANTS THAT TARGET HEPATOCYTES AND EVADE THE HUMORAL IMMUNE RESPONSE

(71) Applicant: University of Florida Research Foundation, Incorporated, Gainesville, FL (US)

(72) Inventors: Sergei Zolotukhin, Gainesville, FL (US); Roland Wilfried Herzog, Gainesville, FL (US); Damien Marsic, Gainesville, FL (US); Moanaro Biswas, Fishers, IN (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 962 days.

(21) Appl. No.: 17/779,510

(22) PCT Filed: Nov. 24, 2020

(86) PCT No.: PCT/US2020/062113
§ 371 (c)(1),
(2) Date: May 24, 2022

(87) PCT Pub. No.: WO2021/108467
PCT Pub. Date: Jun. 3, 2021

(65) Prior Publication Data
US 2023/0340526 A1      Oct. 26, 2023

Related U.S. Application Data

(60) Provisional application No. 62/940,167, filed on Nov. 25, 2019.

(51) Int. Cl.
*C12N 15/86* (2006.01)
*C12N 15/10* (2006.01)

(52) U.S. Cl.
CPC ......... *C12N 15/86* (2013.01); *C12N 15/1058* (2013.01); *C12N 2750/14143* (2013.01)

(58) Field of Classification Search
CPC .................................................. C12N 15/86
See application file for complete search history.

(56) References Cited

U.S. PATENT DOCUMENTS

| | | | |
|---|---|---|---|
| 6,156,303 | A | 12/2000 | Russell et al. |
| 7,186,552 | B2 | 3/2007 | Wilson et al. |
| 7,220,577 | B2 | 5/2007 | Zolotukhin |
| 7,927,585 | B2 | 4/2011 | Snyder |
| 8,445,267 | B2 | 5/2013 | Zhong et al. |
| 9,157,098 | B2 | 10/2015 | Zhong et al. |
| 9,677,088 | B2 | 6/2017 | Nakai et al. |
| 9,725,485 | B2 | 8/2017 | Srivastava et al. |
| 9,775,918 | B2 | 10/2017 | Zhong et al. |
| 10,011,640 | B2 | 7/2018 | Srivastava et al. |
| 10,308,957 | B2 | 6/2019 | Boye et al. |
| 10,426,844 | B2 | 10/2019 | Agbandje-McKenna et al. |
| 10,648,000 | B2 | 5/2020 | Hauswirth et al. |
| 10,723,768 | B2 | 7/2020 | Zhong et al. |
| 10,793,606 | B2 | 10/2020 | Zolotukhin et al. |
| 10,815,279 | B2 | 10/2020 | Srivastava et al. |
| 12,188,037 | B2 | 1/2025 | Zolotukhin et al. |
| 2006/0188484 | A1 | 8/2006 | Rabinowitz et al. |
| 2007/0036760 | A1 | 2/2007 | Wilson et al. |
| 2008/0269149 | A1 | 10/2008 | Bowles et al. |
| 2009/0075357 | A1 | 3/2009 | Snyder |
| 2009/0197338 | A1 | 8/2009 | Vandenberghe et al. |
| 2010/0104561 | A1 | 4/2010 | Zhong et al. |
| 2013/0109742 | A1 | 5/2013 | Hewitt et al. |
| 2014/0341852 | A1 | 11/2014 | Srivastava et al. |
| 2016/0017005 | A1 | 1/2016 | Asokan et al. |

(Continued)

FOREIGN PATENT DOCUMENTS

| | | |
|---|---|---|
| EP | 1487501 B1 | 12/2012 |
| JP | 2008-523813 A | 7/2008 |

(Continued)

OTHER PUBLICATIONS

Wu, P., et al., 2000, Mutational analysis of the adeno-associated virus type 2 (AAV2) capsid gene and construction of AAV2 vectors with altered tropism, J. Virol. 74(18):8635-8647.*

DiPrimio, N., et al., 2008, Surface loop dynamics in adeno-associated virus capsid assembly, J. Virol. 82(11):5178-5189.*

International Search Report and Written Opinion for International Application No. PCT/US2016/058130 mailed Apr. 7, 2017.

International Preliminary Report on Patentability for International Application No. PCT/US2016/058130 mailed May 3, 2018.

Invitation to Pay Additional Fees for Application No. PCT/US2020/062114, mailed Mar. 8, 2021.

International Search Report and Written Opinion for Application No. PCT/US2020/062114, mailed Apr. 29, 2021.

(Continued)

*Primary Examiner* — Jeffrey S Parkin
(74) *Attorney, Agent, or Firm* — Wolf, Greenfield & Sacks, P.C.

(57) ABSTRACT

Disclosed herein are recombinant AAV variant (e.g., variant serotype 3B (AAV3B)) capsid proteins and variant capsid protein-containing viral particles with enhanced ability to transduce hepatic cells. Viral particles containing these capsid variants are capable of evading neutralization by the host humoral immune response. The recombinant AAV3B variant proteins and viral particles disclosed herein were identified from a variant AAV3B capsid library that was engineered by making substitutions in only the variable regions of the capsid. Some embodiments of the AAV3B capsid variants disclosed herein comprise the AAV3B-DE5 variant, which contains 24 mutations relative to wild-type. Compositions of these variant AAV particles are provided that are useful for transducing and delivering therapeutic transgenes to cells, such as liver cells, and thus treat diseases and disorders pertaining to these cells.

20 Claims, 27 Drawing Sheets
Specification includes a Sequence Listing.

(56) References Cited

U.S. PATENT DOCUMENTS

| | | | |
|---|---|---|---|
| 2016/0289275 A1 | 10/2016 | Chiorini et al. | |
| 2016/0369298 A1 | 12/2016 | Marsic et al. | |
| 2018/0066285 A1 | 3/2018 | Ojala et al. | |
| 2018/0193489 A1 | 7/2018 | Hobbs et al. | |
| 2018/0244727 A1 | 8/2018 | Zhong et al. | |
| 2018/0245098 A1 | 8/2018 | Yazicioglu et al. | |
| 2019/0048041 A1 | 2/2019 | Asokan et al. | |
| 2019/0127424 A1 | 5/2019 | Srivastava et al. | |
| 2019/0249195 A1 | 8/2019 | Marsic et al. | |
| 2020/0002386 A1 | 1/2020 | Zolotukhin et al. | |
| 2020/0181644 A1 | 6/2020 | Zolotukhin et al. | |
| 2021/0040156 A1 | 2/2021 | Zhong et al. | |
| 2021/0061863 A1 | 3/2021 | Zolotukhin et al. | |
| 2021/0253644 A1 | 8/2021 | Srivastava et al. | |
| 2023/0049066 A1 | 2/2023 | Zolotukhin et al. | |

FOREIGN PATENT DOCUMENTS

| | | | |
|---|---|---|---|
| WO | WO 2004/112727 A2 | 12/2004 | |
| WO | WO 2005/033321 A2 | 4/2005 | |
| WO | WO 2008/124724 A1 | 10/2008 | |
| WO | WO 2010/011404 A2 | 1/2010 | |
| WO | WO 2012/057363 A1 | 5/2012 | |
| WO | WO 2012/109570 A1 | 8/2012 | |
| WO | WO 2013/170078 A1 | 11/2013 | |
| WO | WO 2014/193716 A2 | 12/2014 | |
| WO | WO 2015/048534 A1 | 4/2015 | |
| WO | WO 2015/108610 A1 | 7/2015 | |
| WO | WO 2015/121501 A1 | 8/2015 | |
| WO | WO 2015/134643 A1 | 9/2015 | |
| WO | WO 2017/070476 A2 | 4/2017 | |
| WO | WO 2018/200419 A1 | 11/2018 | |

OTHER PUBLICATIONS

International Preliminary Report on Patentability for Application No. PCT/US2020/062114, mailed Jun. 9, 2022.

Invitation to Pay Additional Fees for Application No. PCT/US2020/062113, mailed Feb. 17, 2021.

International Search Report and Written Opinion for Application No. PCT/US2020/062113, mailed Apr. 21, 2021.

International Preliminary Report on Patentability for Application No. PCT/US2020/062113, mailed Jun. 9, 2022.

Appleyard et al., Pretreatment with the probiotic VSL#3 delays transition from inflammation to dysplasia in a rat model of colitis-associated cancer. Am J Physiol Gastrointest Liver Physiol. Dec. 2011;301(6):G1004-13. doi: 10.1152/ajpgi.00167.2011. Epub Sep. 8, 2011.

Aslanidi et al., High-efficiency transduction of human monocyte-derived dendritic cells by capsid-modified recombinant AAV2 vectors. Vaccine. Jun. 6, 2012;30(26):3908-17. doi: 10.1016/j.vaccine.2012.03.079. Epub Apr. 10, 2012.

Aslanidi et al., Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.

Bowles et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.

Boye et al., ID of Optimal Gene Delivery Vectors in Primate Retina for Treatment of Human Disorders: Labels Non-Human Primate Eyes with Fluorescent Proteins and/or Fluorescent Dyes, Creating Sortable Cell Populations, Allowing for Screening of Capsid and Promoter Libraries. Office of Technology Licensing, University of Florida. Feb. 11, 2017. Retrieved from the Internet: <http://technologylicensing.research.ufl.edu/technologies/16134.pdf> on Apr. 12, 2017. 4 pages.

Bozzetti et al., Metabolic Bone Disease in preterm newborn: an update on nutritional issues. Ital J Pediatr. Jul. 14, 2009;35(1):20. doi: 10.1186/1824-7288-35-20.

Chen, Adeno-associated virus vectors for human gene therapy. World Journal of Medical Genetics. Aug. 27, 2015;5(3):28-45.

Choudhury et al., Novel Methodology for Creating Macaque Retinas with Sortable Photoreceptors and Ganglion Cells. Front Neurosci. Dec. 1, 2016;10:551. eCollection 2016.

Galindo, Alkaline Phosphatase (ALP). Aug. 23, 2010. Retrieved on May 8, 2018. http://www2.isu.edu/~galisusa/alp_sop.html. 4 pages.

Gao et al., Clades of Adeno-associated viruses are widely disseminated in human tissues. J Virol. Jun. 2004;78(12):6381-8.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Genbank Submission; NIH/NCBI, Accession No. AAS99272.1. Gao et al., Jun. 24, 2004.

Grimm et al., E Pluribus Unum: 50 Years of Research, Millions of Viruses, and One Goal—Tailored Acceleration of AAV Evolution. Mol Ther. Dec. 2015;23(12):1819-31.

Guo et al., Protein tolerance to random amino acid change. PNAS. Jun. 22, 2004;101(25):9205-10.

Gurda et al., Capsid antibodies to different adeno-associated virus serotypes bind common regions. J Virol. Aug. 2013;87(16):9111-24. doi: 10.1128/JVI.00622-13. Epub Jun. 12, 2013.

Ito et al., Engineered adeno-associated virus 3 vector with reduced reactivity to serum antibodies. Sci Rep. Apr. 29, 2021;11(1):9322. doi: 10.1038/s41598-021-88614-9.

Klimczak, Molecular evolution of adeno-associated virus for improved retinal gene therapies. University of California, Berkeley. Jan. 1, 2010. Retrieved from the internet <https://digitalassets.lib.berkeley.edu/etd/ucb/text/Klimczak_berkeley_0028E_10444.pdf> 116 pages.

Koerber et al., DNA shuffling of adeno-associated virus yields functionally diverse viral progeny. Mol Ther. Oct. 2008;16(10):1703-9. doi: 10.1038/mt.2008.167. Epub Aug. 26, 2008.

Lan et al., IA-2, a transmembrane protein of the protein tyrosine phosphatase family, is a major autoantigen in insulin-dependent diabetes mellitus. Proc Natl Acad Sci U S A. Jun. 25, 1996;93(13):6367-70.

Lerch et al., The structure of adeno-associated virus serotype 3B (AAV-3B): insights into receptor binding and immune evasion. Virology. Jul. 20, 2010;403(1):26-36. doi: 10.1016/j.virol.2010.03.027. Epub May 4, 2010.

Lochrie et al., Mutations on the external surfaces of adeno-associated virus type 2 capsids that affect transduction and neutralization. J Virol. Jan. 2006;80(2):821-34.

Maersch et al., Optimization of stealth adeno-associated virus vectors by randomization of immunogenic epitopes. Virology. Feb. 5, 2010;397(1):167-75. doi: 10.1016/j.virol.2009.10.021. Epub Nov. 18, 2009.

Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.

Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.

Marsic et al., Vector design Tour de Force: integrating combinatorial and rational approaches to derive novel adeno-associated virus variants. Mol Ther. Nov. 2014;22(11):1900-9. doi: 10.1038/mt.2014.139. Epub Jul. 22, 2014.

Muramatsu et al., Nucleotide sequencing and generation of an infectious clone of adeno-associated virus 3. Virology. Jul. 1, 1996;221(1):208-17.

Opie et al., Identification of amino acid residues in the capsid proteins of adeno-associated virus type 2 that contribute to heparan sulfate proteoglycan binding. J Virol. Jun. 2003;77(12):6995-7006.

Ozawa, [Gene therapy using AAV]. Uirusu. Jun. 2007;57(1):47-55. Article in Japanese.

Pang et al., AAV-mediated cone rescue in a naturally occurring mouse model of CNGA3-achromatopsia. PLoS One. 2012;7(4):e35250. doi: 10.1371/journal.pone.0035250. Epub Apr. 11, 2012.

Perabo et al., Combinatorial engineering of a gene therapy vector: directed evolution of adeno-associated virus. J Gene Med. Feb. 2006;8(2):155-62.

Romero et al., Exploring protein fitness landscapes by directed evolution. Nat Rev Mol Cell Biol. Dec. 2009;10(12):866-76.

(56)         References Cited

OTHER PUBLICATIONS

Tseng et al., Mapping the AAV Capsid Host Antibody Response toward the Development of Second Generation Gene Delivery Vectors. Front Immunol. Jan. 30, 2014;5:9. doi: 10.3389/fimmu.2014.00009. eCollection 2014.

Wu et al., Mutational analysis of the adeno-associated virus type 2 (AAV2) capsid gene and construction of AAV2 vectors with altered tropism. J Virol. Sep. 2000;74(18):8635-47. doi: 10.1128/jvi.74.

Xie et al., The atomic structure of adeno-associated virus (AAV-2), a vector for human gene therapy. Proc Natl Acad Sci U S A. Aug. 6, 2002;99(16):10405-10. doi: 10.1073/pnas.162250899. Epub Jul. 22, 2002.

Zhong et al., Next generation of adeno-associated virus 2 vectors: point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008. Erratum in Proc Natl Acad Sci U S A. Aug. 5, 2008;105(31):11032.

Zinn et al., In Silico Reconstruction of the Viral Evolutionary Lineage Yields a Potent Gene Therapy Vector. Cell Rep. Aug. 11, 2015;12(6):1056-68. doi: 10.1016/j.celrep.2015.07.019. Epub Jul. 30, 2015.

Zolotukhin et al., Improved Adeno-associated Viral Gene Transfer to Murine Glioma. J Genet Syndr Gene Ther. Apr. 29, 2013;4(133):12815. doi: 10.4172/2157-7412.

U.S. Appl. No. 15/769,615, filed Apr. 19, 2018, Zolotukhin et al.

U.S. Appl. No. 17/779,505, filed May 24, 2022, Zolotukhin et al.

PCT/US2016/058130, Apr. 7, 2017, International Search Report and Written Opinion.

PCT/US2016/058130, May 3, 2018, International Preliminary Report on Patentability.

PCT/US2020/062114, Mar. 8, 2021, Invitation to Pay Additional Fees.

PCT/US2020/062114, Apr. 29, 2021, International Search Report and Written Opinion.

PCT/US2020/062114, Jun. 9, 2022, International Preliminary Report on Patentability.

PCT/US2020/062113, Feb. 17, 2021, Invitation to Pay Additional Fees.

PCT/US2020/062113, Apr. 21, 2021, International Search Report and Written Opinion.

PCT/US2020/062113, Jun. 9, 2022, International Preliminary Report on Patentability.

[No Author Listed], GenBank Submission, Accession No. AKU89603.1. capsid protein [Adeno-associated virus]. Aug. 7, 2015.

Colella et al., Emerging Issues in AAV-Mediated In Vivo Gene Therapy. Mol Ther Methods Clin Dev. Dec. 1, 2017;8:87-104. doi: 10.1016/j.omtm.2017.11.007.

Naso et al., Adeno-Associated Virus (AAV) as a Vector for Gene Therapy. BioDrugs. Aug. 2017;31(4):317-334. doi: 10.1007/s40259-017-0234-5.

* cited by examiner

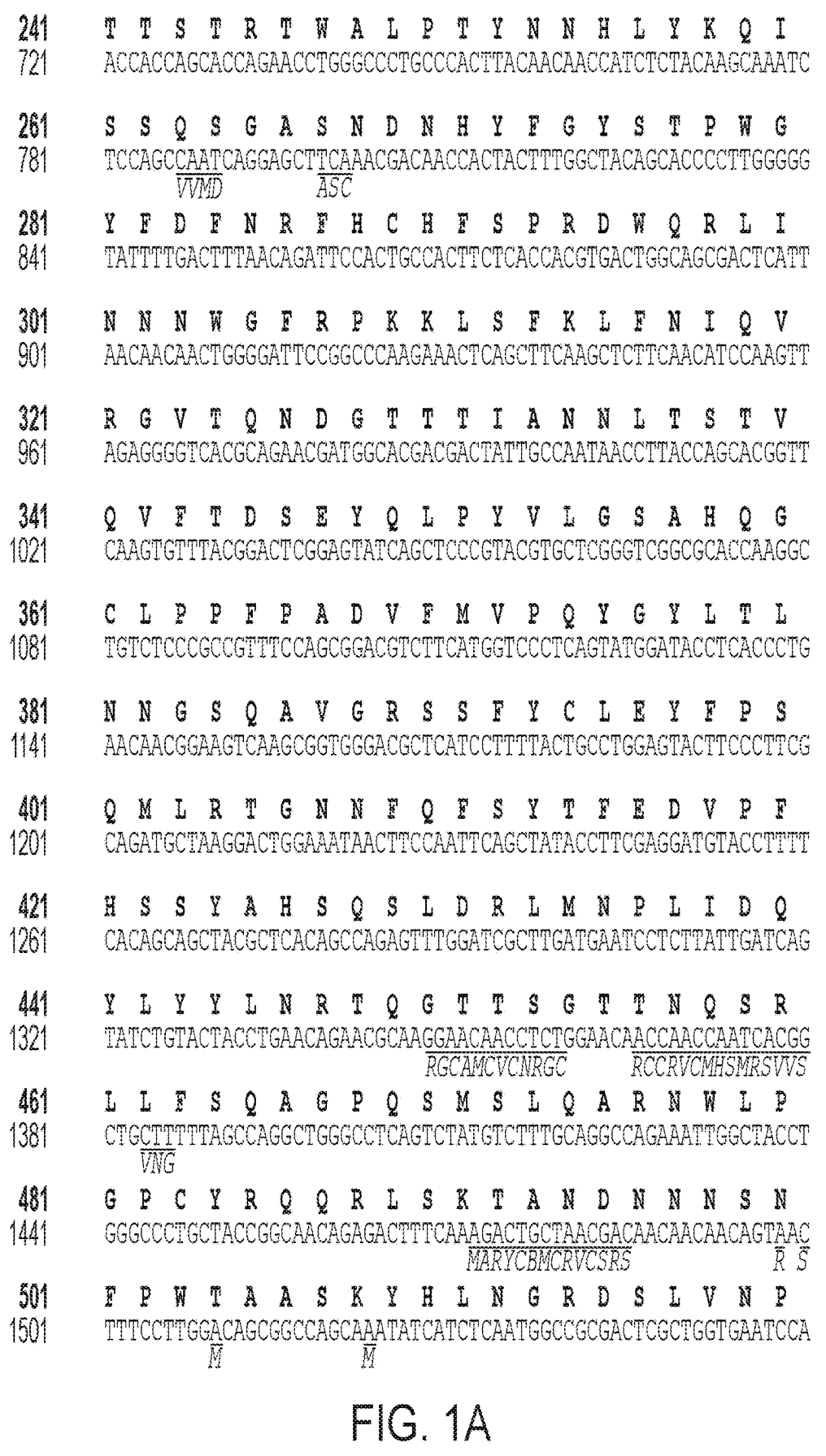

```
241   T  T  S  T  R  T  W  A  L  P  T  Y  N  N  H  L  Y  K  Q  I
721   ACCACCAGCACCAGAACCTGGGCCCTGCCCACTTACAACAACCATCTCTACAAGCAAATC

261   S  S  Q  S  G  A  S  N  D  N  H  Y  F  G  Y  S  T  P  W  G
781   TCCAGCCAATCAGGAGCTTCAAACGACAACCACTACTTTGGCTACAGCACCCCTTGGGGG
           VVMD              ASC

281   Y  F  D  F  N  R  F  H  C  H  F  S  P  R  D  W  Q  R  L  I
841   TATTTTGACTTTAACAGATTCCACTGCCACTTCTCACCACGTGACTGGCAGCGACTCATT

301   N  N  N  W  G  F  R  P  K  K  L  S  F  K  L  F  N  I  Q  V
901   AACAACAACTGGGGATTCCGGCCCAAGAAACTCAGCTTCAAGCTCTTCAACATCCAAGTT

321   R  G  V  T  Q  N  D  G  T  T  T  I  A  N  N  L  T  S  T  V
961   AGAGGGGTCACGCAGAACGATGGCACGACGACTATTGCCAATAACCTTACCAGCACGGTT

341   Q  V  F  T  D  S  E  Y  Q  L  P  Y  V  L  G  S  A  H  Q  G
1021  CAAGTGTTTACGGACTCGGAGTATCAGCTCCCGTACGTGCTCGGGTCGGCGCACCAAGGC

361   C  L  P  P  F  P  A  D  V  F  M  V  P  Q  Y  G  Y  L  T  L
1081  TGTCTCCCGCCGTTTCCAGCGGACGTCTTCATGGTCCCTCAGTATGGATACCTCACCCTG

381   N  N  G  S  Q  A  V  G  R  S  S  F  Y  C  L  E  Y  F  P  S
1141  AACAACGGAAGTCAAGCGGTGGGACGCTCATCCTTTTACTGCCTGGAGTACTTCCCTTCG

401   Q  M  L  R  T  G  N  N  F  Q  F  S  Y  T  F  E  D  V  P  F
1201  CAGATGCTAAGGACTGGAAATAACTTCCAATTCAGCTATACCTTCGAGGATGTACCTTTT

421   H  S  S  Y  A  H  S  Q  S  L  D  R  L  M  N  P  L  I  D  Q
1261  CACAGCAGCTACGCTCACAGCCAGAGTTTGGATCGCTTGATGAATCCTCTTATTGATCAG

441   Y  L  Y  Y  L  N  R  T  Q  G  T  T  S  G  T  T  N  Q  S  R
1321  TATCTGTACTACCTGAACAGAACGCAAGGAACAACCTCTGGAACAACCAACCAATCACGG
                                   RGCAMCVCNRGC      RCCRVCMHSMRSVVS

461   L  L  F  S  Q  A  G  P  Q  S  M  S  L  Q  A  R  N  W  L  P
1381  CTGCTTTTTAGCCAGGCTGGGCCTCAGTCTATGTCTTTGCAGGCCAGAAATTGGCTACCT
          VNG

481   G  P  C  Y  R  Q  Q  R  L  S  K  T  A  N  D  N  N  N  S  N
1441  GGGCCCTGCTACCGGCAACAGAGACTTTCAAAGACTGCTAACGACAACAACAACAGTAAC
                                  MARYCBMCRVCSRS              R  S

501   F  P  W  T  A  A  S  K  Y  H  L  N  G  R  D  S  L  V  N  P
1501  TTTCCTTGGACAGCGGCCAGCAAATATCATCTCAATGGCCGCGACTCGCTGGTGAATCCA
          M                  M
```

FIG. 1A

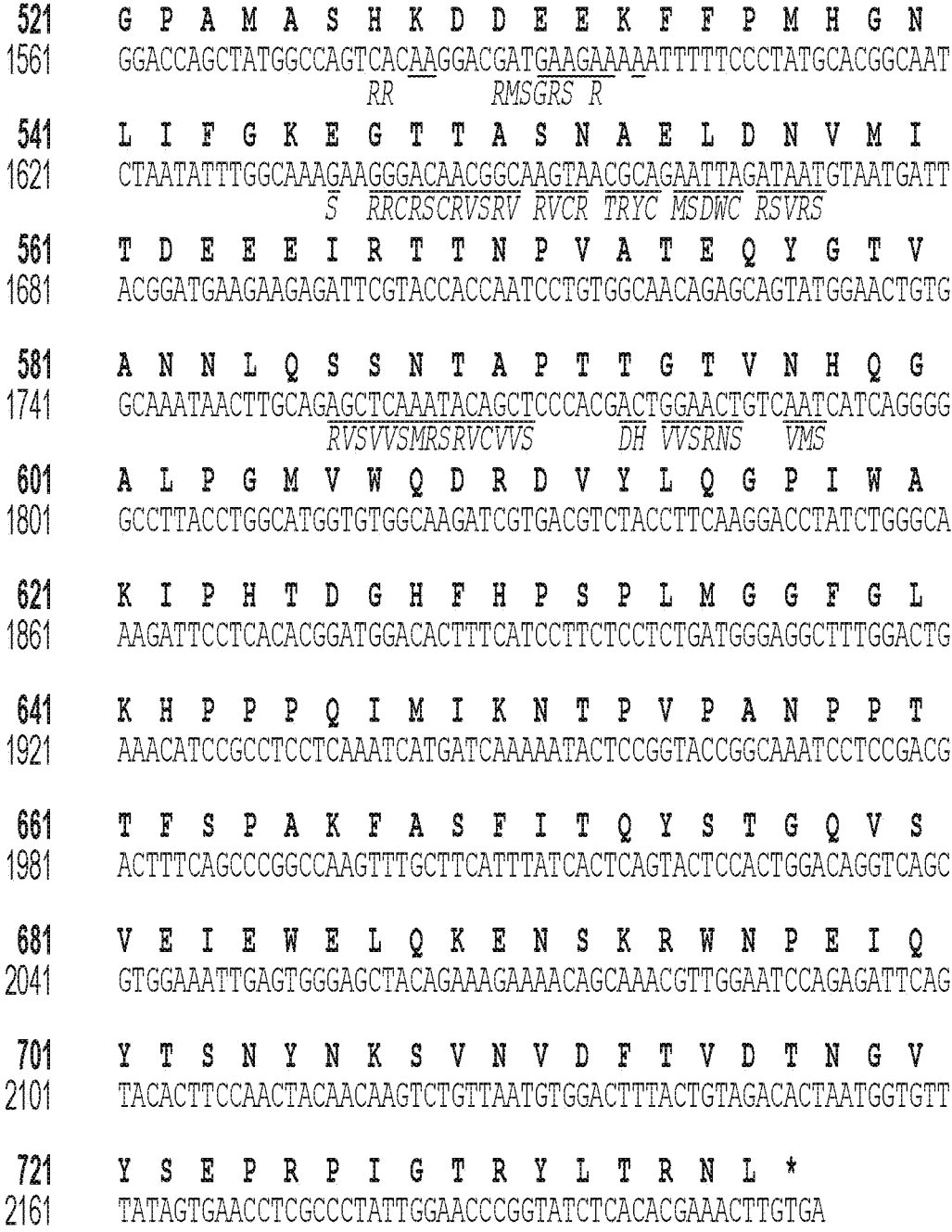

```
521       G  P  A  M  A  S  H  K  D  D  E  E  K  F  F  P  M  H  G  N
1561  GGACCAGCTATGGCCAGTCACAAGGACGATGAAGAAAAATTTTTCCCTATGCACGGCAAT
                          RR        RMSGRS R

541       L  I  F  G  K  E  G  T  T  A  S  N  A  E  L  D  N  V  M  I
1621  CTAATATTTGGCAAAGAAGGGACAACGGCAAGTAACGCAGAATTAGATAATGTAATGATT
                        S   RRCRSCRVSRV RVCR TRYC MSDWC RSVRS

561       T  D  E  E  I  R  T  T  N  P  V  A  T  E  Q  Y  G  T  V
1681  ACGGATGAAGAAGAGATTCGTACCACCAATCCTGTGGCAACAGAGCAGTATGGAACTGTG

581       A  N  N  L  Q  S  S  N  T  A  P  T  T  G  T  V  N  H  Q  G
1741  GCAAATAACTTGCAGAGCTCAAATACAGCTCCCACGACTGGAACTGTCAATCATCAGGGG
                        RVSVVSMRSRVCVVS       DH VVSRNS   VMS

601       A  L  P  G  M  V  W  Q  D  R  D  V  Y  L  Q  G  P  I  W  A
1801  GCCTTACCTGGCATGGTGTGGCAAGATCGTGACGTCTACCTTCAAGGACCTATCTGGGCA

621       K  I  P  H  T  D  G  H  F  H  P  S  P  L  M  G  G  F  G  L
1861  AAGATTCCTCACACGGATGGACACTTTCATCCTTCTCCTCTGATGGGAGGCTTTGGACTG

641       K  H  P  P  P  Q  I  M  I  K  N  T  P  V  P  A  N  P  P  T
1921  AAACATCCGCCTCCTCAAATCATGATCAAAAATACTCCGGTACCGGCAAATCCTCCGACG

661       T  F  S  P  A  K  F  A  S  F  I  T  Q  Y  S  T  G  Q  V  S
1981  ACTTTCAGCCCGGCCAAGTTTGCTTCATTTATCACTCAGTACTCCACTGGACAGGTCAGC

681       V  E  I  E  W  E  L  Q  K  E  N  S  K  R  W  N  P  E  I  Q
2041  GTGGAAATTGAGTGGGAGCTACAGAAAGAAAACAGCAAACGTTGGAATCCAGAGATTCAG

701       Y  T  S  N  Y  N  K  S  V  N  V  D  F  T  V  D  T  N  G  V
2101  TACACTTCCAACTACAACAAGTCTGTTAATGTGGACTTTACTGTAGACACTAATGGTGTT

721       Y  S  E  P  R  P  I  G  T  R  Y  L  T  R  N  L  *
2161  TATAGTGAACCTCGCCCTATTGGAACCCGGTATCTCACACGAAACTTGTGA
```

FIG. 1B

```
                              ApaI
ACCACCAGCACCAGAACCTGGGCCCTGCCCACTTACAACAACCATCTCTACAAGCAAATC
TCCAGCVVMDCAGGAGCTASCAACGACAACCACTACTTTGGCTACAGCACCCCTTGGGGG
TATTTTGACTTTAACAGATTCCACTGCCACTTCTCACCACGTGACTGGCAGCGACTCATT
AACAACAACTGGGGATTCCGGCCCAAGAAACTCAGCTTCAAGCTCTTCAACATCCAAGTT
AGAGGGGTCACGCAGAACGATGGCACGACGACTATTGCCAATAACCTTACCAGCACGGTT
CAAGTGTTTACGGACTCGGAGTATCAGCTCCCGTACGTGCTCGGGTCGGCGCACCAAGGC
TGTCTCCCGCCGTTTCCAGCGGACGTCTTCATGGTCCCTCAGTATGGATACCTCACCCTG
AACAACGGAAGTCAAGCGGTGGGACGCTCATCCTTTTACTGCCTGGAGTACTTCCCTTCG
CAGATGCTAAGGACTGGAAATAACTTCCAATTCAGCTATACCTTCGAGGATGTACCTTTT
CACAGCAGCTACGCTCACAGCCAGAGTTTGGATCGCTTGATGAATCCTCTTATTGATCAG
TATCTGTACTACCTGAACAGAACGCAARGCAMCVCNRGCGGAACARCCRVCMHSMRSVVS
CTGVNGTTTAGCCAGGCTGGGCCTCAGTCTATGTCTTTGCAGGCCAGAAATTGGCTACCT
GGGCCCTGCTACCGGCAACAGAGACTTTCAAMARYCBMCRVCSRSAACAACAACAGTRAS
TTTCCTTGGMCAGCGGCCAGCAMATATCATCTCAATGGCCGCGACTCGCTGGTGAATCCA
GGACCAGCTATGGCCAGTCACRRGGACGATRMSGRSARATTTTTTCCCTATGCACGGCAAT
CTAATATTTGGCAAASAARRCRSCRVSRVARVCRATRYCGMSDWCGRSVRSGTAATGATT
ACGGATGAAGAAGAGATTCGTACCACCAATCCTGTGGCAACAGAGCAGTATGGAACTGTG
GCAAATAACTTGCAGRVSVVSMRSRVCVVSCCCACGDHTVVSRNSGTCVMSCATCAGGGG
GCCTTACCTGGCATGGTGTGTGGCAAGATCGTGACGTCTACCTTCAAGGACCTATCTGGGCA
                              AatII
```

FIG. 2

```
MAADGYLPDWLEDNLSEGIREWWALKPGVPQPKANQQHQDNRRGLVLPGYKYLGPGNGLD
KGEPVNEADAAALEHDKAYDQQLKAGDNPYLKYNHADAEFQERLQEDTSFGGNLGRAVFQ
AKKRILEPLGLVEEAAKTAPGKKGAVDQSPQEPDSSSGVGKSGKQPARKRLNFGQTGDSE
SVPDPQPLGEPPAAPTSLGSNTMASGGGAPMADNNEGADGVGNSSGNWHCDSQWLGDRVI
TTSTRTWALPTYNNHLYKQISSXXGAXNDNHYFGYSTPWGYFDFNRFHCHFSPRDWQRLI
NNNWGFRPKKLSFKLFNIQVRGVTQNDGTTTIANNLTSTVQVFTDSEYQLPYVLGSAHQG
CLPPFPADVFMVPQYGYLTLNNGSQAVGRSSFYCLEYFPSQMLRTGNNFQFSYTFEDVPF
HSSYAHSQSLDRLMNPLIDQYLYYLNRTQXXXXGTXXXXXLXFSQAGPQSMSLQARNWLP
GPCYRQQRLSXXXXXNNNSXFPWXAASXYHLNGRDSLVNPGPAMASHXDDXXXFFPMHGN
LIFGKXXXXXXXXXXXXXVMITDEEEIRTTNPVATEQYGTVANNLQXXXXXPTXXXVXHQG
ALPGMVWQDRDVYLQGPIWA
```

FIG. 3

AAV3B/MP5 alignment

```
                    1                                                                                                  100
wt AAV3B VP1    (1)  MAADGYLPDWLEDNLSEGIREWWALKPGVPQPKANQQHQDNRRGLVLPGYKYLGPGNGLDKGEPVNEADAAALEHDKAYDQLKAGDNPYLKYNHADAEE
   AAV3B-MP5    (1)  MAADGYLPDWLEDNLSEGIREWWALKPGVPQPKANQQHQDNRRGLVLPGYKYLGPGNGLDKGEPVNEADAAALEHDKAYDQLKAGDNPYLKYNHADAEE 101                                                                                                200
wt AAV3B VP1  (101)  QERLQEDTSFGGNLGRAVFQAKKRILEPIGLVEEAAKTAPGKKRPVDQSPQEPDSSSGVGKSGKQPARKRLNFGQTGDSESVPDPQPLGEPPAAPTSLGS
   AAV3B-MP5  (101)  QERLQEDTSFGGNLGRAVFQAKKRILEPIGLVEEAAKTAPGKKRPVDQSPQEPDSSSGVGKSGKQPARKRLNFGQTGDSESVPDPQPLGEPPAAPTSLGS 201                                                                                                300
wt AAV3B VP1  (201)  NTMASGGGAPMADNNEGADGVGNSSGNWHCDSQWLGDRVITTSTRTWALPTYNNHLYKQISSQGASNDNHYFGYSTPWGYFDFNRFHCHFSPRDWQRLI
   AAV3B-MP5  (201)  NTMASGGGAPMADNNEGADGVGNSSGNWHCDSQWLGDRVITTSTRTWALPTYNNHLYKQISSASGASNDNHYFGYSTPWGYFDFNRFHCHFSPRDWQRLI 301                                                                                                400
wt AAV3B VP1  (301)  NNNWGFRPKKLSFKLFNIQVKEVTQNDGTTTIANNLTSTVQVFTDSEYQLPYVLGSAHQGCLPPFPADVFMPQYGYLTLNNGSQAVGRSFYCLEYFPS
   AAV3B-MP5  (301)  NNNWGFRPKKLSFKLFNIQVKEVTQNDGTTTIANNLTSTVQVFTDSEYQLPYVLGSAHQGCLPPFPADVFMPQYGYLTLNNGSQAVGRSFYCLEYFPS 401                                                                                                500
wt AAV3B VP1  (401)  QMLRTGNNFQFSYTFEDVPFHSSYAHSQSLDRLMNPLIDQYLYYLNRTQGTTSGTTNQSRLLFSQAGPQSMSLQARNWLPGPCYRQQRLSKTANDNNNSN
   AAV3B-MP5  (401)  QMLRTGNNFQFSYTFEDVPFHSSYAHSQSLDRLMNPLIDQYLYYLNRTQGTTSGTTNGLKFSQAGPQSMSLQARNWLPGPCYRQQRLSKIPSQNNWSN 501                                                                                                600
wt AAV3B VP1  (501)  FPWTAASKYHLNGRDSLVNPGPAMASHKDDEKFFPMHGNLIFGKEGTTASNAELDNVMITDEEEIRTTNPVATEQYGTVANNLQSSNTAPTTRTVNDQG
   AAV3B-MP5  (501)  FPWTAASKYHLNGRDSLVNPGPAMASHKDDDREFPMHGNLIFGKQGAGRDNTEYDHVMITDEEEIRTTNPVATEQYGTVANNLQSSNTAPTTRTVNDQG 601                                                                                                700
wt AAV3B VP1  (601)  ALPGMVWQDRDVYLQGPIWAKIPHTDGHFHPSPLMGGFGLKHPPPQIMIKNTPVPANPPTTFSPAKFASFITQYSTGQVSVEIEWELQKENSKRWNPEIQ
   AAV3B-MP5  (601)  ALPGMVWQDRDVYLQGPIWAKIPHTDGHFHPSPLMGGFGLKHPPPQIMIKNTPVPANPPTTFSPAKFASFITQYSTGQVSVEIEWELQKENSKRWNPEIQ 701                          737
wt AAV3B VP1  (701)  YTSNYNKSVNVDFTVDTNGVYSEPRPIGTRYLTRNL-
   AAV3B-MP5  (701)  YTSNYNKSVNVDFTVDTNGVYSEPRPIGTRYLTRNL-
```

FIG. 11

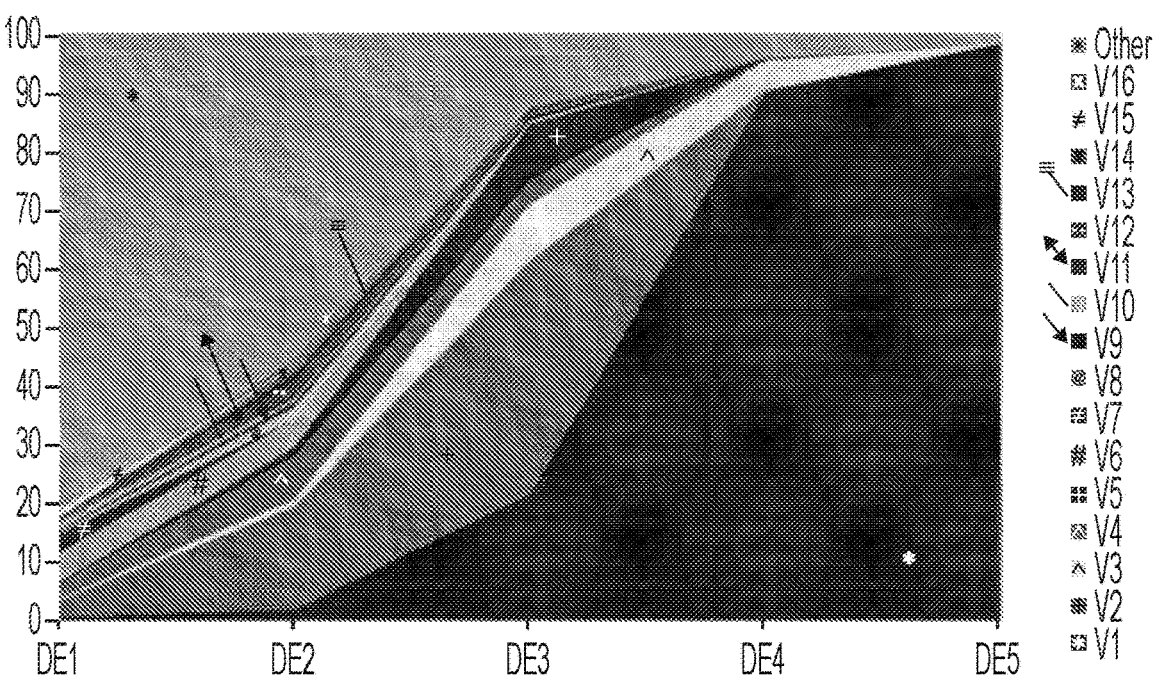
FIG. 17
| | 263 | 450 | 491 | 528 | 546 |
|---|---|---|---|---|---|
| AAV3B | QSGAS | GTTSGTTNQSRLL | KTANDNNNSNFPWTAASK | KDDEEK | EGTTASNAELDN |
| AAV3B-DE5 | A.... | S.PG...GTNG.X | .IPSQ............. | ...DDR | Q.AGRD.T.Y.H |
FIG. 18A
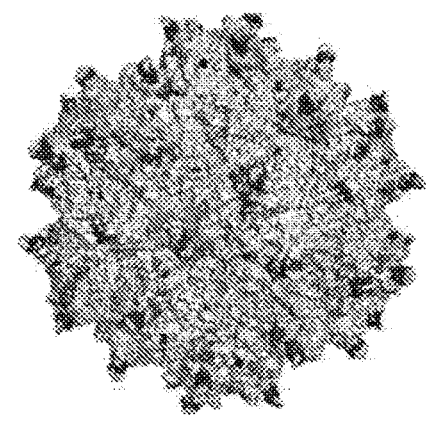
FIG. 18B

| | 1-2 | 2-3 | 3-4 | 4-5 |
|---|---|---|---|---|
| 263A | 0.573 | 2.819 | 3.756 | 1.078 |
| 450S | 1.286 | 1.046 | 1.006 | 0.998 |
| 452P | 0.916 | 0.990 | 3.730 | 1.074 |
| 453G | 0.657 | 1.109 | 2.705 | 1.008 |
| 457G | 1.061 | 2.743 | 2.571 | 1.070 |
| 458T | 3.136 | 1.616 | 1.154 | 1.066 |
| 459N | 0.784 | 3.891 | 2.787 | 1.011 |
| 460G | 3.599 | 2.098 | 2.659 | 1.071 |
| 462K | 2.123 | 1.341 | 1.343 | 1.073 |
| 492I | 1.692 | 1.114 | 1.138 | 1.005 |
| 493P | 1.124 | 0.830 | 3.099 | 1.077 |
| 494S | 0.766 | 4.529 | 3.836 | 1.077 |
| 499Q | 0.704 | 3.507 | 2.749 | 1.011 |
| 531D | 1.743 | 1.004 | 1.234 | 1.069 |
| 532D | 1.497 | 1.245 | 1.351 | 1.078 |
| 533R | 1.080 | 1.452 | 2.400 | 1.009 |
| 546O | 0.541 | 1.542 | 2.770 | 1.008 |
| 548A | 0.920 | 1.391 | 2.370 | 1.009 |
| 549G | 2.201 | 1.107 | 1.235 | 1.073 |
| 550R | 1.641 | 1.253 | 3.147 | 1.079 |
| 551D | 1.676 | 2.030 | 3.839 | 1.078 |
| 553T | 1.226 | 3.476 | 3.778 | 1.075 |
| 555Y | 0.953 | 3.636 | 3.767 | 1.079 |
| 557H | 2.773 | 4.233 | 3.802 | 1.077 |

FIG. 18C

Fold difference in NAb titers (wt AAV3B : AAV3B-DE5)

2-16
1.5-2
1-1.5
0.7-1

SEQUENCE LISTING

```
<160> NUMBER OF SEQ ID NOS: 124

<210> SEQ ID NO 1
<211> LENGTH: 736
<212> TYPE: PRT
<213> ORGANISM: Artificial Sequence
<220> FEATURE:
<223> OTHER INFORMATION: Synthetic

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

```
Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
                595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Asn Lys Ser Val Asn Val Asp Phe Thr Val Asp Thr Asn Gly Val
705                 710                 715                 720
```

-continued

```
Tyr Ser Glu Pro Arg Pro Ile Gly Thr Arg Tyr Leu Thr Arg Asn Leu
                725             730             735

<210> SEQ ID NO 2
<211> LENGTH: 736
<212> TYPE: PRT
<213> ORGANISM: Artificial Sequence
<220> FEATURE:
<223> OTHER INFORMATION: Synthetic

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
            115                 120                 125

Leu Gly Leu Val Glu Glu Ala Ala Lys Thr Ala Pro Gly Lys Lys Arg
        130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350
```

Val Leu Gly Ser Ala His Gln Gly Cys Leu Pro Pro Phe Pro Ala Asp
        355             360             365

Val Phe Met Val Pro Gln Tyr Gly Tyr Leu Thr Leu Asn Asn Gly Ser
        370             375             380

Gln Ala Val Gly Arg Ser Ser Phe Tyr Cys Leu Glu Tyr Phe Pro Ser
385             390             395             400

Gln Met Leu Arg Thr Gly Asn Asn Phe Gln Phe Ser Tyr Thr Phe Glu
            405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Asn Arg Thr
            435             440             445

Gln Ser Thr Pro Gly Gly Thr Thr Gly Thr Asn Gly Leu Lys Phe Ser
        450             455             460

Gln Ala Gly Pro Gln Ser Met Ser Leu Gln Ala Arg Asn Trp Leu Pro
465             470             475             480

Gly Pro Cys Tyr Arg Gln Gln Arg Leu Ser Lys Ile Pro Ser Gln Asn
            485             490             495

Asn Asn Ser Asn Phe Pro Trp Thr Ala Ala Ser Lys Tyr His Leu Asn
            500             505             510

Gly Arg Asp Ser Leu Val Asn Pro Gly Pro Ala Met Ala Ser His Lys
            515             520             525

Asp Asp Asp Asp Arg Phe Phe Pro Met His Gly Asn Leu Ile Phe Gly
            530             535             540

Lys Gln Gly Ala Gly Arg Asp Asn Thr Glu Tyr Asp His Val Met Ile
545             550             555             560

Thr Asp Glu Glu Glu Ile Arg Thr Thr Asn Pro Val Ala Thr Glu Gln
            565             570             575

Tyr Gly Thr Val Ala Asn Asn Leu Gln Ser Ser Asn Thr Ala Pro Thr
            580             585             590

Thr Arg Thr Val Asn Asp Gln Gly Ala Leu Pro Gly Met Val Trp Gln
            595             600             605

Asp Arg Asp Val Tyr Leu Gln Gly Pro Ile Trp Ala Lys Ile Pro His
            610             615             620

Thr Asp Gly His Phe His Pro Ser Pro Leu Met Gly Gly Phe Gly Leu
625             630             635             640

Lys His Pro Pro Pro Gln Ile Met Ile Lys Asn Thr Pro Val Pro Ala
            645             650             655

Asn Pro Pro Thr Thr Phe Ser Pro Ala Lys Phe Ala Ser Phe Ile Thr
            660             665             670

Gln Tyr Ser Thr Gly Gln Val Ser Val Glu Ile Glu Trp Glu Leu Gln
            675             680             685

Lys Glu Asn Ser Lys Arg Trp Asn Pro Glu Ile Gln Tyr Thr Ser Asn
            690             695             700

Tyr Asn Lys Ser Val Asn Val Asp Phe Thr Val Asp Thr Asn Gly Val
705             710             715             720

Tyr Ser Glu Pro Arg Pro Ile Gly Thr Arg Tyr Leu Thr Arg Asn Leu
            725             730             735

<210> SEQ ID NO 3
<211> LENGTH: 13
<212> TYPE: PRT
<213> ORGANISM: Artificial Sequence
<220> FEATURE:
<223> OTHER INFORMATION: Synthetic -continued

```
<400> SEQUENCE: 3

Ser Thr Pro Gly Gly Thr Thr Gly Thr Asn Gly Leu Lys
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Ile Pro Ser Gln Asn Asn Asn Ser Asn Phe Pro Trp Thr Ala Ala Ser
1               5                   10                  15

Lys

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Gly Lys Gln Gly Ala Gly Arg Asp Asn Thr Glu Tyr Asp His
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Gln Ser Ser Asn Thr Ala Pro Thr Thr Arg Thr Val Asn Asp
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: may be Proline or Alanine
<220> FEATURE:
<221> NAME/KEY: misc_feature
<222> LOCATION: (4)..(4)
<223> OTHER INFORMATION: may be Serine or Glycine
<220> FEATURE:
<221> NAME/KEY: misc_feature
<222> LOCATION: (10)..(10)
<223> OTHER INFORMATION: may be Serine or Asparagine
<220> FEATURE:
<221> NAME/KEY: misc_feature
<222> LOCATION: (11)..(11)
<223> OTHER INFORMATION: may be Threonine or Glycine
<220> FEATURE:
<221> NAME/KEY: misc_feature
<222> LOCATION: (12)..(12)
<223> OTHER INFORMATION: may be Lysine or Arginine
<220> FEATURE:
<221> NAME/KEY: misc_feature
<222> LOCATION: (13)..(13)
<223> OTHER INFORMATION: may be Lysine or Arginine
```

```
<400> SEQUENCE: 7

Ser Thr Xaa Xaa Gly Thr Thr Gly Thr Xaa Xaa Leu Xaa
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Gln Asn Gly Arg Asp Asn Pro Thr Phe Arg Asp Val Gln His
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Lys Asp Asp Asp Asp Arg
1               5

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ggctgggcga cagagtcatc                                                      20

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
gctggagatt tgcttgtaga gatg                                                 24

<210> SEQ ID NO 12
<211> LENGTH: 60
<212> TYPE: DNA
<213> ORGANISM: Artificial Sequence
<220> FEATURE:
<223> OTHER INFORMATION: Synthetic

<400> SEQUENCE: 12
catctctaca agcaaatctc cagcvvmdca ggagctasca acgacaacca ctactttggc         60

<210> SEQ ID NO 13
<211> LENGTH: 56
<212> TYPE: DNA
<213> ORGANISM: Artificial Sequence
<220> FEATURE:
<223> OTHER INFORMATION: Synthetic

<400> SEQUENCE: 13
ccaaggaaas tyactgttgt tgttsysgby gkvgrytktt gaaagtctct gttgcc            56
```

<210> SEQ ID NO 14
<211> LENGTH: 52
<212> TYPE: DNA
<213> ORGANISM: Artificial Sequence
<220> FEATURE:
<223> OTHER INFORMATION: Synthetic

<400> SEQUENCE: 14
aacaacaaca gtrastttcc ttggmcagcg gccagcamat atcatctcaa tg              52

<210> SEQ ID NO 15
<211> LENGTH: 58
<212> TYPE: DNA
<213> ORGANISM: Artificial Sequence
<220> FEATURE:
<223> OTHER INFORMATION: Synthetic

<400> SEQUENCE: 15
gattgccgtg catagggaaa aatytsycsk yatcgtccyy gtgactggcc atagctgg        58

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
atttttccct atgcacggca atc                                             23

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
catccgtgtg aggaatcttt gc                                              22

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
ttgcgttctg ttcaggtagt acaga                                           25

<210> SEQ ID NO 19
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 19
ctgtactacc tgaacagaac gcaargcamc vcnrgcggaa carccrvcmh smrsvvsctg      60

-continued

```
vngtttagcc aggctgggcc                                            80

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
tttgccaaat attagattgc c                                          21

<210> SEQ ID NO 21
<211> LENGTH: 80
<212> TYPE: DNA
<213> ORGANISM: Artificial Sequence
<220> FEATURE:
<223> OTHER INFORMATION: Synthetic

<400> SEQUENCE: 21
cggcaatcta atatttggca aasaarrcrs crvsrvarvc ratrycgmsd wcgrsvrsgt  60
aatgattacg gatgaagaag                                            80

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
ctgcaagtta tttgccacag ttc                                        23

<210> SEQ ID NO 23
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: n is a, c, g, or t

<400> SEQUENCE: 23
gaactgtggc aaataacttg cagrvsvvsm rsrvcvvscc cacgdhtvvs rnsgtcvmsc  60 atcaggggc cttacctg                                               78

<210> SEQ ID NO 24
<211> LENGTH: 28
<212> TYPE: DNA
<213> ORGANISM: Artificial Sequence
<220> FEATURE:
<223> OTHER INFORMATION: Synthetic

<400> SEQUENCE: 24
cagtatctgt actacctgaa cagaacgc                                   28

<210> SEQ ID NO 25
<211> LENGTH: 28
<212> TYPE: DNA
<213> ORGANISM: Artificial Sequence
<220> FEATURE:
<223> OTHER INFORMATION: Synthetic
```

-continued

<400> SEQUENCE: 25
gcgttctgtt caggtagtac agatactg                                              28

<210> SEQ ID NO 26
<211> LENGTH: 26
<212> TYPE: DNA
<213> ORGANISM: Artificial Sequence
<220> FEATURE:
<223> OTHER INFORMATION: Synthetic

<400> SEQUENCE: 26
cctgggccct gctaccggca acagag                                               26

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
ctctgttgcc ggtagcaggg cccagg                                               26

<210> SEQ ID NO 28
<211> LENGTH: 28
<212> TYPE: DNA
<213> ORGANISM: Artificial Sequence
<220> FEATURE:
<223> OTHER INFORMATION: Synthetic

<400> SEQUENCE: 28
ccctatgcac ggcaatctaa tatttggc                                             28

<210> SEQ ID NO 29
<211> LENGTH: 28
<212> TYPE: DNA
<213> ORGANISM: Artificial Sequence
<220> FEATURE:
<223> OTHER INFORMATION: Synthetic

<400> SEQUENCE: 29
gccaaatatt agattgccgt gcataggg                                             28

<210> SEQ ID NO 30
<211> LENGTH: 49
<212> TYPE: PRT
<213> ORGANISM: Artificial Sequence
<220> FEATURE:
<223> OTHER INFORMATION: Synthetic

<400> SEQUENCE: 30

Gly Thr Thr Ser Gly Thr Thr Asn Gln Ser Arg Leu Leu Lys Thr Ala
1               5                   10                  15

Asn Asp Asn Asn Asn Ser Asn Phe Pro Trp Thr Ala Ala Ser Lys Lys
            20                  25                  30

Asp Asp Glu Glu Lys Glu Gly Thr Thr Ala Ser Asn Ala Glu Leu Asp
        35                  40                  45

Asn

<210> SEQ ID NO 31
<211> LENGTH: 49
<212> TYPE: PRT
<213> ORGANISM: Artificial Sequence
<220> FEATURE:

<223> OTHER INFORMATION: Synthetic

<400> SEQUENCE: 31

Gly Thr Thr Ser Gly Thr Thr Asn Gln Ser Arg Leu Leu Lys Thr Ala
1               5                   10                  15

Asn Asp Asn Asn Asn Ser Asn Phe Pro Trp Thr Ala Ala Ser Lys Lys
                20                  25                  30

Asp Asp Glu Glu Lys Glu Gly Thr Thr Ala Ser Asn Ala Glu Leu Asp
        35                  40                  45

Asn

<210> SEQ ID NO 32
<211> LENGTH: 49
<212> TYPE: PRT
<213> ORGANISM: Artificial Sequence
<220> FEATURE:
<223> OTHER INFORMATION: Synthetic

<400> SEQUENCE: 32

Gly Asn Thr Gly Gly Thr Thr Ser Pro Ser Arg Leu Arg Lys Ile Tyr
1               5                   10                  15

Asp Arg Asn Asn Asn Ser Asn Phe Pro Trp Thr Ala Ala Ser Thr Gly
                20                  25                  30

Asp Asp Thr Gly Arg Gln Gly Thr Gly Glu Gly Asn Val Glu Val Gly
        35                  40                  45

Lys

<210> SEQ ID NO 33
<211> LENGTH: 49
<212> TYPE: PRT
<213> ORGANISM: Artificial Sequence
<220> FEATURE:
<223> OTHER INFORMATION: Synthetic

<400> SEQUENCE: 33

Ser Thr Thr Ser Gly Thr Thr Gly Gln Arg Lys Leu Ala Lys Ala Tyr
1               5                   10                  15

Gly His Asn Asn Asn Ser Asp Phe Pro Trp Pro Ala Ala Ser Thr Gly
                20                  25                  30

Asp Asp Glu Asp Arg Gln Asp Ser Gly Glu Asn Asp Val Ala Ile Gly
        35                  40                  45

Arg

<210> SEQ ID NO 34
<211> LENGTH: 49
<212> TYPE: PRT
<213> ORGANISM: Artificial Sequence
<220> FEATURE:
<223> OTHER INFORMATION: Synthetic

<400> SEQUENCE: 34

Gly Thr Ala Ser Gly Thr Thr Ala Asn Ser Asn Leu Lys Lys Thr Tyr
1               5                   10                  15

Ser Asp Asn Asn Asn Ser Asn Phe Pro Trp Thr Ala Ala Ser Lys Gly
                20                  25                  30

Asp Asp Asp Asp Arg Glu Gly Thr Asp Gly Ala Asn Val Glu Ile Asp
        35                  40                  45

Arg

-continued

```
<210> SEQ ID NO 35
<211> LENGTH: 49
<212> TYPE: PRT
<213> ORGANISM: Artificial Sequence
<220> FEATURE:
<223> OTHER INFORMATION: Synthetic

<400> SEQUENCE: 35

Gly Thr Pro Ser Gly Thr Ala Ala His Lys Thr Leu Glu Lys Thr Ser
1               5                   10                  15

Ala Glu Asn Asn Asn Ser Asn Phe Pro Trp Thr Ala Ala Ser Lys Gly
            20                  25                  30

Asp Asp Ala Gly Arg Glu Asp Ala Glu Gly Gly Asp Ala Ala Ile Gly
        35                  40                  45

Gly

<210> SEQ ID NO 36
<211> LENGTH: 49
<212> TYPE: PRT
<213> ORGANISM: Artificial Sequence
<220> FEATURE:
<223> OTHER INFORMATION: Synthetic

<400> SEQUENCE: 36

Ser Thr Ala Gly Gly Thr Ala Thr Gln Lys Ala Leu Thr Lys Val His
1               5                   10                  15

Ala His Asn Asn Asn Ser Asn Phe Pro Trp Thr Ala Ala Ser Lys Glu
            20                  25                  30

Asp Asp Thr Gly Arg Gln Asp Ala Thr Arg Ser Asn Val Ala Phe Glu
        35                  40                  45

Glu

<210> SEQ ID NO 37
<211> LENGTH: 49
<212> TYPE: PRT
<213> ORGANISM: Artificial Sequence
<220> FEATURE:
<223> OTHER INFORMATION: Synthetic

<400> SEQUENCE: 37

Gly Asn Pro Ser Gly Thr Thr Gly Leu Arg Gly Leu Thr Thr Thr Asp
1               5                   10                  15

Asn Glu Asn Asn Asn Ser Asn Phe Pro Trp Pro Ala Ala Ser Lys Lys
            20                  25                  30

Asp Asp Ala Gly Lys Gln Gly Thr Asp Gly Asn Asn Ile Ala Phe Gly
        35                  40                  45

Glu

<210> SEQ ID NO 38
<211> LENGTH: 49
<212> TYPE: PRT
<213> ORGANISM: Artificial Sequence
<220> FEATURE:
<223> OTHER INFORMATION: Synthetic

<400> SEQUENCE: 38

Gly Asn Thr Ser Gly Thr Thr Ser Lys Arg Pro Leu Met Thr Thr Ala
1               5                   10                  15

Asn Glu Asn Asn Asn Ser Asn Phe Pro Trp Thr Ala Ala Ser Thr Glu
            20                  25                  30

Asp Asp Asn Glu Arg Glu Asp Ala Lys Gly Thr Asp Thr Glu Phe Asp
```

```
            35                  40                  45

Arg

<210> SEQ ID NO 39
<211> LENGTH: 49
<212> TYPE: PRT
<213> ORGANISM: Artificial Sequence
<220> FEATURE:
<223> OTHER INFORMATION: Synthetic

<400> SEQUENCE: 39

Ser Asn Ala Ser Gly Thr Thr Gly Ile His Gln Leu Lys Thr Ala Pro
1               5                   10                  15

Asp Arg Asn Asn Asn Ser Glu Phe Pro Trp Thr Ala Ala Ser Lys Glu
            20                  25                  30

Asp Asp Asn Gly Arg Gln Asn Gly Ala Thr Ala Asp Thr Glu Val Glu
        35                  40                  45

Arg

<210> SEQ ID NO 40
<211> LENGTH: 49
<212> TYPE: PRT
<213> ORGANISM: Artificial Sequence
<220> FEATURE:
<223> OTHER INFORMATION: Synthetic

<400> SEQUENCE: 40

Ser Asn Thr Gly Gly Thr Thr Ala Met Arg Glu Leu Glu Lys Ala Pro
1               5                   10                  15

Asn Asp Asn Asn Asn Ser Lys Phe Pro Trp Thr Ala Ala Ser Thr Glu
            20                  25                  30

Asp Asp Thr Gly Lys Glu Ser Thr Ala Glu Thr Asp Val Glu Asp Gly
        35                  40                  45

Arg

<210> SEQ ID NO 41
<211> LENGTH: 49
<212> TYPE: PRT
<213> ORGANISM: Artificial Sequence
<220> FEATURE:
<223> OTHER INFORMATION: Synthetic

<400> SEQUENCE: 41

Ser Asn Ala Ser Gly Thr Ala Gly Leu Gln Arg Leu Lys Lys Ile Pro
1               5                   10                  15

Asp Gln Asn Asn Asn Ser Asn Phe Pro Trp Thr Ala Ala Ser Lys Lys
            20                  25                  30

Asp Asp Asn Gly Lys Gln Ser Gly Gly Ala Ala Asp Ile Asp Asn Gly
        35                  40                  45

Asn

<210> SEQ ID NO 42
<211> LENGTH: 49
<212> TYPE: PRT
<213> ORGANISM: Artificial Sequence
<220> FEATURE:
<223> OTHER INFORMATION: Synthetic

<400> SEQUENCE: 42

Gly Asn Pro Ser Gly Thr Thr Ala Pro His Arg Leu Leu Thr Ile His
1               5                   10                  15
```

-continued

Asn Gly Asn Asn Asn Ser Asn Phe Pro Trp Pro Ala Ala Ser Thr Lys
            20                  25                  30

Asp Asp Asp Gly Arg Gln Asp Gly Gly Thr Ser Asn Ile Asp Ile Asp
        35                  40                  45

Gly

<210> SEQ ID NO 43
<211> LENGTH: 49
<212> TYPE: PRT
<213> ORGANISM: Artificial Sequence
<220> FEATURE:
<223> OTHER INFORMATION: Synthetic

<400> SEQUENCE: 43

Gly Thr Pro Ser Gly Thr Thr Asp Leu Arg Glu Leu Ala Lys Ile Pro
1               5                   10                  15

Asn Asp Asn Asn Asn Ser Asn Phe Pro Trp Thr Ala Ala Ser Thr Glu
            20                  25                  30

Asp Asp Glu Asp Arg Glu Gly Thr Thr Ala Ser Asn Ala Glu Leu Asp
        35                  40                  45

Asn

<210> SEQ ID NO 44
<211> LENGTH: 49
<212> TYPE: PRT
<213> ORGANISM: Artificial Sequence
<220> FEATURE:
<223> OTHER INFORMATION: Synthetic

<400> SEQUENCE: 44

Ser Asn Pro Ser Gly Thr Ala Asn Pro Arg Thr Leu Met Lys Ile Asp
1               5                   10                  15

Ala His Asn Asn Asn Ser Glu Phe Pro Trp Pro Ala Ala Ser Thr Glu
            20                  25                  30

Asp Asp Asn Gly Lys Gln Ser Ser Thr Thr Gly Asp Val Glu Asp Asp
        35                  40                  45

Asp

<210> SEQ ID NO 45
<211> LENGTH: 49
<212> TYPE: PRT
<213> ORGANISM: Artificial Sequence
<220> FEATURE:
<223> OTHER INFORMATION: Synthetic

<400> SEQUENCE: 45

Gly Asn Ala Ser Gly Thr Thr Asp Thr Lys Arg Leu Thr Lys Ala Ser
1               5                   10                  15

Gly Gly Asn Asn Asn Ser Asn Phe Pro Trp Thr Ala Ala Ser Thr Lys
            20                  25                  30

Asp Asp Asp Asp Lys Glu Gly Ser Asn Arg Asp Asp Ala Glu Val Asp
        35                  40                  45

Arg

<210> SEQ ID NO 46
<211> LENGTH: 49
<212> TYPE: PRT
<213> ORGANISM: Artificial Sequence
<220> FEATURE:
<223> OTHER INFORMATION: Synthetic

<400> SEQUENCE: 46

Gly Asn Thr Gly Gly Thr Thr Asp Ile Arg Arg Leu Arg Lys Thr His
1               5                   10                  15

Ser Glu Asn Asn Asn Ser Glu Phe Pro Trp Thr Ala Ala Ser Thr Lys
            20                  25                  30

Asp Asp Asn Glu Arg Gln Asp Thr Arg Glu Thr Asp Val Ala Ile Asp
        35                  40                  45

Arg

<210> SEQ ID NO 47
<211> LENGTH: 49
<212> TYPE: PRT
<213> ORGANISM: Artificial Sequence
<220> FEATURE:
<223> OTHER INFORMATION: Synthetic

<400> SEQUENCE: 47

Gly Asn Ala Ser Gly Thr Ala Gly Met Arg Glu Leu Met Lys Ala Ala
1               5                   10                  15

Asn His Asn Asn Asn Ser Asn Phe Pro Trp Thr Ala Ala Ser Lys Glu
            20                  25                  30

Asp Asp Glu Asp Lys Glu Ser Gly Ser Ala Asp Asp Val Ala Ile Gly
        35                  40                  45

Arg

<210> SEQ ID NO 48
<211> LENGTH: 49
<212> TYPE: PRT
<213> ORGANISM: Artificial Sequence
<220> FEATURE:
<223> OTHER INFORMATION: Synthetic

<400> SEQUENCE: 48

Ser Asn Thr Gly Gly Thr Ala Thr Pro Lys Gln Leu Gln Lys Ala Ser
1               5                   10                  15

Ala His Asn Asn Asn Ser Glu Phe Pro Trp Thr Ala Ala Ser Lys Lys
            20                  25                  30

Asp Asp Glu Glu Arg Glu Gly Ser Thr Arg Asn Asp Ile Ala Asn Glu
        35                  40                  45

His

<210> SEQ ID NO 49
<211> LENGTH: 49
<212> TYPE: PRT
<213> ORGANISM: Artificial Sequence
<220> FEATURE:
<223> OTHER INFORMATION: Synthetic

<400> SEQUENCE: 49

Ser Asn Thr Gly Gly Thr Ala Asn Ile Lys Glu Leu Thr Lys Thr Ser
1               5                   10                  15

Asn Asp Asn Asn Asn Ser Asn Phe Pro Trp Thr Ala Ala Ser Thr Arg
            20                  25                  30

Asp Asp Asn Asp Lys Gln Ser Ala Ser Lys Asn Asp Ile Glu Tyr Glu
        35                  40                  45

Gln

<210> SEQ ID NO 50

-continued

```
<211> LENGTH: 49
<212> TYPE: PRT
<213> ORGANISM: Artificial Sequence
<220> FEATURE:
<223> OTHER INFORMATION: Synthetic

<400> SEQUENCE: 50

Ser Asn Ala Gly Gly Thr Thr Ser Asn Arg Glu Leu Arg Thr Thr Ser
1               5                   10                  15

Ser Gln Asn Asn Asn Ser Asn Phe Pro Trp Thr Ala Ala Ser Thr Arg
            20                  25                  30

Asp Asp Asp Asp Arg Gln Asp Ala Gly Gly Asn Asp Val Glu Val Gly
        35                  40                  45

Asp

<210> SEQ ID NO 51
<211> LENGTH: 49
<212> TYPE: PRT
<213> ORGANISM: Artificial Sequence
<220> FEATURE:
<223> OTHER INFORMATION: Synthetic

<400> SEQUENCE: 51

Ser Asn Thr Ser Gly Thr Ala Thr Thr Ser Ala Leu Lys Lys Thr Tyr
1               5                   10                  15

Gly His Asn Asn Asn Ser Asn Phe Pro Trp Thr Ala Ala Ser Lys Gly
            20                  25                  30

Asp Asp Thr Glu Lys Gln Gly Gly Ser Ala Asn Asn Val Glu Val Glu
        35                  40                  45

Ser

<210> SEQ ID NO 52
<211> LENGTH: 49
<212> TYPE: PRT
<213> ORGANISM: Artificial Sequence
<220> FEATURE:
<223> OTHER INFORMATION: Synthetic

<400> SEQUENCE: 52

Ser Asn Ala Gly Gly Thr Ala Ala Thr Asn Arg Leu Leu Lys Ile Tyr
1               5                   10                  15

Asp Arg Asn Asn Asn Ser Asn Phe Pro Trp Thr Ala Ala Ser Thr Arg
            20                  25                  30

Asp Asp Glu Asp Lys Glu Gly Gly Glu Lys Gly Asn Val Asp Ile Asp
        35                  40                  45

Arg

<210> SEQ ID NO 53
<211> LENGTH: 49
<212> TYPE: PRT
<213> ORGANISM: Artificial Sequence
<220> FEATURE:
<223> OTHER INFORMATION: Synthetic

<400> SEQUENCE: 53

Ser Thr Pro Ser Gly Thr Thr Ala Thr Lys Gly Leu Thr Thr Ala His
1               5                   10                  15

Thr Gly Asn Asn Asn Ser Asn Phe Pro Trp Thr Ala Ala Ser Lys Gly
            20                  25                  30

Asp Asp Asp Gly Lys Glu Gly Ser Thr Ala Thr Asp Val Ala Ile Gly
        35                  40                  45
```

Ser

<210> SEQ ID NO 54
<211> LENGTH: 49
<212> TYPE: PRT
<213> ORGANISM: Artificial Sequence
<220> FEATURE:
<223> OTHER INFORMATION: Synthetic

<400> SEQUENCE: 54

Gly Asn Thr Gly Gly Thr Thr Asp Leu Arg Arg Leu Met Thr Thr Asp
1               5                   10                  15

Asn His Asn Asn Asn Ser Glu Phe Pro Trp Pro Ala Ala Ser Thr Gly
                20                  25                  30

Asp Asp Lys Gly Arg Glu Asn Gly Ala Lys Asn Asp Ile Ala Phe Glu
        35                  40                  45

Gly

<210> SEQ ID NO 55
<211> LENGTH: 49
<212> TYPE: PRT
<213> ORGANISM: Artificial Sequence
<220> FEATURE:
<223> OTHER INFORMATION: Synthetic

<400> SEQUENCE: 55

Ser Thr Thr Ser Gly Thr Thr Thr Leu Lys Ala Leu Gln Lys Ile Pro
1               5                   10                  15

Asn Arg Asn Asn Asn Ser Asn Phe Pro Trp Thr Ala Ala Ser Thr Gly
                20                  25                  30

Asp Asp Glu Asp Arg Glu Asn Ser Lys Gly Ala Asn Thr Glu Ile Asp
        35                  40                  45

Glu

<210> SEQ ID NO 56
<211> LENGTH: 49
<212> TYPE: PRT
<213> ORGANISM: Artificial Sequence
<220> FEATURE:
<223> OTHER INFORMATION: Synthetic

<400> SEQUENCE: 56

Gly Thr Thr Ser Gly Thr Thr Asp Pro Lys Asp Leu Val Thr Thr His
1               5                   10                  15

Gly Asp Asn Asn Asn Ser Asp Phe Pro Trp Thr Ala Ala Ser Thr Lys
                20                  25                  30

Asp Asp Asp Asp Lys Glu Asp Thr Ala Ala Asp Asn Val Glu Phe Gly
        35                  40                  45

Arg

<210> SEQ ID NO 57
<211> LENGTH: 49
<212> TYPE: PRT
<213> ORGANISM: Artificial Sequence
<220> FEATURE:
<223> OTHER INFORMATION: Synthetic

<400> SEQUENCE: 57

Ser Thr Ala Gly Gly Thr Thr Thr Ile Lys Asp Leu Val Lys Val Pro
1               5                   10                  15

-continued

Asp Asp Asn Asn Asn Ser Lys Phe Pro Trp Thr Ala Ala Ser Lys Glu
         20                  25                  30

Asp Asp Asp Glu Arg Gln Asp Ser Gly Ala Thr Asn Val Glu Phe Gly
     35                  40                  45

Arg

<210> SEQ ID NO 58
<211> LENGTH: 49
<212> TYPE: PRT
<213> ORGANISM: Artificial Sequence
<220> FEATURE:
<223> OTHER INFORMATION: Synthetic

<400> SEQUENCE: 58

Gly Thr Thr Gly Gly Thr Thr Thr Met Arg Lys Leu Gly Lys Val Tyr
1               5                  10                  15

Gly Gly Asn Asn Asn Ser Asn Phe Pro Trp Thr Ala Ala Ser Thr Glu
         20                  25                  30

Asp Asp Ala Glu Arg Gln Ser Ser Gly Arg Asn Asp Val Glu Tyr Gly
     35                  40                  45

Asp

<210> SEQ ID NO 59
<211> LENGTH: 49
<212> TYPE: PRT
<213> ORGANISM: Artificial Sequence
<220> FEATURE:
<223> OTHER INFORMATION: Synthetic

<400> SEQUENCE: 59

Gly Asn Thr Gly Gly Thr Ala Ser Thr Arg Arg Leu Thr Lys Ile Pro
1               5                  10                  15

Asp Gln Asn Asn Asn Ser Asn Phe Pro Trp Pro Ala Ala Ser Lys Glu
         20                  25                  30

Asp Asp Glu Gly Arg Gln Ser Ala Glu Lys Gly Asp Ile Glu Tyr Gly
     35                  40                  45

Arg

<210> SEQ ID NO 60
<211> LENGTH: 49
<212> TYPE: PRT
<213> ORGANISM: Artificial Sequence
<220> FEATURE:
<223> OTHER INFORMATION: Synthetic

<400> SEQUENCE: 60

Gly Asn Thr Ser Gly Thr Thr Ala Thr His Thr Leu Ala Lys Ile His
1               5                  10                  15

Ser Arg Asn Asn Asn Ser Asp Phe Pro Trp Pro Ala Ala Ser Lys Glu
         20                  25                  30

Asp Asp Ala Gly Lys Gln Gly Ala Thr Ala Gly Asn Ile Asp Val Glu
     35                  40                  45

Gln

<210> SEQ ID NO 61
<211> LENGTH: 49
<212> TYPE: PRT
<213> ORGANISM: Artificial Sequence
<220> FEATURE:
<223> OTHER INFORMATION: Synthetic -continued

```
<400> SEQUENCE: 61

Ser Asn Pro Gly Gly Thr Thr Ser Ile Arg Gly Leu Gln Thr Ile Pro
1               5                   10                  15

Asn Arg Asn Asn Asn Ser Asn Phe Pro Trp Pro Ala Ala Ser Thr Arg
                20                  25                  30

Asp Asp Thr Asp Lys Gln Gly Gly Ala Gly Asn Thr Asp Phe Asp
        35                  40                  45

His

<210> SEQ ID NO 62
<211> LENGTH: 49
<212> TYPE: PRT
<213> ORGANISM: Artificial Sequence
<220> FEATURE:
<223> OTHER INFORMATION: Synthetic

<400> SEQUENCE: 62

Ser Thr Thr Ser Gly Thr Ala Ala Pro Arg Gly Leu Val Thr Val Tyr
1               5                   10                  15

Gly His Asn Asn Asn Ser Glu Phe Pro Trp Thr Ala Ala Ser Lys Lys
                20                  25                  30

Asp Asp Glu Gly Arg Glu Gly Ala Gly Ala Ser Asn Val Ala Ile Glu
        35                  40                  45

Glu

<210> SEQ ID NO 63
<211> LENGTH: 49
<212> TYPE: PRT
<213> ORGANISM: Artificial Sequence
<220> FEATURE:
<223> OTHER INFORMATION: Synthetic

<400> SEQUENCE: 63

Gly Asn Ala Ser Gly Thr Ala Thr Lys Gln Gly Leu Met Lys Val Pro
1               5                   10                  15

Asn Gln Asn Asn Asn Ser Asp Phe Pro Trp Thr Ala Ala Ser Lys Lys
                20                  25                  30

Asp Asp Asp Asp Arg Gln Ser Ser Asp Lys Asn Asn Ala Glu Asp Asp
        35                  40                  45

Ser

<210> SEQ ID NO 64
<211> LENGTH: 49
<212> TYPE: PRT
<213> ORGANISM: Artificial Sequence
<220> FEATURE:
<223> OTHER INFORMATION: Synthetic

<400> SEQUENCE: 64

Ser Asn Ala Gly Gly Thr Ala Thr Thr Ser Gln Leu Arg Thr Ala Pro
1               5                   10                  15

Ala Glu Asn Asn Asn Ser Asn Phe Pro Trp Pro Ala Ala Ser Thr Arg
                20                  25                  30

Asp Asp Ala Asp Arg Glu Ser Gly Arg Gly Asp Asn Val Asp Phe Glu
        35                  40                  45

Lys

<210> SEQ ID NO 65
<211> LENGTH: 49
```

<212> TYPE: PRT
<213> ORGANISM: Artificial Sequence
<220> FEATURE:
<223> OTHER INFORMATION: Synthetic

<400> SEQUENCE: 65

Ser Asn Thr Gly Gly Thr Ala Gly Ile Arg Ala Leu Gln Lys Val Asp
1               5                   10                  15

Thr Gly Asn Asn Asn Ser Asp Phe Pro Trp Thr Ala Ala Ser Thr Glu
            20                  25                  30

Asp Asp Thr Glu Lys Glu Asn Ser Ala Arg Asn Asp Ala Asp Ile Gly
        35                  40                  45

Arg

<210> SEQ ID NO 66
<211> LENGTH: 49
<212> TYPE: PRT
<213> ORGANISM: Artificial Sequence
<220> FEATURE:
<223> OTHER INFORMATION: Synthetic

<400> SEQUENCE: 66

Gly Asn Ala Ser Gly Thr Ala Ala Gln Asn Gly Leu Arg Lys Ile Pro
1               5                   10                  15

Asn Glu Asn Asn Asn Ser Lys Phe Pro Trp Thr Ala Ala Ser Thr Lys
            20                  25                  30

Asp Asp Glu Gly Lys Glu Ser Ser Ser Gly Asp Asp Ala Glu Phe Gly
        35                  40                  45

Gly

<210> SEQ ID NO 67
<211> LENGTH: 49
<212> TYPE: PRT
<213> ORGANISM: Artificial Sequence
<220> FEATURE:
<223> OTHER INFORMATION: Synthetic

<400> SEQUENCE: 67

Ser Asn Thr Ser Gly Thr Ala Gly Pro Gln Gln Leu Arg Lys Thr His
1               5                   10                  15

Ala Gln Asn Asn Asn Ser Asn Phe Pro Trp Thr Ala Ala Ser Lys Glu
            20                  25                  30

Asp Asp Thr Gly Lys Glu Gly Ala Arg Ala Asn Asp Ile Ala Phe Asp
        35                  40                  45

Gln

<210> SEQ ID NO 68
<211> LENGTH: 49
<212> TYPE: PRT
<213> ORGANISM: Artificial Sequence
<220> FEATURE:
<223> OTHER INFORMATION: Synthetic

<400> SEQUENCE: 68

Ser Thr Pro Ser Gly Thr Thr Ser Met Arg Thr Leu Glu Lys Ala Pro
1               5                   10                  15

Ala Arg Asn Asn Asn Ser Glu Phe Pro Trp Thr Ala Ala Ser Thr Arg
            20                  25                  30

Asp Asp Ala Gly Lys Gln Gly Ser Arg Glu Asn Asp Thr Glu Phe Asp
        35                  40                  45

Gly

<210> SEQ ID NO 69
<211> LENGTH: 49
<212> TYPE: PRT
<213> ORGANISM: Artificial Sequence
<220> FEATURE:
<223> OTHER INFORMATION: Synthetic

<400> SEQUENCE: 69

Ser Thr Ala Gly Gly Thr Thr Ala Leu Lys Gly Leu Lys Thr Ile Ala
1               5                   10                  15

Asp His Asn Asn Asn Ser Glu Phe Pro Trp Pro Ala Ala Ser Thr Arg
            20                  25                  30

Asp Asp Lys Glu Lys Glu Asp Ser Thr Gly Ala Asn Ile Ala Asp Asp
        35                  40                  45

Arg

<210> SEQ ID NO 70
<211> LENGTH: 49
<212> TYPE: PRT
<213> ORGANISM: Artificial Sequence
<220> FEATURE:
<223> OTHER INFORMATION: Synthetic

<400> SEQUENCE: 70

Ser Thr Pro Ser Gly Thr Ala Ser Thr Arg Thr Leu Met Lys Thr His
1               5                   10                  15

Asn His Asn Asn Asn Ser Glu Phe Pro Trp Thr Ala Ala Ser Thr Lys
            20                  25                  30

Asp Asp Glu Asp Lys Glu Gly Thr Glu Ala Thr Asn Val Ala Ile Gly
        35                  40                  45

Gly

<210> SEQ ID NO 71
<211> LENGTH: 49
<212> TYPE: PRT
<213> ORGANISM: Artificial Sequence
<220> FEATURE:
<223> OTHER INFORMATION: Synthetic

<400> SEQUENCE: 71

Gly Asn Pro Gly Gly Thr Thr Asn Asn Gln Ala Leu Arg Lys Ile His
1               5                   10                  15

Gly Gln Asn Asn Asn Ser Asp Phe Pro Trp Thr Ala Ala Ser Thr Arg
            20                  25                  30

Asp Asp Asn Asp Lys Glu Gly Ser Ala Arg Gly Asp Val Ala Tyr Glu
        35                  40                  45

Lys

<210> SEQ ID NO 72
<211> LENGTH: 49
<212> TYPE: PRT
<213> ORGANISM: Artificial Sequence
<220> FEATURE:
<223> OTHER INFORMATION: Synthetic

<400> SEQUENCE: 72

Ser Asn Ala Ser Gly Thr Thr Asp Thr Arg Glu Leu Val Thr Ile Ala
1               5                   10                  15

Asp Asp Asn Asn Asn Ser Glu Phe Pro Trp Thr Ala Ala Ser Thr Arg

-continued

```
              20              25              30

Asp Asp Thr Asp Lys Gln Gly Ser Ala Gly Ala Asp Val Glu Val Glu
        35              40              45

Lys

<210> SEQ ID NO 73
<211> LENGTH: 49
<212> TYPE: PRT
<213> ORGANISM: Artificial Sequence
<220> FEATURE:
<223> OTHER INFORMATION: Synthetic

<400> SEQUENCE: 73

Ser Asn Pro Gly Gly Thr Thr Asn Leu Arg Glu Leu Arg Thr Ile His
1               5              10              15

Thr Glu Asn Asn Asn Ser Glu Phe Pro Trp Thr Ala Ala Ser Thr Arg
        20              25              30

Asp Asp Lys Asp Arg Gln Gly Gly Gly Thr Asn Val Glu Ile Gly
        35              40              45

Ser

<210> SEQ ID NO 74
<211> LENGTH: 49
<212> TYPE: PRT
<213> ORGANISM: Artificial Sequence
<220> FEATURE:
<223> OTHER INFORMATION: Synthetic

<400> SEQUENCE: 74

Gly Thr Thr Gly Gly Thr Ala Asn Asn Asn Thr Leu Leu Lys Ile Ala
1               5              10              15

Ser Gly Asn Asn Asn Ser Asn Phe Pro Trp Thr Ala Ala Ser Thr Lys
        20              25              30

Asp Asp Lys Gly Arg Glu Gly Ala Glu Lys Asn Asp Thr Ala Val Gly
        35              40              45

Asn

<210> SEQ ID NO 75
<211> LENGTH: 49
<212> TYPE: PRT
<213> ORGANISM: Artificial Sequence
<220> FEATURE:
<223> OTHER INFORMATION: Synthetic

<400> SEQUENCE: 75

Gly Thr Thr Ser Gly Thr Thr Asp Lys Gln Gln Leu Met Lys Thr His
1               5              10              15

Asn Gly Asn Asn Asn Ser Asp Phe Pro Trp Thr Ala Ala Ser Lys Glu
        20              25              30

Asp Asp Thr Gly Lys Gln Ser Ala Glu Gly Asn Asn Val Ala Tyr Asp
        35              40              45

Gly

<210> SEQ ID NO 76
<211> LENGTH: 49
<212> TYPE: PRT
<213> ORGANISM: Artificial Sequence
<220> FEATURE:
<223> OTHER INFORMATION: Synthetic

<400> SEQUENCE: 76
```

-continued

```
Gly Thr Ala Gly Gly Thr Ala Thr Leu Ser Thr Leu Val Lys Ile Ser
1               5                   10                  15

Ala Gly Asn Asn Asn Ser Asp Phe Pro Trp Thr Ala Ala Ser Lys Gly
            20                  25                  30

Asp Asp Asn Gly Lys Gln Asn Ser Thr Ala Ser Asp Val Ala Ile Asp
        35                  40                  45

Gly

<210> SEQ ID NO 77
<211> LENGTH: 49
<212> TYPE: PRT
<213> ORGANISM: Artificial Sequence
<220> FEATURE:
<223> OTHER INFORMATION: Synthetic

<400> SEQUENCE: 77

Ser Asn Thr Ser Gly Thr Ala Gly Leu Arg Thr Leu Thr Lys Ala Asp
1               5                   10                  15

Ala Asp Asn Asn Asn Ser Asp Phe Pro Trp Pro Ala Ala Ser Thr Gly
            20                  25                  30

Asp Asp Asn Gly Lys Glu Asp Ala Ser Gly Asn Asn Val Glu Asp Gly
        35                  40                  45

Arg

<210> SEQ ID NO 78
<211> LENGTH: 49
<212> TYPE: PRT
<213> ORGANISM: Artificial Sequence
<220> FEATURE:
<223> OTHER INFORMATION: Synthetic

<400> SEQUENCE: 78

Ser Asn Ala Ser Gly Thr Ala Thr Pro Ser Thr Leu Arg Lys Thr Asp
1               5                   10                  15

Thr His Asn Asn Asn Ser Glu Phe Pro Trp Pro Ala Ala Ser Lys Arg
            20                  25                  30

Asp Asp Asn Asp Arg Glu Gly Ala Arg Gly Ser Asn Ile Asp Val Gly
        35                  40                  45

Asp

<210> SEQ ID NO 79
<211> LENGTH: 49
<212> TYPE: PRT
<213> ORGANISM: Artificial Sequence
<220> FEATURE:
<223> OTHER INFORMATION: Synthetic

<400> SEQUENCE: 79

Ser Thr Ala Ser Gly Thr Ala Ser Leu Arg Ala Leu Met Lys Val Pro
1               5                   10                  15

Asn Arg Asn Asn Asn Ser Asn Phe Pro Trp Thr Ala Ala Ser Thr Gly
            20                  25                  30

Asp Asp Asn Asp Lys Glu Asn Ala Arg Ala Ser Asp Ala Glu Val Asp
        35                  40                  45

Arg

<210> SEQ ID NO 80
<211> LENGTH: 49
<212> TYPE: PRT
```

-continued

<213> ORGANISM: Artificial Sequence
<220> FEATURE:
<223> OTHER INFORMATION: Synthetic

<400> SEQUENCE: 80

```
Gly Thr Ala Ser Gly Thr Ala Thr Thr Lys Gly Leu Leu Lys Ile Ser
1               5                   10                  15

Thr Gln Asn Asn Asn Ser Asn Phe Pro Trp Thr Ala Ala Ser Lys Glu
            20                  25                  30

Asp Asp Ala Asp Lys Gln Gly Gly Glu Thr Asp Asn Val Asp Val Gly
        35                  40                  45

Asp
```

<210> SEQ ID NO 81
<211> LENGTH: 49
<212> TYPE: PRT
<213> ORGANISM: Artificial Sequence
<220> FEATURE:
<223> OTHER INFORMATION: Synthetic

<400> SEQUENCE: 81

```
Gly Thr Ala Ser Gly Thr Ala Ala Leu Lys Gln Leu Ala Lys Ala Asp
1               5                   10                  15

Ser Asp Asn Asn Asn Ser Asn Phe Pro Trp Thr Ala Ala Ser Thr Glu
            20                  25                  30

Asp Asp Ala Asp Arg Gln Gly Gly Glu Thr Gly Asn Ile Glu Tyr Asp
        35                  40                  45

Gly
```

<210> SEQ ID NO 82
<211> LENGTH: 49
<212> TYPE: PRT
<213> ORGANISM: Artificial Sequence
<220> FEATURE:
<223> OTHER INFORMATION: Synthetic

<400> SEQUENCE: 82

```
Gly Asn Ala Ser Gly Thr Ala Thr Thr Ser Asn Leu Met Lys Ala Asp
1               5                   10                  15

Asp Arg Asn Asn Asn Ser Asn Phe Pro Trp Thr Ala Ala Ser Thr Lys
            20                  25                  30

Asp Asp Glu Asp Arg Gln Gly Ala Lys Arg Ser Asp Thr Ala Val Glu
        35                  40                  45

Glu
```

<210> SEQ ID NO 83
<211> LENGTH: 49
<212> TYPE: PRT
<213> ORGANISM: Artificial Sequence
<220> FEATURE:
<223> OTHER INFORMATION: Synthetic

<400> SEQUENCE: 83

```
Gly Thr Ala Gly Gly Thr Ala Asn Met Lys Asp Leu Arg Thr Thr Ala
1               5                   10                  15

Ser Glu Asn Asn Asn Ser Asp Phe Pro Trp Thr Ala Ala Ser Thr Glu
            20                  25                  30

Asp Asp Lys Asp Lys Glu Gly Ala Asn Gly Gly Asp Val Ala Ile Gly
        35                  40                  45

Gln
```

-continued

```
<210> SEQ ID NO 84
<211> LENGTH: 49
<212> TYPE: PRT
<213> ORGANISM: Artificial Sequence
<220> FEATURE:
<223> OTHER INFORMATION: Synthetic

<400> SEQUENCE: 84

Ser Thr Pro Gly Gly Thr Thr Thr Ile Arg Asp Leu Lys Thr Val Ser
1               5                   10                  15

Thr Asp Asn Asn Asn Ser Asp Phe Pro Trp Pro Ala Ala Ser Thr Lys
            20                  25                  30

Asp Asp Asp Asp Arg Glu Gly Ser Gly Arg Asn Asn Val Ala Val Glu
        35                  40                  45

Glu

<210> SEQ ID NO 85
<211> LENGTH: 49
<212> TYPE: PRT
<213> ORGANISM: Artificial Sequence
<220> FEATURE:
<223> OTHER INFORMATION: Synthetic

<400> SEQUENCE: 85

Ser Thr Pro Ser Gly Thr Ala Asn Ile Asn Thr Leu Arg Lys Thr Pro
1               5                   10                  15

Asn Arg Asn Asn Asn Ser Asn Phe Pro Trp Thr Ala Ala Ser Thr Glu
            20                  25                  30

Asp Asp Glu Gly Arg Gln Ser Ala Thr Lys Asp Asp Val Asp Ile Gly
        35                  40                  45

Gly

<210> SEQ ID NO 86
<211> LENGTH: 49
<212> TYPE: PRT
<213> ORGANISM: Artificial Sequence
<220> FEATURE:
<223> OTHER INFORMATION: Synthetic

<400> SEQUENCE: 86

Gly Asn Thr Gly Gly Thr Ala Gly Leu Gln Lys Leu Met Lys Thr His
1               5                   10                  15

Gly Gly Asn Asn Asn Ser Asn Phe Pro Trp Pro Ala Ala Ser Thr Lys
            20                  25                  30

Asp Asp Asp Gly Lys Gln Ser Ser Arg Gly Asn Asp Val Ala Val Asp
        35                  40                  45

Asp

<210> SEQ ID NO 87
<211> LENGTH: 49
<212> TYPE: PRT
<213> ORGANISM: Artificial Sequence
<220> FEATURE:
<223> OTHER INFORMATION: Synthetic

<400> SEQUENCE: 87

Gly Asn Thr Ser Gly Thr Thr Thr Pro Arg Thr Leu Ala Lys Ile Pro
1               5                   10                  15

Ser His Asn Asn Asn Ser Glu Phe Pro Trp Thr Ala Ala Ser Lys Lys
            20                  25                  30
```

-continued

```
Asp Asp Glu Glu Lys Gln Gly Ser Asn Gly Ser Asn Ile Glu Phe Gly
        35                  40                  45

Ser

<210> SEQ ID NO 88
<211> LENGTH: 49
<212> TYPE: PRT
<213> ORGANISM: Artificial Sequence
<220> FEATURE:
<223> OTHER INFORMATION: Synthetic

<400> SEQUENCE: 88

Ser Asn Ala Gly Gly Thr Ala Gly Leu Arg Gln Leu Thr Lys Ala Pro
1               5                   10                  15

Ala Glu Asn Asn Asn Ser Asp Phe Pro Trp Thr Ala Ala Ser Thr Glu
        20                  25                  30

Asp Asp Ala Gly Lys Glu Gly Gly Gly Gly Ala Asn Ile Ala Val Glu
        35                  40                  45

Glu

<210> SEQ ID NO 89
<211> LENGTH: 49
<212> TYPE: PRT
<213> ORGANISM: Artificial Sequence
<220> FEATURE:
<223> OTHER INFORMATION: Synthetic

<400> SEQUENCE: 89

Gly Thr Ala Ser Gly Thr Ala Ala Lys Ser Thr Leu Val Lys Ile Ser
1               5                   10                  15

Thr Arg Asn Asn Asn Ser Asn Phe Pro Trp Thr Ala Ala Ser Thr Glu
        20                  25                  30

Asp Asp Glu Glu Lys Glu Gly Thr Ser Lys Asn Asp Val Glu Val Glu
        35                  40                  45

Asn

<210> SEQ ID NO 90
<211> LENGTH: 49
<212> TYPE: PRT
<213> ORGANISM: Artificial Sequence
<220> FEATURE:
<223> OTHER INFORMATION: Synthetic

<400> SEQUENCE: 90

Gly Thr Thr Ser Gly Thr Thr Thr Thr Arg Arg Leu Met Lys Ile Tyr
1               5                   10                  15

Gly Gly Asn Asn Asn Ser Asn Phe Pro Trp Thr Ala Ala Ser Thr Glu
        20                  25                  30

Asp Asp Ala Gly Arg Gln Gly Thr Ala Thr Ala Asn Val Glu Val Glu
        35                  40                  45

Ser

<210> SEQ ID NO 91
<211> LENGTH: 49
<212> TYPE: PRT
<213> ORGANISM: Artificial Sequence
<220> FEATURE:
<223> OTHER INFORMATION: Synthetic

<400> SEQUENCE: 91
```

Gly Thr Ala Gly Gly Thr Ala Gly Met Arg Glu Leu Ala Thr Ile Tyr
1               5                   10                  15

Thr Gly Asn Asn Asn Ser Asn Phe Pro Trp Thr Ala Ala Ser Lys Lys
            20                  25                  30

Asp Asp Glu Gly Arg Glu Gly Ser Ser Thr Gly Asp Ala Asp Val Gly
        35                  40                  45

Arg

<210> SEQ ID NO 92
<211> LENGTH: 49
<212> TYPE: PRT
<213> ORGANISM: Artificial Sequence
<220> FEATURE:
<223> OTHER INFORMATION: Synthetic

<400> SEQUENCE: 92

Ser Thr Thr Gly Gly Thr Ala Asn Pro Lys Glu Leu Arg Thr Ala Ala
1               5                   10                  15

Asn His Asn Asn Asn Ser Glu Phe Pro Trp Thr Ala Ala Ser Thr Glu
            20                  25                  30

Asp Asp Glu Asp Lys Gln Gly Ala Gly Glu Ser Asn Val Ala Ile Asp
        35                  40                  45

Gly

<210> SEQ ID NO 93
<211> LENGTH: 49
<212> TYPE: PRT
<213> ORGANISM: Artificial Sequence
<220> FEATURE:
<223> OTHER INFORMATION: Synthetic

<400> SEQUENCE: 93

Gly Thr Thr Ser Gly Thr Thr Gly Thr Ser Thr Leu Arg Lys Thr Asp
1               5                   10                  15

Thr Gly Asn Asn Asn Ser Asn Phe Pro Trp Thr Ala Ala Ser Lys Gly
            20                  25                  30

Asp Asp Glu Glu Arg Glu Gly Ala Gly Thr Ala Asp Ala Ala Val Asp
        35                  40                  45

Gly

<210> SEQ ID NO 94
<211> LENGTH: 49
<212> TYPE: PRT
<213> ORGANISM: Artificial Sequence
<220> FEATURE:
<223> OTHER INFORMATION: Synthetic

<400> SEQUENCE: 94

Gly Asn Ala Gly Gly Thr Thr Asn Lys Arg Asp Leu Leu Thr Ala Tyr
1               5                   10                  15

Thr Arg Asn Asn Asn Ser Asp Phe Pro Trp Thr Ala Ala Ser Thr Lys
            20                  25                  30

Asp Asp Asp Glu Lys Gln Gly Thr Gly Lys Thr Asp Ala Asp Asn Gly
        35                  40                  45

Gly

<210> SEQ ID NO 95
<211> LENGTH: 49
<212> TYPE: PRT
<213> ORGANISM: Artificial Sequence

```
<220> FEATURE:
<223> OTHER INFORMATION: Synthetic

<400> SEQUENCE: 95

Gly Asn Ala Ser Gly Thr Thr Asp Met Lys His Leu Thr Lys Ile Ser
1               5                   10                  15

Asp Arg Asn Asn Asn Ser Asn Phe Pro Trp Pro Ala Ala Ser Thr Arg
            20                  25                  30

Asp Asp Asn Glu Arg Gln Ser Thr Arg Gly Gly Asn Ala Glu Ile Asp
        35                  40                  45

Gly

<210> SEQ ID NO 96
<211> LENGTH: 49
<212> TYPE: PRT
<213> ORGANISM: Artificial Sequence
<220> FEATURE:
<223> OTHER INFORMATION: Synthetic

<400> SEQUENCE: 96

Ser Asn Thr Gly Gly Thr Ala Asp Leu Arg Asp Leu Leu Thr Ile Pro
1               5                   10                  15

Thr Gln Asn Asn Asn Ser Glu Phe Pro Trp Thr Ala Ala Ser Lys Lys
            20                  25                  30

Asp Asp Asn Asp Arg Gln Ser Ala Lys Ala Asn Asp Val Glu Val Asp
        35                  40                  45

Arg

<210> SEQ ID NO 97
<211> LENGTH: 49
<212> TYPE: PRT
<213> ORGANISM: Artificial Sequence
<220> FEATURE:
<223> OTHER INFORMATION: Synthetic

<400> SEQUENCE: 97

Ser Thr Ala Ser Gly Thr Thr Ala Thr Gln Gln Leu Val Thr Thr Asp
1               5                   10                  15

Ser Gln Asn Asn Asn Ser Glu Phe Pro Trp Thr Ala Ala Ser Thr Arg
            20                  25                  30

Asp Asp Asn Asp Arg Glu Asn Ala Glu Gly Gly Asn Val Glu Ile Gly
        35                  40                  45

Gln

<210> SEQ ID NO 98
<211> LENGTH: 49
<212> TYPE: PRT
<213> ORGANISM: Artificial Sequence
<220> FEATURE:
<223> OTHER INFORMATION: Synthetic

<400> SEQUENCE: 98

Gly Asn Ala Gly Gly Thr Thr Ala Asn Lys Thr Leu Met Lys Ile Ala
1               5                   10                  15

Ala His Asn Asn Asn Ser Glu Phe Pro Trp Thr Ala Ala Ser Thr Arg
            20                  25                  30

Asp Asp Asp Gly Lys Gln Asp Ser Ser Ala Asp Asn Ile Glu Tyr Gly
        35                  40                  45

Lys
```

-continued

<210> SEQ ID NO 99
<211> LENGTH: 49
<212> TYPE: PRT
<213> ORGANISM: Artificial Sequence
<220> FEATURE:
<223> OTHER INFORMATION: Synthetic

<400> SEQUENCE: 99

Gly Asn Ala Gly Gly Thr Thr Gly Thr Lys Glu Leu Arg Thr Ile Ala
1               5                   10                  15

Asn Glu Asn Asn Asn Ser Asn Phe Pro Trp Thr Ala Ala Ser Thr Lys
            20                  25                  30

Asp Asp Asp Glu Lys Glu Asp Ala Lys Arg Asn Asn Val Asp Tyr Asp
        35                  40                  45

Gly

<210> SEQ ID NO 100
<211> LENGTH: 49
<212> TYPE: PRT
<213> ORGANISM: Artificial Sequence
<220> FEATURE:
<223> OTHER INFORMATION: Synthetic

<400> SEQUENCE: 100

Ser Asn Pro Ser Gly Thr Thr Gly Lys Ser Ser Leu Lys Lys Thr Ser
1               5                   10                  15

Asn Glu Asn Asn Asn Ser Asn Phe Pro Trp Thr Ala Ala Ser Lys Lys
            20                  25                  30

Asp Asp Asn Gly Lys Glu Asp Ser Arg Ala Gly Asp Ala Asp Phe Glu
        35                  40                  45

Lys

<210> SEQ ID NO 101
<211> LENGTH: 49
<212> TYPE: PRT
<213> ORGANISM: Artificial Sequence
<220> FEATURE:
<223> OTHER INFORMATION: Synthetic

<400> SEQUENCE: 101

Gly Asn Thr Ser Gly Thr Ala Ser Ile Arg Gln Leu Gln Lys Thr Pro
1               5                   10                  15

Asp Gly Asn Asn Asn Ser Lys Phe Pro Trp Thr Ala Ala Ser Lys Arg
            20                  25                  30

Asp Asp Asn Gly Arg Glu Gly Ser Thr Glu Gly Asn Ile Glu Ile Glu
        35                  40                  45

Gly

<210> SEQ ID NO 102
<211> LENGTH: 49
<212> TYPE: PRT
<213> ORGANISM: Artificial Sequence
<220> FEATURE:
<223> OTHER INFORMATION: Synthetic

<400> SEQUENCE: 102

Gly Asn Thr Gly Gly Thr Thr Thr Leu Ser Ala Leu Gly Thr Ala His
1               5                   10                  15

Thr Gln Asn Asn Asn Ser Asn Phe Pro Trp Thr Ala Ala Ser Lys Arg
            20                  25                  30

```
Asp Asp Asn Asp Lys Gln Ser Ser Thr Gly Gly Asp Thr Ala Phe Asp
        35                  40                  45

Gly

<210> SEQ ID NO 103
<211> LENGTH: 49
<212> TYPE: PRT
<213> ORGANISM: Artificial Sequence
<220> FEATURE:
<223> OTHER INFORMATION: Synthetic

<400> SEQUENCE: 103

Ser Asn Pro Ser Gly Thr Thr Thr Thr Gln Arg Leu Gln Lys Thr Asp
1               5                   10                  15

Asn Asp Asn Asn Asn Ser Asp Phe Pro Trp Pro Ala Ala Ser Thr Arg
            20                  25                  30

Asp Asp Thr Asp Arg Glu Gly Ser Thr Gly Gly Asp Ala Glu Ile Glu
        35                  40                  45

Arg

<210> SEQ ID NO 104
<211> LENGTH: 49
<212> TYPE: PRT
<213> ORGANISM: Artificial Sequence
<220> FEATURE:
<223> OTHER INFORMATION: Synthetic

<400> SEQUENCE: 104

Ser Asn Ala Ser Gly Thr Thr Thr Met Arg Lys Leu Gly Thr Ile Ser
1               5                   10                  15

Ser Gly Asn Asn Asn Ser Asn Phe Pro Trp Pro Ala Ala Ser Lys Gly
            20                  25                  30

Asp Asp Asn Glu Lys Gln Asp Ser Ser Glu Asn Asp Val Ala Asp Glu
        35                  40                  45

Arg

<210> SEQ ID NO 105
<211> LENGTH: 49
<212> TYPE: PRT
<213> ORGANISM: Artificial Sequence
<220> FEATURE:
<223> OTHER INFORMATION: Synthetic

<400> SEQUENCE: 105

Ser Thr Ala Gly Gly Thr Ala Thr Met Gln Arg Leu Met Thr Thr Asp
1               5                   10                  15

Thr Gly Asn Asn Asn Ser Asn Phe Pro Trp Thr Ala Ala Ser Thr Arg
            20                  25                  30

Asp Asp Asn Glu Arg Gln Gly Gly Glu Gly Gly Asp Ile Glu Asp Asp
        35                  40                  45

Arg

<210> SEQ ID NO 106
<211> LENGTH: 49
<212> TYPE: PRT
<213> ORGANISM: Artificial Sequence
<220> FEATURE:
<223> OTHER INFORMATION: Synthetic

<400> SEQUENCE: 106

Gly Thr Ala Gly Gly Thr Ala Thr Thr Arg Asp Leu Gln Thr Thr Asp
```

-continued

```
1               5                 10                15

Asp His Asn Asn Asn Ser Asp Phe Pro Trp Thr Ala Ala Ser Lys Lys
            20                25                30

Asp Asp Asn Gly Arg Gln Gly Gly Arg Gly Ala Asn Thr Ala Tyr Glu
            35                40                45

Gly

<210> SEQ ID NO 107
<211> LENGTH: 49
<212> TYPE: PRT
<213> ORGANISM: Artificial Sequence
<220> FEATURE:
<223> OTHER INFORMATION: Synthetic

<400> SEQUENCE: 107

Gly Thr Thr Gly Gly Thr Ala Ala Met Ser Ala Leu Arg Thr Thr Asp
1               5                 10                15

Asp Gly Asn Asn Asn Ser Lys Phe Pro Trp Pro Ala Ala Ser Lys Lys
            20                25                30

Asp Asp Glu Glu Lys Glu Asp Gly Gly Thr Ser Asn Ala Ala Ile Gly
            35                40                45

Asp

<210> SEQ ID NO 108
<211> LENGTH: 49
<212> TYPE: PRT
<213> ORGANISM: Artificial Sequence
<220> FEATURE:
<223> OTHER INFORMATION: Synthetic

<400> SEQUENCE: 108

Gly Asn Thr Ser Gly Thr Thr Thr Asn Arg Glu Leu Met Lys Ile Pro
1               5                 10                15

Asn Asp Asn Asn Asn Ser Asn Phe Pro Trp Thr Ala Ala Ser Thr Arg
            20                25                30

Asp Asp Glu Asp Lys Glu Asp Thr Gly Arg Ala Asp Val Glu Val Gly
            35                40                45

Arg

<210> SEQ ID NO 109
<211> LENGTH: 49
<212> TYPE: PRT
<213> ORGANISM: Artificial Sequence
<220> FEATURE:
<223> OTHER INFORMATION: Synthetic

<400> SEQUENCE: 109

Ser Asn Ala Gly Gly Thr Ala Asp Lys Gln Asp Leu Val Thr Ala His
1               5                 10                15

Ser Glu Asn Asn Asn Ser Asn Phe Pro Trp Thr Ala Ala Ser Lys Glu
            20                25                30

Asp Asp Asp Asp Arg Gln Gly Ala Ala Gly Gly Asp Ile Glu Val Gly
            35                40                45

Ser

<210> SEQ ID NO 110
<211> LENGTH: 49
<212> TYPE: PRT
<213> ORGANISM: Artificial Sequence
<220> FEATURE:
```

<223> OTHER INFORMATION: Synthetic

<400> SEQUENCE: 110

```
Gly Asn Ala Ser Gly Thr Ala Ala Thr His Glu Leu Leu Thr Thr His
1               5                   10                  15

Asp His Asn Asn Asn Ser Asp Phe Pro Trp Thr Ala Ala Ser Lys Arg
            20                  25                  30

Asp Asp Ala Glu Arg Glu Gly Gly Ala Lys Ser Asp Val Asp Phe Gly
        35                  40                  45

Ser
```

<210> SEQ ID NO 111
<211> LENGTH: 49
<212> TYPE: PRT
<213> ORGANISM: Artificial Sequence
<220> FEATURE:
<223> OTHER INFORMATION: Synthetic

<400> SEQUENCE: 111

```
Ser Asn Ala Ser Gly Thr Ala Asp Thr Arg His Leu Met Thr Thr Pro
1               5                   10                  15

Gly Glu Asn Asn Asn Ser Asp Phe Pro Trp Pro Ala Ala Ser Thr Gly
            20                  25                  30

Asp Asp Thr Gly Lys Gln Gly Ser Ala Thr Thr Asp Ile Glu Tyr Gly
        35                  40                  45

Glu
```

<210> SEQ ID NO 112
<211> LENGTH: 49
<212> TYPE: PRT
<213> ORGANISM: Artificial Sequence
<220> FEATURE:
<223> OTHER INFORMATION: Synthetic

<400> SEQUENCE: 112

```
Ser Asn Thr Ser Gly Thr Thr Ala Gln Ser Lys Leu Gln Lys Ile His
1               5                   10                  15

Asn Arg Asn Asn Asn Ser Asp Phe Pro Trp Thr Ala Ala Ser Thr Arg
            20                  25                  30

Asp Asp Asp Asp Arg Gln Gly Ala Glu Gly Ser Asp Val Ala Val Gly
        35                  40                  45

Asp
```

<210> SEQ ID NO 113
<211> LENGTH: 49
<212> TYPE: PRT
<213> ORGANISM: Artificial Sequence
<220> FEATURE:
<223> OTHER INFORMATION: Synthetic

<400> SEQUENCE: 113

```
Gly Asn Pro Ser Gly Thr Ala Asp Gln Arg Ala Leu Gln Lys Ile Pro
1               5                   10                  15

Thr Gly Asn Asn Asn Ser Asp Phe Pro Trp Thr Ala Ala Ser Thr Arg
            20                  25                  30

Asp Asp Thr Glu Lys Gln Gly Thr Gly Gly Ser Asp Ile Glu Ile Gly
        35                  40                  45

Gly
```

<210> SEQ ID NO 114
<211> LENGTH: 49
<212> TYPE: PRT
<213> ORGANISM: Artificial Sequence
<220> FEATURE:
<223> OTHER INFORMATION: Synthetic

<400> SEQUENCE: 114

Ser Asn Ala Ser Gly Thr Ala Gly Leu Asn Ala Leu Lys Lys Ala Tyr
1               5                   10                  15

Thr His Asn Asn Asn Ser Asp Phe Pro Trp Thr Ala Ala Ser Thr Gly
            20                  25                  30

Asp Asp Asp Glu Arg Glu Asn Ala Lys Ala Gly Asn Ala Ala Ile Asp
        35                  40                  45

Gly

<210> SEQ ID NO 115
<211> LENGTH: 49
<212> TYPE: PRT
<213> ORGANISM: Artificial Sequence
<220> FEATURE:
<223> OTHER INFORMATION: Synthetic

<400> SEQUENCE: 115

Gly Asn Pro Ser Gly Thr Thr Asn Leu Gln Arg Leu Met Lys Ile Asp
1               5                   10                  15

Asp Gln Asn Asn Asn Ser Asn Phe Pro Trp Pro Ala Ala Ser Thr Lys
            20                  25                  30

Asp Asp Glu Asp Lys Glu Ser Gly Gly Thr Ala Asp Val Ala Val Asp
        35                  40                  45

Lys

<210> SEQ ID NO 116
<211> LENGTH: 49
<212> TYPE: PRT
<213> ORGANISM: Artificial Sequence
<220> FEATURE:
<223> OTHER INFORMATION: Synthetic

<400> SEQUENCE: 116

Gly Thr Thr Ser Gly Thr Ala Ser Ile Gln Arg Leu Gln Lys Thr Tyr
1               5                   10                  15

Ala Asp Asn Asn Asn Ser Glu Phe Pro Trp Thr Ala Ala Ser Thr Lys
            20                  25                  30

Asp Asp Glu Asp Lys Glu Ser Ala Ala Gly Ser Asp Thr Glu Val Asp
        35                  40                  45

Gly

<210> SEQ ID NO 117
<211> LENGTH: 496
<212> TYPE: PRT
<213> ORGANISM: Artificial Sequence
<220> FEATURE:
<223> OTHER INFORMATION: Synthetic

<400> SEQUENCE: 117

Thr Thr Ser Thr Arg Thr Trp Ala Leu Pro Thr Tyr Asn Asn His Leu
1               5                   10                  15

Tyr Lys Gln Ile Ser Ser Gln Ser Gly Ala Ser Asn Asp Asn His Tyr
            20                  25                  30

Phe Gly Tyr Ser Thr Pro Trp Gly Tyr Phe Asp Phe Asn Arg Phe His

```
                35                    40                    45

Cys His Phe Ser Pro Arg Asp Trp Gln Arg Leu Ile Asn Asn Asn Trp
    50                    55                    60

Gly Phe Arg Pro Lys Lys Leu Ser Phe Lys Leu Phe Asn Ile Gln Val
65                    70                    75                    80

Arg Gly Val Thr Gln Asn Asp Gly Thr Thr Thr Ile Ala Asn Asn Leu
                85                    90                    95

Thr Ser Thr Val Gln Val Phe Thr Asp Ser Glu Tyr Gln Leu Pro Tyr
                100                   105                   110

Val Leu Gly Ser Ala His Gln Gly Cys Leu Pro Pro Phe Pro Ala Asp
                115                   120                   125

Val Phe Met Val Pro Gln Tyr Gly Tyr Leu Thr Leu Asn Asn Gly Ser
    130                   135                   140

Gln Ala Val Gly Arg Ser Ser Phe Tyr Cys Leu Glu Tyr Phe Pro Ser
145                   150                   155                   160

Gln Met Leu Arg Thr Gly Asn Asn Phe Gln Phe Ser Tyr Thr Phe Glu
                165                   170                   175

Asp Val Pro Phe His Ser Ser Tyr Ala His Ser Gln Ser Leu Asp Arg
                180                   185                   190

Leu Met Asn Pro Leu Ile Asp Gln Tyr Leu Tyr Tyr Leu Asn Arg Thr
                195                   200                   205

Gln Gly Thr Thr Ser Gly Thr Thr Asn Gln Ser Arg Leu Leu Phe Ser
    210                   215                   220

Gln Ala Gly Pro Gln Ser Met Ser Leu Gln Ala Arg Asn Trp Leu Pro
225                   230                   235                   240

Gly Pro Cys Tyr Arg Gln Gln Arg Leu Ser Lys Thr Ala Asn Asp Asn
                245                   250                   255

Asn Asn Ser Asn Phe Pro Trp Thr Ala Ala Ser Lys Tyr His Leu Asn
                260                   265                   270

Gly Arg Asp Ser Leu Val Asn Pro Gly Pro Ala Met Ala Ser His Lys
                275                   280                   285

Asp Asp Glu Glu Lys Phe Phe Pro Met His Gly Asn Leu Ile Phe Gly
    290                   295                   300

Lys Glu Gly Thr Thr Ala Ser Asn Ala Glu Leu Asp Asn Val Met Ile
305                   310                   315                   320

Thr Asp Glu Glu Glu Ile Arg Thr Thr Asn Pro Val Ala Thr Glu Gln
                325                   330                   335

Tyr Gly Thr Val Ala Asn Asn Leu Gln Ser Ser Asn Thr Ala Pro Thr
                340                   345                   350

Thr Gly Thr Val Asn His Gln Gly Ala Leu Pro Gly Met Val Trp Gln
                355                   360                   365

Asp Arg Asp Val Tyr Leu Gln Gly Pro Ile Trp Ala Lys Ile Pro His
    370                   375                   380

Thr Asp Gly His Phe His Pro Ser Pro Leu Met Gly Gly Phe Gly Leu
385                   390                   395                   400

Lys His Pro Pro Pro Gln Ile Met Ile Lys Asn Thr Pro Val Pro Ala
                405                   410                   415

Asn Pro Pro Thr Thr Phe Ser Pro Ala Lys Phe Ala Ser Phe Ile Thr
                420                   425                   430

Gln Tyr Ser Thr Gly Gln Val Ser Val Glu Ile Glu Trp Glu Leu Gln
                435                   440                   445

Lys Glu Asn Ser Lys Arg Trp Asn Pro Glu Ile Gln Tyr Thr Ser Asn
    450                   455                   460
```

```
Tyr Asn Lys Ser Val Asn Val Asp Phe Thr Val Asp Thr Asn Gly Val
465                 470                 475                 480

Tyr Ser Glu Pro Arg Pro Ile Gly Thr Arg Tyr Leu Thr Arg Asn Leu
                485                 490                 495

<210> SEQ ID NO 118
<211> LENGTH: 1611
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t

<400> SEQUENCE: 118
accaccagca ccagaacctg ggccctgccc acttacaaca accatctcta caagcaaatc        60
tccagccaat caggagcttc aaacgacaac cactactttg ctacagcac ccccttggggg       120 vvmdasctat tttgactta acagattcca ctgccacttc tcaccacgtg actggcagcg       180
actcattaac aacaactggg gattccggcc caagaaactc agcttcaagc tcttcaacat       240
ccaagttaga ggggtcacgc agaacgatgg cacgacgact attgccaata accttaccag       300
cacggttcaa gtgtttacgg actcggagta tcagctcccg tacgtgctcg ggtcggcgca       360
ccaaggctgt ctcccgccgt ttccagcgga cgtcttcatg gtccctcagt atggatacct       420
caccctgaac aacggaagtc aagcggtggg acgctcatcc ttttactgcc tggagtactt       480
cccttcgcag atgctaagga ctggaaataa cttccaattc agctatacct tcgaggatgt       540
accttttcac agcagctacg ctcacagcca gagtttggat cgcttgatga atcctcttat       600
tgatcagtat ctgtactacc tgaacagaac gcaaggaaca acctctggaa caaccaacca       660
atcacggngc amcvcnrgcr ccrvcmhsmr svvsctgctt tttagccagg ctgggcctca       720
gtctatgtct ttgcaggcca gaaattggct acctvngggg ccctgctacc ggcaacagag       780
actttcaaag actgctaacg acaacaacaa cagtaacmar ycbmcrvcsr srstttcctt       840
ggacagcggc cagcaaatat catctcaatg gccgcgactc gctggtgaat ccammggacc       900
agctatggcc agtcacaagg acgatgaaga aaaattttttc cctatgcacg gcaatrrrms       960
grsrctaata tttggcaaag aagggacaac ggcaagtaac gcagaattag ataatgtaat      1020
gattsrrcrs crvsrvrvcr trycmsdwcr svrsacggat gaagaagaga ttcgtaccac      1080
caatcctgtg gcaacagagc agtatggaac tgtggcaaat aacttgcaga gctcaaatac      1140
agctcccacg actggaactg tcaatcatca ggggrvsvvs mrsrvcvvsd hvvsrnsvms      1200
gccttacctg gcatggtgtg gcaagatcgt gacgtctacc ttcaaggacc tatctgggca      1260
aagattcctc acacggatgg acactttcat ccttctcctc tgatgggagg ctttggactg      1320
aaacatccgc ctcctcaaat catgatcaaa aatactccgg taccggcaaa tcctccgacg      1380
actttcagcc cggccaagtt tgcttcattt atcactcagt actccactgg acaggtcagc      1440
gtggaaattg agtgggagct acagaaagaa aacagcaaac gttggaatcc agagattcag      1500
```

```
tacacttcca actacaacaa gtctgttaat gtggacttta ctgtagacac taatggtgtt    1560
tatagtgaac ctcgccctat tggaacccgg tatctcacac gaaacttgtg a             1611
```

```
<210> SEQ ID NO 119
<211> LENGTH: 1140
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (1064)..(1064)
<223> OTHER INFORMATION: n is a, c, g, or t

<400> SEQUENCE: 119
accaccagca ccagaacctg ggccctgccc acttacaaca accatctcta caagcaaatc      60
tccagcvvmd caggagctas caacgacaac cactactttg gctacagcac cccttggggg     120
tattttgact ttaacagatt ccactgccac ttctcaccac gtgactggca gcgactcatt     180
aacaacaact ggggattccg gcccaagaaa ctcagcttca agctcttcaa catccaagtt     240
agaggggtca cgcagaacga tggcacgacg actattgcca ataaccttac cagcacggtt     300
caagtgttta cggactcgga gtatcagctc ccgtacgtgc tcgggtcggc gcaccaaggc     360
tgtctcccgc cgtttccagc ggacgtcttc atggtccctc agtatggata cctcaccctg     420
aacaacggaa gtcaagcggt gggacgctca tcctttact gcctggagta cttcccttcg      480
cagatgctaa ggactggaaa taacttccaa ttcagctata ccttcgagga tgtacctttt     540
cacagcagct acgctcacag ccagagtttg gatcgcttga tgaatcctct tattgatcag     600
tatctgtact acctgaacag aacgcaargc amcvcnrgcg gaacarccrv cmhsmrsvvs     660
ctgvngttta gccaggctgg gcctcagtct atgtctttgc aggccagaaa ttggctacct     720
gggccctgct accggcaaca gagactttca amarycbmcr vcsrsaacaa caacagtras     780
tttccttggm cagcggccag camatatcat ctcaatggcc gcgactcgct ggtgaatcca     840
ggaccagcta tggccagtca crrggacgat rmsgrsarat ttttccctat gcacggcaat     900
ctaatatttg gcaaasaarr crscrvsrva rvcratrycg msdwcgrsvr sgtaatgatt     960
acggatgaag aagagattcg taccaccaat cctgtggcaa cagagcagta tggaactgtg    1020
gcaaataact tgcagrvsvv smrsrvcvvs cccacgdhtv vsrnsgtcvm scatcagggg    1080
gccttacctg gcatggtgtg gcaagatcgt gacgtctacc ttcaaggacc tatctgggca    1140
```

```
<210> SEQ ID NO 120
<211> LENGTH: 620
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (263)..(264)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
```

<220> FEATURE:
<221> NAME/KEY: misc_feature
<222> LOCATION: (450)..(453)
<223> OTHER INFORMATION: Xaa can be any naturally occurring amino acid
<220> FEATURE:
<221> NAME/KEY: misc_feature
<222> LOCATION: (456)..(460)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (491)..(495)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (508)..(508)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid
<220> FEATURE:
<221> NAME/KEY: misc_feature
<222> LOCATION: (531)..(533)
<223> OTHER INFORMATION: Xaa can be any naturally occurring amino acid
<220> FEATURE:
<221> NAME/KEY: misc_feature
<222> LOCATION: (546)..(557)
<223> OTHER INFORMATION: Xaa can be any naturally occurring amino acid
<220> FEATURE:
<221> NAME/KEY: misc_feature
<222> LOCATION: (586)..(590)
<223> OTHER INFORMATION: Xaa can be any naturally occurring amino acid
<220> FEATURE:
<221> NAME/KEY: misc_feature
<222> LOCATION: (593)..(595)
<223> OTHER INFORMATION: Xaa can be any naturally occurring amino acid
<220> FEATURE:
<221> NAME/KEY: misc_feature
<222> LOCATION: (597)..(597)
<223> OTHER INFORMATION: Xaa can be any naturally occurring amino acid

<400> SEQUENCE: 120

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

-continued

```
Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Xaa Xaa Gly Ala Xaa Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Xaa Xaa Xaa Xaa Gly Thr Xaa Xaa Xaa Xaa Xaa Leu Xaa Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Xaa Xaa Xaa Xaa Xaa Asn
                485                 490                 495

Asn Asn Ser Xaa Phe Pro Trp Xaa Ala Ala Ser Xaa Tyr His Leu Asn
                500                 505                 510

Gly Arg Asp Ser Leu Val Asn Pro Gly Pro Ala Met Ala Ser His Xaa
                515                 520                 525

Asp Asp Xaa Xaa Xaa Phe Phe Pro Met His Gly Asn Leu Ile Phe Gly
    530                 535                 540

Lys Xaa Xaa Xaa Xaa Xaa Xaa Xaa Xaa Xaa Xaa Xaa Xaa Val Met Ile
```

-continued

```
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Xaa Xaa Xaa Xaa Xaa Pro Thr
                580                 585                 590

Xaa Xaa Xaa Val Xaa His Gln Gly Ala Leu Pro Gly Met Val Trp Gln
            595                 600                 605

Asp Arg Asp Val Tyr Leu Gln Gly Pro Ile Trp Ala
        610                 615                 620

<210> SEQ ID NO 121
<211> LENGTH: 349
<212> TYPE: PRT
<213> ORGANISM: Artificial Sequence
<220> FEATURE:
<223> OTHER INFORMATION: Synthetic

<400> SEQUENCE: 121

Gln Ile Ser Ser Gln Asn Lys Thr Ser Arg His Pro Asp Glu Ala Gly
1               5                   10                  15

Ser Thr Ala Gly Ala Ser Thr Asn Asp Asn Leu Asn Arg Thr Gln Gly
                20                  25                  30

Ser Thr Asn Thr Pro Ala Ser Gly Gly Thr Thr Ala Asn Thr Ser Asp
            35                  40                  45

Ala Gly Gln His Pro Leu Lys Asn Thr Met Ile Ser Gln His Arg Lys
        50                  55                  60

Asn Arg Lys Asn Thr Ser Gln His Pro Glu Asp Ala Gly Leu Leu Lys
65                  70                  75                  80

Thr Arg Met Gln Pro Glu Ala Gly Val Phe Ser Gln Arg Gln Gln Arg
                85                  90                  95

Leu Ser Lys Thr Thr Ile Ala Val Ala Pro His Asp Ser Tyr Asn Thr
            100                 105                 110

Ser Asp Ala Gly Asp Glu Gly Gln His Arg Asn Asn Asn Ser Asn Lys
        115                 120                 125

Glu Asp Phe Pro Trp Thr Pro Ala Ala Ser Lys Thr Tyr His Leu Asn
        130                 135                 140

Gly Arg Asp Ser Leu Val Asn Pro Gly Pro Ala Met Ala Ser His Lys
145                 150                 155                 160

Arg Glu Gly Asp Asp Glu Thr Lys Asn Ala Asp Glu Asp Gly Lys Arg
                165                 170                 175

Phe Phe Pro Met His Gly Asn Leu Ile Phe Gly Lys Glu Gln Gly Asn
            180                 185                 190

Ser Asp Thr Ser Gly Ala Thr Lys Asn Arg Ser Glu Asp Ala Gly Ala
        195                 200                 205

Lys Thr Arg Glu Gly Ser Asn Thr Asp Ala Gly Asn Asp Ala Thr Ile
        210                 215                 220

Val Glu Ala Asp Leu Asn Ile Asp Val Tyr Phe Asp Glu Gly Asn Lys
225                 230                 235                 240

Arg Ser Gln His Glu Asp Gly Val Met Ile Val Ala Asn Asn Leu Gln
                245                 250                 255

Ser Lys Asn Thr Arg Glu Asp Ala Gly Ser Lys Asn Thr Arg Gln His
            260                 265                 270

Pro Glu Asp Ala Gly Asn Gln His Arg Lys Ser Thr Asn Ser Asp Ala
        275                 280                 285

Gly Ala Lys Asn Thr Arg Ser Gln His Pro Glu Asp Gly Pro Thr Thr
```

```
              290                    295                    300

Asn Ile Asp Ala Val Tyr Ser Phe Gly Lys Asn Thr Arg Ser Gln His
305                    310                    315                    320

Pro Glu Asp Ala Thr Lys Asn Arg Ser Met Ile Glu Asp Ala Gly Val
                   325                    330                    335

Val Asn Thr Lys Pro Gln His Ala Glu Asp His Gln Gly
                   340                    345

<210> SEQ ID NO 122
<211> LENGTH: 736
<212> TYPE: PRT
<213> ORGANISM: Artificial Sequence
<220> FEATURE:
<223> OTHER INFORMATION: Synthetic

<400> SEQUENCE: 122

Met Ala Ala Asp Gly Tyr Leu Pro Asp Trp Leu Glu Asp Asn Leu Ser
1                   5                   10                   15

Glu Gly Ile Arg Glu Trp Trp Ala Leu Lys Pro Gly Val Pro Gln Pro
                   20                   25                   30

Lys Ala Asn Gln Gln His Gln Asp Asn Arg Arg Gly Leu Val Leu Pro
              35                   40                   45

Gly Tyr Lys Tyr Leu Gly Pro Gly Asn Gly Leu Asp Lys Gly Glu Pro
         50                   55                   60

Val Asn Glu Ala Asp Ala Ala Ala Leu Glu His Asp Lys Ala Tyr Asp
65                   70                   75                   80

Gln Gln Leu Lys Ala Gly Asp Asn Pro Tyr Leu Lys Tyr Asn His Ala
                   85                   90                   95

Asp Ala Glu Phe Gln Glu Arg Leu Gln Glu Asp Thr Ser Phe Gly Gly
              100                  105                  110

Asn Leu Gly Arg Ala Val Phe Gln Ala Lys Lys Arg Ile Leu Glu Pro
         115                  120                  125

Leu Gly Leu Val Glu Glu Ala Ala Lys Thr Ala Pro Gly Lys Lys Arg
         130                  135                  140

Pro Val Asp Gln Ser Pro Gln Glu Pro Asp Ser Ser Ser Gly Val Gly
145                  150                  155                  160

Lys Ser Gly Lys Gln Pro Ala Arg Lys Arg Leu Asn Phe Gly Gln Thr
              165                  170                  175

Gly Asp Ser Glu Ser Val Pro Asp Pro Gln Pro Leu Gly Glu Pro Pro
              180                  185                  190

Ala Ala Pro Thr Ser Leu Gly Ser Asn Thr Met Ala Ser Gly Gly Gly
         195                  200                  205

Ala Pro Met Ala Asp Asn Asn Glu Gly Ala Asp Gly Val Gly Asn Ser
         210                  215                  220

Ser Gly Asn Trp His Cys Asp Ser Gln Trp Leu Gly Asp Arg Val Ile
225                  230                  235                  240

Thr Thr Ser Thr Arg Thr Trp Ala Leu Pro Thr Tyr Asn Asn His Leu
                   245                  250                  255

Tyr Lys Gln Ile Ser Ser Gln Ser Gly Ala Ser Asn Asp Asn His Tyr
              260                  265                  270

Phe Gly Tyr Ser Thr Pro Trp Gly Tyr Phe Asp Phe Asn Arg Phe His
         275                  280                  285

Cys His Phe Ser Pro Arg Asp Trp Gln Arg Leu Ile Asn Asn Asn Trp
         290                  295                  300

Gly Phe Arg Pro Lys Lys Leu Ser Phe Lys Leu Phe Asn Ile Gln Val
```

-continued

```
305                310                315                320

Lys Glu Val Thr Gln Asn Asp Gly Thr Thr Thr Ile Ala Asn Asn Leu
             325                330                335

Thr Ser Thr Val Gln Val Phe Thr Asp Ser Glu Tyr Gln Leu Pro Tyr
             340                345                350

Val Leu Gly Ser Ala His Gln Gly Cys Leu Pro Pro Phe Pro Ala Asp
             355                360                365

Val Phe Met Val Pro Gln Tyr Gly Tyr Leu Thr Leu Asn Asn Gly Ser
             370                375                380

Gln Ala Val Gly Arg Ser Ser Phe Tyr Cys Leu Glu Tyr Phe Pro Ser
385                390                395                400

Gln Met Leu Arg Thr Gly Asn Asn Phe Gln Phe Ser Tyr Thr Phe Glu
             405                410                415

Asp Val Pro Phe His Ser Ser Tyr Ala His Ser Gln Ser Leu Asp Arg
             420                425                430

Leu Met Asn Pro Leu Ile Asp Gln Tyr Leu Tyr Tyr Leu Asn Arg Thr
             435                440                445

Gln Gly Thr Thr Ser Gly Thr Thr Asn Gln Ser Arg Leu Leu Phe Ser
             450                455                460

Gln Ala Gly Pro Gln Ser Met Ser Leu Gln Ala Arg Asn Trp Leu Pro
465                470                475                480

Gly Pro Cys Tyr Arg Gln Gln Arg Leu Ser Lys Thr Ala Asn Asp Asn
             485                490                495

Asn Asn Ser Asn Phe Pro Trp Thr Ala Ala Ser Lys Tyr His Leu Asn
             500                505                510

Gly Arg Asp Ser Leu Val Asn Pro Gly Pro Ala Met Ala Ser His Lys
             515                520                525

Asp Asp Glu Glu Lys Phe Phe Pro Met His Gly Asn Leu Ile Phe Gly
             530                535                540

Lys Glu Gly Thr Thr Ala Ser Asn Ala Glu Leu Asp Asn Val Met Ile
545                550                555                560

Thr Asp Glu Glu Glu Ile Arg Thr Thr Asn Pro Val Ala Thr Glu Gln
             565                570                575

Tyr Gly Thr Val Ala Asn Asn Leu Gln Ser Ser Asn Thr Ala Pro Thr
             580                585                590

Thr Arg Thr Val Asn Asp Gln Gly Ala Leu Pro Gly Met Val Trp Gln
             595                600                605

Asp Arg Asp Val Tyr Leu Gln Gly Pro Ile Trp Ala Lys Ile Pro His
             610                615                620

Thr Asp Gly His Phe His Pro Ser Pro Leu Met Gly Gly Phe Gly Leu
625                630                635                640

Lys His Pro Pro Pro Gln Ile Met Ile Lys Asn Thr Pro Val Pro Ala
             645                650                655

Asn Pro Pro Thr Thr Phe Ser Pro Ala Lys Phe Ala Ser Phe Ile Thr
             660                665                670

Gln Tyr Ser Thr Gly Gln Val Ser Val Glu Ile Glu Trp Glu Leu Gln
             675                680                685

Lys Glu Asn Ser Lys Arg Trp Asn Pro Glu Ile Gln Tyr Thr Ser Asn
             690                695                700

Tyr Asn Lys Ser Val Asn Val Asp Phe Thr Val Asp Thr Asn Gly Val
705                710                715                720

Tyr Ser Glu Pro Arg Pro Ile Gly Thr Arg Tyr Leu Thr Arg Asn Leu
             725                730                735
```

-continued

<210> SEQ ID NO 123
<211> LENGTH: 736
<212> TYPE: PRT
<213> ORGANISM: Artificial Sequence
<220> FEATURE:
<223> OTHER INFORMATION: Synthetic

<400> SEQUENCE: 123

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

```
Val Phe Met Val Pro Gln Tyr Gly Tyr Leu Thr Leu Asn Asn Gly Ser
    370             375             380

Gln Ala Val Gly Arg Ser Ser Phe Tyr Cys Leu Glu Tyr Phe Pro Ser
385             390             395             400

Gln Met Leu Arg Thr Gly Asn Asn Phe Gln Phe Ser Tyr Thr Phe Glu
            405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Asn Arg Thr
        435             440             445

Gln Ser Thr Pro Gly Gly Thr Thr Gly Thr Asn Gly Leu Lys Phe Ser
    450             455             460

Gln Ala Gly Pro Gln Ser Met Ser Leu Gln Ala Arg Asn Trp Leu Pro
465             470             475             480

Gly Pro Cys Tyr Arg Gln Gln Arg Leu Ser Lys Ile Pro Ser Gln Asn
            485             490             495

Asn Asn Ser Asn Phe Pro Trp Thr Ala Ala Ser Lys Tyr His Leu Asn
            500             505             510

Gly Arg Asp Ser Leu Val Asn Pro Gly Pro Ala Met Ala Ser His Lys
            515             520             525

Asp Asp Asp Asp Arg Phe Phe Pro Met His Gly Asn Leu Ile Phe Gly
    530             535             540

Lys Gln Gly Ala Gly Arg Asp Asn Thr Glu Tyr Asp His Val Met Ile
545             550             555             560

Thr Asp Glu Glu Glu Ile Arg Thr Thr Asn Pro Val Ala Thr Glu Gln
            565             570             575

Tyr Gly Thr Val Ala Asn Asn Leu Gln Ser Ser Asn Thr Ala Pro Thr
            580             585             590

Thr Arg Thr Val Asn Asp Gln Gly Ala Leu Pro Gly Met Val Trp Gln
        595             600             605

Asp Arg Asp Val Tyr Leu Gln Gly Pro Ile Trp Ala Lys Ile Pro His
    610             615             620

Thr Asp Gly His Phe His Pro Ser Pro Leu Met Gly Gly Phe Gly Leu
625             630             635             640

Lys His Pro Pro Pro Gln Ile Met Ile Lys Asn Thr Pro Val Pro Ala
            645             650             655

Asn Pro Pro Thr Thr Phe Ser Pro Ala Lys Phe Ala Ser Phe Ile Thr
            660             665             670

Gln Tyr Ser Thr Gly Gln Val Ser Val Glu Ile Glu Trp Glu Leu Gln
    675             680             685

Lys Glu Asn Ser Lys Arg Trp Asn Pro Glu Ile Gln Tyr Thr Ser Asn
    690             695             700

Tyr Asn Lys Ser Val Asn Val Asp Phe Thr Val Asp Thr Asn Gly Val
705             710             715             720

Tyr Ser Glu Pro Arg Pro Ile Gly Thr Arg Tyr Leu Thr Arg Asn Leu
            725             730             735
```

```
<210> SEQ ID NO 124
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

-continued

```
<222> LOCATION: (1)..(4)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 124

Xaa Xaa Xaa Xaa Asn Asn Asn Ser Asn Phe Pro Trp Thr Ala Ala Ser
1               5                   10                  15

Xaa
```

1

AAV3B VARIANTS THAT TARGET HEPATOCYTES AND EVADE THE HUMORAL IMMUNE RESPONSE

RELATED APPLICATIONS

This application is a national stage filing under 35 U.S.C. § 371 of International Patent Application Serial No. PCT/US2020/062113, filed Nov. 24, 2020, which claims the benefit under 35 U.S.C. § 119(e) of the filing date of U.S. Provisional Application Ser. No. 62/940,167, filed Nov. 25, 2019, the entire contents of each of which are incorporated herein by reference in their entirety.

GOVERNMENT SUPPORT

The present disclosure was made with government support under Grant No. HL097088 awarded by the National Institutes of Health. The government has certain rights in the invention.

REFERENCE TO A SEQUENCE LISTING SUBMITTED AS A TEXT FILE

This Application contains a Sequence Listing which has been submitted in ASCII format via EFS-Web and is hereby incorporated by reference in its entirety. Said ASCII copy, created on Apr. 29, 2022 is named U119670049US01-SEQ-EPG and is 97,063 bytes in size.

BACKGROUND

Recombinant adeno associated virus (rAAV) vectors are among the most promising tools for in vivo human gene therapy, as demonstrated by an increasing number of clinical trials as well as treatment approvals being reported worldwide[1]. Their favorable safety profile (especially at lower vector doses) due to the episomal localization of the therapeutic gene (non-integrating vector), minimal issues of insertional mutagenesis[2], and lack of pathogenicity in transduced cells make these small virions the gene delivery vectors of choice. The ability of rAAV vectors to transduce long lived non-dividing cells such as myocytes or hepatocytes also makes them ideal for sustained expression of transgenes, which would otherwise get diluted upon cell division. Clinical translation of rAAV therapy has so far been successfully applied for hereditary blindness (Luxturna®), neuromuscular disorders (Zolgensma®), and coagulation disorders (hemophilia B), among others[3-5].

Adeno-associated virus (AAV) is a single-stranded DNA virus belonging to the Parvoviridae family (Muzyczka and Berns, 2001). AAV-derived vectors are promising tools for human gene therapy applications because of their absence of pathogenicity, low immunogenicity, episomal localization and stable transgene expression. However, significant limitations to the clinical use of AAV are its promiscuity and its susceptibility to neutralization by human antibodies (Jeune et al., 2013). Both of these limitations are determined by nature of the amino acid residues exposed at the surface of the capsid. Therefore, major efforts aiming at developing useful and effective gene therapy vectors have been devoted to obtaining and studying capsid variants (Wu et al., 2006). The first approach was to study naturally occurring AAV isolates. So far, 13 serotypes have been formally characterized and hundreds of variant isolates have been sequenced. Additional capsid variation has been investigated through the generation of mosaics (viral particles made of capsid proteins from more than one serotype) (Hauck et al., 2003; Stachler and Bartlett, 2006; Gigout et al., 2005), chimeras (capsid proteins with domains from various origins) (Shen et al., 2007), and various substitutional or insertional mutants (Wu et al., 2000). However, the most significant advances are expected to result from directed evolution approaches through the development of capsid libraries.

The state of the art method for randomizing an AAV capsid-encoding genetic sequence was until recently error-prone polymerase chain reaction (PCR), which introduced randomly dispersed mutations throughout the roughly 730 amino acids that constitute the AAV capsid sequence. However, the error-prone PCR technique suffered from two key problems. First, random mutagenesis often installed mutations that were deleterious to capsid function, as only 0.01-1% of mutations were typically beneficial (see, e.g., Romero & Arnold (2009), Nat Rev Mol Cell Biol 10(12): 866-876 and Guo, Choe & Loeb (2004), Proc Natl Acad Sci USA 101(25): 9205-9210.). Second, the sheer number of PCR clones that needed to be generated to cover all combinations of multiple mutations within a single capsid by far exceeded the technical capabilities of the skilled artisan. For instance, it has been calculated that, to comprehensively randomize five residues within a 414 base pair fragment of the AAV2 capsid VP1 gene, an AAV library would have to comprise nearly $10^{11}$ different clones to cover a single mutation at each site (see Maersch et al. (2010), Virology 397(1): 167-175).

The various strategies to generate capsid libraries that have been developed so far all suffer from sequence bias or limited diversity. Random display peptide libraries (Govindasamy et al., 2006) are limited to an insertion at one particular capsid location. Libraries generated using error-prone polymerase chain reaction (PCR) contain a very small fraction of gene variants encoding proteins that can fold properly and assemble into a functional capsid, due to the randomness of the mutations. DNA shuffling and staggered extension processes are more efficient because they recombine naturally-occurring parental sequences and therefore are more likely to generate actual capsid variants. However, they can only recombine blocks of DNA as opposed to single nucleotide positions, which results in sequence bias (parental polymorphisms will tend to cluster together instead of being randomly distributed).

SUMMARY OF THE INVENTION

The present disclosure provides adeno-associated virus (AAV) capsid variants and virions comprising capsid variants that exhibit enhanced transduction in hepatocytes. In some aspects, these capsid variants have reduced seroreactivity, and may be capable of evading neutralization by host antibodies. In some aspects, the present disclosure provides modified capsids of serotype 3B, also known as modified AAV3B capsids or AAV3B capsid variants.

In some aspects, the present disclosure provides the AAV3B-DE5 capsid variant, or "DE5." AAV3B-DE5 contains 24 amino acid substitutions compared with wild-type AAV3B, distributed among all five variable regions of the capsid, with strong selective pressure on variable regions 4, 5, and 6 (VR-IV, VR-V and VR-VI).

The present disclosure is based, at least in part, on the rational generation of AAV capsid variant libraries through the introduction of motifs of novel mutations in the native capsid through mutagenesis and directed evolution. The present disclosure is further based on the screening of variants from amongst these libraries. The capsid variant DE5 was undetectable in the original AAV library but gained a selective advantage upon in vitro passaging in human hepatocarcinoma spheroid cultures. According to the present disclosure, molecular evolution using a combinatorial library platform has generated capsid variants with high hepatocyte tropism and enhanced evasion of pre-existing AAV neutralizing antibodies.

The development of next-generation rAAV viral particles, or virions, may dramatically reduce the number of viral particles needed for a conventional gene therapy regimen. In addition to having improved transduction efficiencies for various mammalian cells, the rAAV virions prepared as described herein may be more stable, less immunogenic, and/or can be produced at much lower cost, or in a higher titer, than an equivalent wild type viral vector prepared in conventional fashion.

In the practice of the present disclosure, native amino acids normally present in the sequence of a viral capsid protein, such as a wild-type capsid of serotype 3B, may be substituted by one or more non-native amino acids, including substitutions of one or more amino acids not normally present at a particular residue in the corresponding wild-type protein. In some embodiments, the amino acid substitutions in the disclosed capsid variants may be epistatic (interacting) with respect to one another. These amino acid substitutions may act synergistically on capsid binding and transduction behavior. In some embodiments, the amino acid substitutions comprise one or more motifs.

In some embodiments, the amino acid substitutions in the disclosed capsid variants confer upon virions comprising these variants an enhanced ability to evade neutralizing antibodies of the host immune system. In some embodiments, the disclosed virions have reduced seroreactivity. In some embodiments, the disclosed virions are able to evade the humoral immune response, e.g., neutralizing antibodies, of a subject following their delivery into the subject. In particular embodiments, the subject is mammalian. The subject may be human. The subject may be a non-human primate.

Wild-type AAV is a small (~26 nm), non-enveloped parvovirus. It packages a linear single-stranded DNA genome (~4.7 kb), encoding genes necessary for replication (rep) and the viral capsid (cap), flanked by palindromic inverted terminal repeats (ITRs). Except for the ITRs which are essential, much of the viral DNA genome can be omitted for the purpose of transgene packaging and delivery, allowing for insertion of approximately 4.7 kb of foreign DNA, which altogether forms the transgene expression cassette[6]. In some cases, a self-complementary single strand duplex DNA can be packaged[7], although this reduces the transgene capacity to less than half, and increases the risk of immune response[8].

There are several challenges that impede the successful and broad use of rAAV gene therapy. The first major limitation to systemic or intramuscular administration of AAV is the presence of pre-existing neutralizing antibodies (NAb) against the vector capsid that can block cellular entry[9]. A majority of the human population are seropositive for AAV, mostly due to previous subclinical exposure to the wild-type virus[10]. This is a major exclusion criterion for prospective patients, as even very low titers of NAb in circulation can prevent vector entry and significantly limit effective gene transfer to the target organ. Pre-existing anti-AAV NAb do not affect rAAV injection into immune privileged sites such as the eye or brain. Luxturna® (voretigene neparvovec-rzyl), the FDA approved drug for treating inherited retinal disorders, can be successfully delivered into the eye using AAV serotype 2, which is seroprevalent in 40-70% of the human population[10-12]. The impact of low titer NAb (<1:5), particularly on systemic gene transfer is not accurately known[13-15]. Using a different serotype is complicated because a pattern of cross reactivity commonly occurs between variants, such as between AAV2, AAV5 and AAV8[16], or AAV1 and AAV6[17], depending on the degree of homology between capsid protein sequences.

A second limitation is transduction efficiency of target cells. Based on specific receptor interaction and post-entry mechanisms, AAV serotypes differ in cell tropism as well as transduction efficiency in the cell type of choice[18]. A major challenge to gene therapy is that the functional gene may not transduce the target tissue in high enough numbers to provide therapeutic benefit. Increasing the rAAV dose in this case is not always effective, as a high viral load can induce detrimental capsid specific T cell immune responses to the transduced cell[14-19].

These limitations cannot adequately be addressed by the current limited repertoire of naturally occurring AAV serotypes, and the isolation and characterization of novel variants is time consuming. The nature of exposed amino acid residues on the capsid surface largely determines receptor attachment, tissue transduction, and antigenicity[20]. Therefore, the development of engineered AAV vectors designed either by rational modification of specific amino acids (rational mutagenesis), or in vitro or in vivo selection in the cell type of choice (directed evolution) is an attractive alternative reported by us and others[21, 22]. These novel rAAV capsid vectors based on different serotypes have been shown to be superior at transducing the cell type of interest and in some cases, evading pre-existing NAb in the host[23-26].

Rationally-generated AAV capsid libraries containing modified AAV capsids based on serotype 3B have been recently described. See International Patent Publication No. WO 2017/070476, published on Apr. 27, 2017, herein incorporated by reference. AAV3B capsid variants containing various combinations of mutations in the surface-exposed Y, S, and T residues have been generated, and an S633V+T492V mutant (AAV3B.ST, or AAV3-ST) was identified to possess enhanced capacity to transduce primary human hepatocytes in vitro. See Ling, C, et al., *Mol Ther.* 2014; 22: S2, incorporated herein by reference. Previous studies have shown that systemically delivered AAV3B-ST performed better than AAV5, AAV8, AAV9 and wt AAV3B in a human liver xenograft mouse model as well as non-human primate livers[33, 43, 44]. Another engineered chimeric AAV3B capsid variant, LK03, which was derived from an AAV shuffled library, is closely related to wt AAV3B, with only eight amino acid changes. LK03 (or AAV3-LK03) has shown strong tropism for human hepatocytes in humanized mouse livers[23], and is currently being evaluated in clinical trials for hemophilia A gene therapy (NCT03003533). While AAV8 and AAV5 serotypes are used for in several clinical trials for hepatic gene transfer, emerging data in non-human primates and in "humanized" chimeric liver mice engrafted with human hepatocytes indicate that engineered vectors on the AAV3B backbone show superior transduction efficiencies in human liver[23, 33, 44].

Unlike what would be expected from error-prone PCR, the novel mutations of the capsid variants of the present disclosure were not randomly or arbitrarily selected. In the present disclosure, rational mutagenesis and directed evolution strategies were combined to select for engineered AAV vectors derived from the AAV3B capsid backbone. In vitro, the presently disclosed engineered variants show improved tropism for human hepatocytes as compared to wild type (wt) AAV3B, along with AAV3B variants AAV3-ST and LK03. In vivo, the presently disclosed variants show improved human hepatocyte transduction in a liver chimeric mouse model. Furthermore, the disclosed variants exhibit reduced seroreactivity to pre-existing NAb from both pooled human IVIg, as well as in individual serum samples tested from a hundred healthy human donors. These variants exhibit such reduced seroreactivity relative to, e.g., wild-type AAV3B.

Certain embodiments of the modified AAV capsids and AAV virions of the present disclosure include the second nucleotide sequence encoding an AAV Cap protein that differs from wildtype serotype 3 VP1 capsid protein at least at one amino position. The at least one amino acid position that differs is preferably in a variable region (VR), and may be in variable regions 1, 4, 5, 6, 7, or 8 (VR-I, VR-IV, VR-V, VR-VI, VR-VII, VR-VIII) and combinations thereof. See FIG. 11.

Certain aspects of the modified AAV capsids and AAV virions of the present disclosure include VR-I encoding amino acid sequence $SX_1GAX_2$ where $X_1$ is independently Q or A and $X_2$ is independently T or S. In certain embodiments, $X_1$ is A and $X_2$ is S.

The present disclosure provides variant recombinant adeno-associated virus (rAAV) serotype 3B (AAV3B) capsid protein comprising any of the following sets of sequences and/or substitutions in the wild-type of AAV3B VP1 sequence of SEQ ID NO: 1. Certain aspects of the modified AAV capsids and AAV virions of the present disclosure include VR-IV encoding amino acid sequence $X_3TX_4X_5GTTX_6X_7X_8X_9LX_{10}$ where $X_3$ is independently G or S; $X_4$ is independently T, P or A; $X_5$ is independently S or G; $X_6$ is independently N or G; $X_7$ is independently Q or T; $X_8$ is independently S or N; $X_9$ is independently R, T or G; and $X_{10}$ is independently L, K or R. In certain embodiments, $X_3$ is S; $X_4$ is P; $X_5$ is G; $X_6$ is G; $X_7$ is T; $X_8$ is N; $X_9$ is G; and $X_{10}$ is K. In some embodiments, the VR-IV encodes the sequence $STX_4X_5GTTGTX_8X_9LX_{10}$ (SEQ ID NO: 7), where $X_4$ is independently P or A; $X_5$ is independently S or G; $X_8$ is independently S or N; $X_9$ is independently T or G; and $X_{10}$ is independently K or R. In certain embodiments, the VR-IV of the modified capsid encodes an amino acid sequence motif of STPGGTTGTNGLK (SEQ ID NO: 3).

Certain aspects of the modified AAV capsids and AAV virions of the present disclosure include VR-V encoding amino acid sequence $X_{11}X_{12}X_{13}X_{14}NNNSNFPWTAASX_{15}$ where $X_{11}$ is independently I or T; $X_{12}$ is independently A or P; $X_{13}$ is independently N, S or G; $X_{14}$ is independently D or Q; and $X_{15}$ is independently K or T. In certain embodiments, $X_{11}$ is I; $X_{12}$ is P; $X_{13}$ is S; $X_{14}$ is Q; and $X_{15}$ is K. In certain embodiments, the VR-V of the modified capsid encodes an amino acid sequence motif of IPSQNNNSNFPWTAASK (SEQ ID NO: 4).

Certain aspects of the modified AAV capsids and AAV virions of the present disclosure include VR-VI encoding amino acid sequence $KDDX_{16}X_{17}X_{18}$ where $X_{16}$ is independently E or D; $X_{17}$ is independently E or D; and $X_{18}$ is independently K or R. In certain embodiments, $X_{16}$ is D; $X_{17}$ is D; and $X_{18}$ is R. In certain embodiments, the VR-VI of the modified capsid encodes KDDDDR (SEQ ID NO: 9).

Certain aspects of the modified AAV capsids and AAV virions of the present disclosure include VR-VII encoding amino acid sequence $GKX_{19}X_{20}X_{21}X_{22}X_{23}X_{24}X_{25}X_{26}EX_{27}X_{28}X_{29}$ where $X_{19}$ is independently E or Q; $X_{20}$ is independently G or D; $X_{21}$ is independently T or A; $X_{22}$ is independently T, A or G; $X_{23}$ is independently A or R; $X_{24}$ is independently S or D; $X_{25}$ is independently N or D; $X_{26}$ is independently A, T or V; $X_{27}$ is independently L, V or Y; $X_{28}$ is independently D or G; and $X_{29}$ is independently N, K or H. In certain embodiments, $X_{19}$ is Q; $X_{20}$ is G; $X_{21}$ is A; $X_{22}$ is G; $X_{23}$ is R; $X_{24}$ is D; $X_{25}$ is N; $X_{26}$ is T; $X_{27}$ is Y; $X_{28}$ is D; and $X_{29}$ is H. In certain embodiments, the VR-VII of the modified capsid encodes an amino acid sequence motif of GKQGAGRDNTEYDH (SEQ ID NO: 5).

Certain aspects of the modified AAV capsids and AAV virions of the present disclosure include VR-VIII encoding amino acid sequence $QX_{30}X_{31}X_{32}X_{33}X_{34}PTX_{35}RX_{36}VX_{37}X_{38}$ where $X_{30}$ is independently S or N; $X_{31}$ is independently S or G; $X_{32}$ is independently N or R; $X_{33}$ is independently T or D; $X_{34}$ is independently A or N; $X_{35}$ is independently T or F; $X_{36}$ is independently T or D; $X_{37}$ is independently N or Q; and $X_{38}$ is independently H or D. In certain embodiments, $X_{30}$ is S; $X_{31}$ is S; $X_{32}$ is N; $X_{33}$ is T; $X_{34}$ is A; $X_{35}$ is F; $X_{36}$ is T; $X_{37}$ is N; and $X_{38}$ is D. In certain embodiments, the VR-VIII of the modified capsid encodes an amino acid sequence motif of QSSNTAPTTRTVND (SEQ ID NO: 6). In other embodiments, the VR-VIII of the modified capsid encodes an amino acid sequence motif of QNGRDNPTFRDVQH (SEQ ID NO: 8).

In some embodiments, the variant rAAV capsid comprises one or more of the substitutions R460G, N494S, S551D, A553T, L555Y, and N557H in SEQ ID NO: 1. In some embodiments, the variant comprises the substitutions R460G, N494S, S551D, A553T, L555Y, and N557H in SEQ ID NO: 1. In some embodiments, the variant comprises the substitutions R460G, N494S, S551D, A553T, L555Y, and N557H in SEQ ID NO: 1, as well as 1, 2, 3, 4, 5, 6, or more than 6 amino acid mutations relative to SEQ ID NO: 1.

In some embodiments, the AAV virions of the present disclosure are incorporated into at least one host cell. Examples of suitable host cells are mammalian cells including human host cells, including, for example, blood cells, stem cells, hematopoietic cells, CD34 cells, liver cells, cancer cells, vascular cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, or any one or more selected tissues of a mammal for which viral-based gene therapy is contemplated. Preferably, the host cells are liver cells.

AAV virions comprising the exemplary AAV3B variants of the present disclosure may include the virions as incorporated or transduced into at least one host cell. Examples of suitable host cells include human hepatocytes, e.g., hepatocellular carcinoma cell lines HUH-7 and HepG2, murine hepatocytes, e.g., H2.35, HEK293 (embryonic kidney) cells, HeLa cells, Cos cells, U87 cells, KB cells, and Vero cells. In certain embodiments, the modified AAV3B virions of the present disclosure are incorporated into HUH-7, H2.35 and/or HepG2 cells. In particular embodiments, virions comprising the DE5 variant are incorporated into HUH-7, H2.35 and/or HepG2 cells.

Embodiments of the AAV virions of the present disclosure further comprise a nucleotide sequence encoding at least one molecule providing helper function. The third nucleotide sequence may be a polynucleotide derived from an adenovirus or a herpes virus (e.g., HSV1). In particular embodiments, the polynucleotide is derived from adenovirus, e.g., Ad5.

In some aspects, the disclosure provides methods of selecting tissue-specific or cell-specific variants of an AAV virion includes (a) introducing a plurality of AAV virions into target tissues or cells; (b) allowing sufficient time to elapse to propagate additional virions; and (c) isolating the virions. Steps (a) through (c) may be repeated one or more times to enrich for a tissue-specific (e.g., hepatic tissue-specific) or cell-specific variant. Such enriched variants exhibit a higher target tropism for the target tissues or cells as compared to AAV serotype 3.

Embodiments of the AAV virions of the present disclosure include (a) a first nucleotide sequence encoding at least one therapeutic molecule; (b) a second nucleotide sequence comprising a regulatory sequence; (c) a third nucleotide sequence comprising a first AAV terminal repeat (e.g., from serotype 3); (d) a fourth nucleotide sequence comprising a second AAV terminal repeat (e.g., from serotype 3); and (e) a capsid comprising at least one AAV Cap protein that differs from wildtype serotype 3 at least at one amino acid position. The first nucleotide sequence is operably linked to the second nucleotide sequence and the first and second nucleotide sequences are interposed between the first and second AAV terminal repeat to form a transgene, and the resulting transgene is packaged within the capsid. Examples of suitable regulatory sequences include promoters and enhancers, e.g., a tissue specific promoter. Examples of suitable therapeutic molecules include polypeptides, peptides, antibodies, antigen binding fragments, growth factors, cytokines and other small therapeutic proteins, and any combination thereof.

In some aspects, the present disclosure provides methods for treating a disease or disorder. Such methods may comprise administering an effective amount of an AAV virion of the present disclosure. In some embodiments, the disease or disorder is Wilson's Disease.

The following drawings form part of the present specification and are included to demonstrate certain aspects of the present disclosure. The present disclosure may be better understood by reference to the following description taken in conjunction with the accompanying drawings, in which like reference numerals identify like elements.

BRIEF DESCRIPTION OF THE DRAWINGS

FIGS. 1A-1B show the wild-type (WT) nucleotide sequence (bottom rows) and corresponding WT amino acids (top rows, bold font) of AAV3B capsid gene and capsid protein, respectively. Degenerate positions within each variable region (VR) diversified in AAV serotype 3 capsid library (A3CL) are underlined. The degenerate nucleotide positions (in IUPAC code) encoded by synthetic oligonucleotides are shown in italics below the WT sequence. (SEQ ID NOS: 117-118)

FIG. 2 shows the nucleotide sequence of the synthetic fragment A3CL as designed. The degenerate nucleotide positions (in IUPAC code) are underlined. The overlap stretches of the synthetic DNA and the plasmid vector backbone are highlighted. (SEQ ID NO: 119)

FIG. 3 shows the amino acid sequence of AAV3B VP1. Degenerate positions are labeled by X and underlined. (SEQ ID NO: 120)

FIG. 11 shows an amino acid sequence alignment between wild-type AAV3B VP1 region and the AAV3B-DE5 variant. (SEQ ID NO: 122-123)

FIG. 16A shows copy number distribution; for each copy number (x axis), the number of distinct sequences present at that copy number is shown (y axis). In the plasmid library, almost all sequences have a single occurrence, while in the viral library there is a wider distribution, with more sequences having diverse levels of abundance; in both cases, the sequence with the highest abundance is wt AAV3B, the library parent, indicated with arrows. FIG. 16B shows distribution of the number of mutations per sequence; the number of mutations for each sequence varies between 0 (wt AAV3B) and 34 (100% of the 34 variable positions mutated), with a peak at 24 and 23 mutations respectively for the plasmid and viral libraries, and an average of 21.56 and 23.26 respectively. FIG. 16C shows Euler diagram showing the overlap between the distinct sequences in the plasmid and the viral libraries.

FIG. 17 shows evolution of sequence frequencies with selection rounds. Sequences present at more than 1% after at least one round of selection are indicated with unique symbol (V1 to V16). All other sequences are combined under a single color (Other). AAV3B-DE5 is shown as sequence V 1.

FIGS. 18A-18D show AAV3-DE5 mutations. FIG. 18A shows alignment between parental capsid AAV3B and evolved capsid AAV3B-DE5; only the four regions that were diversified in the library design are shown (the sequences are identical outside these regions); numbers on top designate the region position in the capsid (VP1 numbering); sequence identity is represented by a dot. FIG. 18B shows position of the 24 mutations displayed in AAV3B 3D structure. FIG. 18C shows heat map showing enrichment factors between rounds of selection for each mutation; the enrichment factor between two rounds of selection (for example a and b) for a mutation at a particular position is defined as the frequency of the corresponding amino acid at that position in the next generation sequencing (NGS) sample for round b divided by the corresponding frequency for round a. FIG. 18D shows enrichment scores of AAV3B-DE5 mutations; for each position the score is defined as the product of the 4 enrichment factors shown in FIG. 18C.

FIG. 19A show graphical representation of transduction efficiencies (%mApple+cells), mApple MFI, FLuc activity levels for HUH-7 adherent cells transduced with either wt AAV3B or AAV3B-DE5 at different MOIs. FIG. 19B shows kinetics of transduction efficiencies (%mApple+) and AAV genome copy/cell of HUH-7 adherent cells transduced with $5 \times 10^5$ MOI of either wt AAV3B or AAV3B-DE5. FIG. 19C shows GFP transgene expression analysis of primary human hepatocytes, primary monkey hepatocytes or primary mouse hepatocytes transduced with three different MOIs ($1 \times 10^4$, $3 \times 10^4$ and $1 \times 10^5$) of either AAV8 or AAV3B-DE5 in vitro. Transgene expression was normalized to GAPDH expression levels. Statistical analysis was performed by 2-way ANOVA with Sidak's multiple comparisons test for FIGS. 19A-19B. Data are represented as mean±SEM.

FIG. 20A shows determination of reciprocal NAb titers to wt AAV3B or AAV3B-DE5 by using increasing concentrations of pooled IVIg (100-6400 μg/mL). The IVIg concentration at which 50% FLuc expression is reduced, as compared to no IVIg control, is indicated with the red dotted lines. FIG. 20B shows average reciprocal NAb titers for wt AAV3B and AAV3BDE5, determined using the FLuc based in vitro neutralizing assay. Data are average of 10 independent experiments. Data are represented as mean±SD for FIG. 20A, with statistical significance between wt AAV3B and AAV3B-DE5 conducted by 2-way ANOVA with Sidak's multiple comparisons test. Data are represented as mean±SEM for FIG. 20B, with statistical significance between wt AAV3B and AAV3B-DE5 conducted by unpaired t-test with Welch's correction.

FIG. 21A shows reciprocal NAb titers for wt AAV3B and AAV3B-DE5 obtained from 100 donor serum samples using the in vitro FLuc based neutralizing assay. FIG. 21B shows determination of seroprevalence for wt AAV3B and AAV3B-DE5 from FIG. 21A using either 1:2 or 1:5 serum dilution as cut-off. FIG. 21C shows 48 samples with detectable titers were analyzed for fold difference between wt AAV3B and AAV3B-DE5 reciprocal NAb titers. 35% and 40% of these 48 patient samples have 2-16 fold and 1.5-2 fold higher titers respectively for wt AAV3B as compared to AAV3B-DE5. 19% and 6% of patient samples have 1-1.5 fold and 0.7-1 fold higher titers respectively for wt AAV3B as compared to AAV3B-DE5. Statistical analysis for FIG. 21A was performed using a two-tailed Mann Whitney test following a normality distribution determination, and for FIG. 21B was conducted by Fisher's exact test two-tailed test using a 2×2 contingency table.

FIG. 22A shows a schematic representing steps in the generation of the human liver chimeric mouse. (Fah)$^{-/-}$ NOD Rag1$^{-/-}$ Il2rg$^{null}$ (FNRG) mice were humanized with mouse-passaged primary human hepatocytes (huFNRG mice). After transplantation, mice were cycled off NTBC to expand the human graft. FIG. 22B shows chimerism was determined by human albumin (hAlb) quantification in mouse serum, which correlates well with humanization. Once mice had reached peak hAlb levels they were challenged one day after restarting NTBC. FIG. 22C shows flow gating strategy to differentiate between human and mouse hepatocytes, using human HLA-1 and mouse CD81 antibodies, and to quantify the frequencies of GFP expressing cells. FIG. 22D shows comparison of transduction frequencies of AAV3-ST, AAV3B-DE5, and LK03 by quantifying percent GFP human hepatocytes by flow cytometry. Data for FIGS. 22B and 22D are shown in median±SEM.

DETAILED DESCRIPTION OF THE INVENTION

Figure 4:
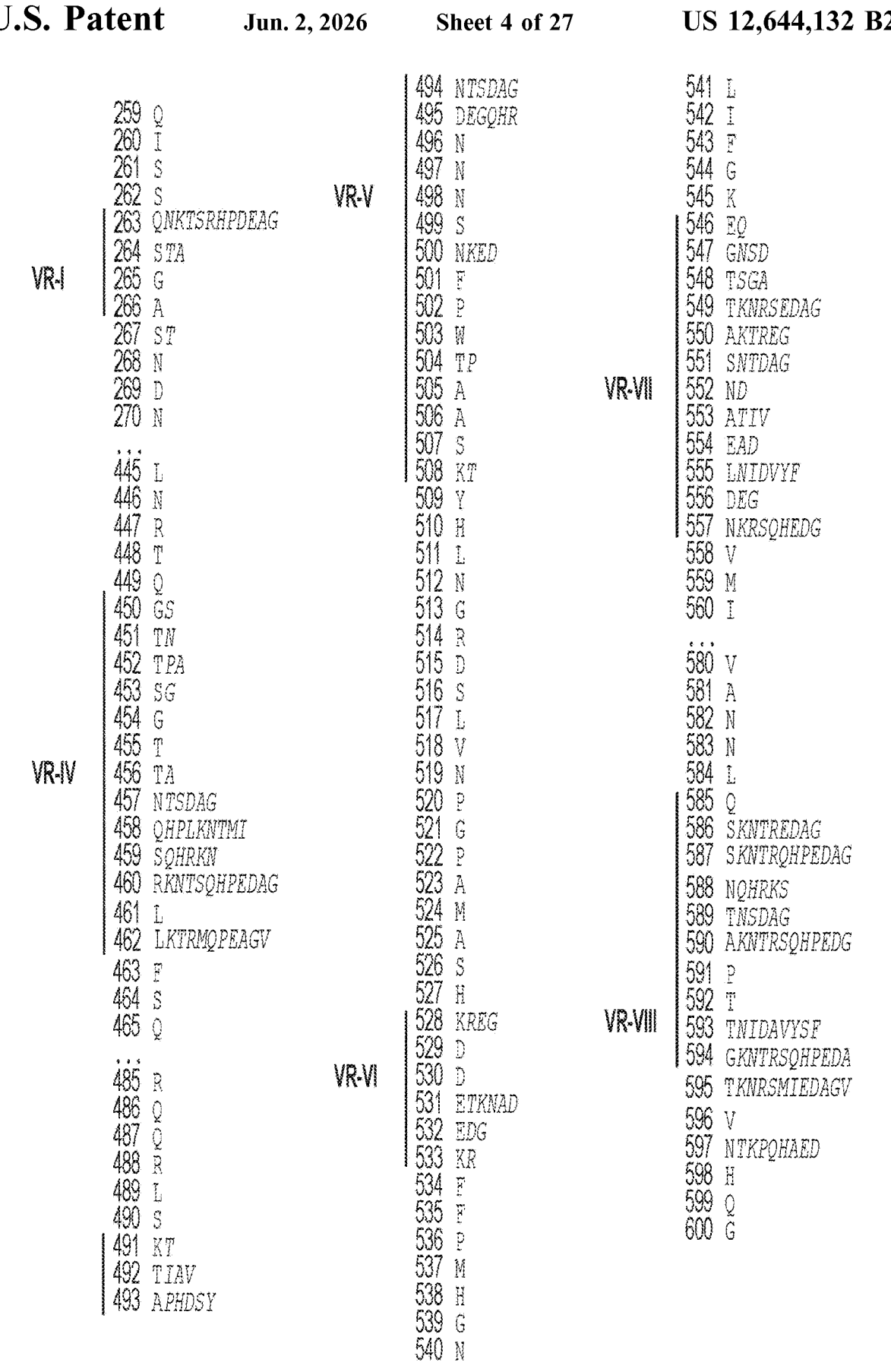
FIG. 4 shows the amino acid sequences of the A3CL VRs encompassing WT AAV3B VP1 capsid residues 259-600. WT sequences are shown in black, degenerate residues — in italics. Not modified conservative residues between VRs are not shown. VRs borders are indicated by vertical lines. (SEQ ID NO: 121)

AAV-derived viral particles are promising tools for human gene therapy applications because of reduced pathogenicity compared to other viral vectors, episomal localization, and stable transgene expression. AAV viral particles show huge promise for the delivery of therapeutic genes to the liver. Improving the transduction efficiency of AAV particles having tropism for hepatic cells would be of great benefit to disease of the liver, including Wilson's Disease, hemophilia, lysosomal storage disorders and Crigler-Najjar syndrome. AAV virions of serotypes 3 and 3B have been demonstrated to possess tropism for liver cells. See Li et al., *Mol Ther.* 2015; 23(12): 1867-1876 and Glushakova, L G et al., *Mol Genet Metab.* 2009; 98: 289-299, each of which are herein incorporated by reference. This in part due to AAV3B's use of human hepatocyte growth factor receptor (huHGFR) as a cellular coreceptor, which restricts transduction to the liver.

The tissue tropism and transduction efficiency of AAV particles is determined by the nature of amino acid residues exposed at the surface of the capsid (Wu et al., *J Virol.* 2006, 80(22):11393-7, herein incorporated by reference). Therefore, manipulating the amino acids of the capsid proteins provides an opportunity to fine-tune the tissue tropism of the particle and also improve transduction efficiency. However, certain manipulations, e.g., substitutions of amino acids, of the capsid protein can cause it to mis-fold or not form a capsid at all. To circumvent issues of protein mis-folding and capsid mis-forming, the recombinant AAV3B (rAAV3B) variant proteins and viral particles disclosed herein were identified from a variant AAV3B capsid library that was built by making substitutions in only the variable loops of the capsid protein. Herein, "variable loops" are also referred to as "variable regions". AAV3B has 9 variable regions, numbered from VRI to VRIX.

In the practice of the present disclosure, the transduction efficiency of a mutated rAAV capsid will be higher than that of the corresponding, unmodified, wild-type AAV3B capsid, and as such, will preferably possess a transduction efficiency in a mammalian cell that is at least 2-fold, at least about 4-fold, at least about 6-fold, at least about 8-fold, at least about 10-fold, or at least about 12-fold or higher in a selected mammalian host cell than that of a virion that comprises a corresponding, unmodified rAAV capsid. In certain embodiments, the transduction efficiency of the rAAV capsids provided herein will be at least about 15-fold higher, at least about 20-fold higher, at least about 25-fold higher, at least about 30-fold higher, or at least about 40, 45, or 50-fold or more greater than that of a virion that comprises a corresponding, wild-type capsids.

In the practice of the present disclosure, the transduction efficiency of a modified rAAV capsid may be higher than that of a modified AAV3-ST capsid, and as such, may preferably possess a transduction efficiency in a mammalian cell that is at least 2-fold, at least about 4-fold, at least about 6-fold, at least about 8-fold, at least about 10-fold, or at least about 12-fold or higher in a selected mammalian host cell than that of a virion that comprises an AAV3-ST capsid. In certain embodiments, the transduction efficiency of the disclosed modified rAAV capsids provided herein will be at least about 15-fold higher, at least about 20-fold higher, at least about 25-fold higher, at least about 30-fold higher, or at least about 40, 45, or 50-fold or more greater than that of a virion that comprises an AAV3-ST capsid.

In some embodiments, relative (or differential) transduction efficiency is evaluated in vivo by measuring the differential expression of a protein encoded in the rAAV vector (which indicates the degree of transduction of that protein) of an administered virion in a sample obtained from subjects that had been administered the virions under comparison. In other embodiments, transduction efficiency is evaluated in vitro by administering to one or more cells (e.g., human cells) the virions and measuring the differential percent of transduction (i.e., % expression of encoded protein) by flow cytometry between samples. Cells cultures may be adherent or spheroid for any such evaluation. Transduction of cells may occur at any suitable MOI. In some embodiments, evaluation is performed by transducing cells at an MOI selected from between $1 \times 10^4$ and $2 \times 10^8$. In some embodiments, evaluation is performed by transducing cells at an MOI selected from $1 \times 10^4$, $5 \times 10^4$, $1 \times 10^5$, $2.5 \times 10^5$ and $5 \times 10^5$. The encoded protein may be a reporter protein (e.g., a fluorescent protein) or a therapeutic protein.

It was previously shown that pre-existing neutralized antibodies (NAb) against AAV3B are relatively lower (48% of animals with detectable NAb) as compared with AAV8 (>75% of animals positive for AAV8 NAb) in non-human primates (see Li et al., *Mol Ther.* 2015). Screening of an AAV3B capsid library in a human liver xenograft mouse model led to the identification of AAV3B capsid variants that possess enhanced efficiency to transduce hepatic cells compared to the transduction efficiency of wild-type AAV3B capsid proteins. Data reported in Examples 2 and 3 indicate that these capsid variants have reduced seroreactivity, and in particular possess enhanced ability to evade neutralizing antibodies of host liver cells, such as human liver cells, in vitro.

Accordingly, in some embodiments, the virions disclosed herein (e.g., DE5 virions) demonstrate reduced seroreactivity relative to a wild-type AAV3B capsid, or relative to another AAV3B variant capsid, such as AAV3-ST or AAV3-LK03. See, e.g., Ling, C, et al., *Mol Ther.* 2014; 22: S2, incorporated herein by reference. In some embodiments, the disclosed virions evade circulating an amount of neutralizing antibodies (Nab) that would have effectively neutralized by half the level of AAV transduction by wild-type AAV3B. In some embodiments, the disclosed virions possess enhanced ability to evade neutralizing antibodies of host liver cells in vivo, e.g., in a subject, such as a primate (e.g., a human or non-human primate). In some embodiments, the disclosed virions provide an about 1.5-fold, a 2-fold, a 2.5-fold, a 3-fold, a 3.2-fold, a 3.5-fold, a 4-fold, a 5-fold, a 6-fold, a 10-fold, a 12-fold or a 15-fold decrease in seroreactivity to neutralizing anti-AAV (e.g., anti-AAV3) antibodies in the subject, relative to a wild-type recombinant AAV3B virion. In some embodiments, the virions provide an about 2-fold decrease in seroreactivity to neutralizing anti-AAV antibodies in the subject, relative to a wild-type recombinant AAV3B virion. In certain embodiments, the disclosed virions may possess a 2-fold increase in resistance to Nab neutralization, e.g., neutralization by pooled intravenous immunoglobulin (IVIg) and/or anti-AAV3B antibodies, in vivo or in vitro.

Correspondingly, in some aspects, the disclosure provides methods of administration of rAAV virions (or particles) to a subject any of the disclosed AAV3B capsid variants, wherein the step of administering provides for reduced seroreactivity relative to a method of administering a wild-type AAV3B virion. In some aspects, the disclosure provides methods of administration of rAAV virions (or particles) to a subject any of the disclosed AAV3B capsid variants, wherein the step of administering provides an about 1.5-fold, a 2-fold, a 2.5-fold, a 3-fold, a 3.2-fold, a 3.5-fold, a 4-fold, a 5-fold, a 6-fold, a 10-fold, a 12-fold or a 15-fold reduction in seroreactivity to neutralizing anti-AAV (e.g., anti-AAV3) antibodies in the subject, relative to a method of administering wild-type recombinant AAV3B virion.

Reduced seroreactivity and evasion of NAb in subjects may be measured by any method known in the art. In some embodiments, the degree of reduced seroreactivity and/or evasion of NAb is evaluated in vivo in human sera by measuring the differential expression of a protein encoded in the rAAV vector (which indicates the degree of transduction of that protein) of an administered virion in a sample obtained from a subject that had been administered the virions.

In other embodiments, degree of reduced seroreactivity and/or evasion of NAb is evaluated in vitro by pre-incubating an rAAV virion encoding a protein with pooled IVIg, transducing one or more cells (e.g., human cells) with the pre-incubated virions, and measuring the differential percent of transduction (i.e., % expression of encoded protein) by flow cytometry between samples. In some embodiments, reduced seroreactivity and/or evasion of NAb is evaluated in vitro by pre-incubating an rAAV virion encoding a protein with serum samples from healthy subjects (e.g., about 50 or 100 human subjects), transducing one or more cells (e.g., human cells) with the pre-incubated virions, and measuring the percent of transduced cells (i.e., % of cells expressing encoded protein) by flow cytometry. In addition to percent of transduced cells, differential transduction between samples may be measured by fluorescence (firefly luciferase or FLuc activity) or mean fluorescence intensity (mFI). Transduction of cells may occur at any suitable MOI. In some embodiments, evaluation is performed by transducing cells at an MOI selected from between $1\times10^4$ and $2\times10^8$. In some embodiments, evaluation is performed by transducing cells at an MOI selected from $1\times10^4$, $5\times10^4$, $1\times10^5$, $2.5\times10^5$ and $5\times10^5$. The encoded protein may be a reporter protein (e.g., a fluorescent protein) or a therapeutic protein.

In some embodiments, seroreactivity is evaluated in vitro by measuring the average reciprocal titers of NAb in cells generated from the experiments described above.

Accordingly, provided herein are capsid mutants, or variants, of wild-type AAV3B, compositions of such particles and methods of using these compositions to transduce hepatic cells, exhibit reduced seroreactivity, and/or evade a host humoral immune response.

In some aspects, the present disclosure provides variants of the wild-type AAV3B capsid. The wild-type AAV3B capsid, VP1 region is set forth as SEQ ID NO: 1, below. In some embodiments, the variants, or modified capsids, of the present disclosure have an amino acid sequence essentially as set forth in SEQ ID NO: 1. In certain embodiments, the modified AAV capsid is truncated by 1, 2, 3, 4, 5, 6, 7, 8, 9, 10, 11, 12, 13, 14, 15, or 15-20 amino acids relative to the wild-type AAV3B VP1 sequence of SEQ ID NO: 1.

```
                                          (SEQ ID NO: 1)
MAADGYLPDWLEDNLSEGIREWWALKPGVPQPKANQQHQDNRRGLVLPG

YKYLGPGNGLDKGEPVNEADAAALEHDKAYDQQLKAGDNPYLKYNHADA

EFQERLQEDTSFGGNLGRAVFQAKKRILEPLGLVEEAAKTAPGKKRPVD

QSPQEPDSSSGVGKSGKQPARKRLNFGQTGDSESVPDPQPLGEPPAAPT

SLGSNTMASGGGAPMADNNEGADGVGNSSGNWHCDSQWLGDRVITTSTR

TWALPTYNNHLYKQISSQSGASNDNHYFGYSTPWGYFDFNRFHCHFSPR

DWQRLINNNWGFRPKKLSFKLFNIQVKEVTQNDGTTTIANNLTSTVQVF

TDSEYQLPYVLGSAHQGCLPPFPADVFMVPQYGYLTLNNGSQAVGRSSF

YCLEYFPSQMLRTGNNFQFSYTFEDVPFHSSYAHSQSLDRLMNPLIDQY

LYYLNRTQGTTSGTTNQSRLLFSQAGPQSMSLQARNWLPGPCYRQQRLS

KTANDNNNSNFPWTAASKYHLNGRDSLVNPGPAMASHKDDEEKFFPMHG

NLIFGKEGTTASNAELDNVMITDEEEIRTTNPVATEQYGTVANNLQSSN

TAPTTRTVNDQGALPGMVWQDRDVYLQGPIWAKIPHTDGHFHPSPLMGG

FGLKHPPPQIMIKNTPVPANPPTTFSPAKFASFITQYSTGQVSVEIEWE

LQKENSKRWNPEIQYTSNYNKSVNVDFTVDTNGVYSEPRPIGTRYLTRN

L
```

In some embodiments, the modified AAV capsid comprises an amino acid sequence that is at least 80%, at least 85%, at least 90%, at least 95%, at least 98%, or at least 99.5% identical the sequence set forth as SEQ ID NO: 2. In some embodiments, the modified AAV capsid comprises 1, 2, 3, 4, 5, 6, 7, 8, 9, 10, 11, 12, 13, 14, 15, or 15-20 amino acid substitutions relative to the amino acid sequence of SEQ ID NO: 2. These differences may comprise amino acids that have been inserted, deleted, or substituted relative to the sequence of SEQ ID NO: 2. In some embodiments, the disclosed capsid rAAV variants comprise truncations at the N- or C-terminus relative to the sequence of SEQ ID NO: 2.

In some embodiments, the disclosed capsid rAAV variants comprise stretches of 15, 20, 25, 30, 35, 40, 45, 50, or more than 50 consecutive amino acids in common with the sequence of SEQ ID NO: 2.

In particular embodiments, the modified AAV capsid comprises AAV3B-DES, or "DE5," ("Directed Evolution 5") which comprises the amino acid sequence set forth as SEQ ID NO: 2:

```
                                          (SEQ ID NO: 2)
MAADGYLPDWLEDNLSEGIREWWALKPGVPQPKANQQHQDNRRGLVLPG

YKYLGPGNGLDKGEPVNEADAAALEHDKAYDQQLKAGDNPYLKYNHADA

EFQERLQEDTSFGGNLGRAVFQAKKRILEPLGLVEEAAKTAPGKKRPVD

QSPQEPDSSSGVGKSGKQPARKRLNFGQTGDSESVPDPQPLGEPPAAPT

SLGSNTMASGGGAPMADNNEGADGVGNSSGNWHCDSQWLGDRVITTSTR

TWALPTYNNHLYKQISSASGASNDNHYFGYSTPWGYFDFNRFHCHFSPR

DWQRLINNNWGFRPKKLSFKLFNIQVKEVTQNDGTTTIANNLTSTVQVF

TDSEYQLPYVLGSAHQGCLPPFPADVFMVPQYGYLTLNNGSQAVGRSSF

YCLEYFPSQMLRTGNNFQFSYTFEDVPFHSSYAHSQSLDRLMNPLIDQY

LYYLNRTQSTPGGTTGTNGLKFSQAGPQSMSLQARNWLPGPCYRQQRLS

KIPSQNNNSNFPWTAASKYHLNGRDSLVNPGPAMASHKDDDDRFFPMHG

NLIFGKQGAGRDNTEYDHVMITDEEEIRTTNPVATEQYGTVANNLQSSN

TAPTTRTVNDQGALPGMVWQDRDVYLQGPIWAKIPHTDGHFHPSPLMGG

FGLKHPPPQIMIKNTPVPANPPTTFSPAKFASFITQYSTGQVSVEIEWE

LQKENSKRWNPEIQYTSNYNKSVNVDFTVDTNGVYSEPRPIGTRYLTRN

L
```

Elsewhere herein, the DE5 variant may be referred to as "MP5." Accordingly, provided herein are rAAV3B capsid proteins comprising substitutions relative to the wild-type AAV3B VP1 sequence (e.g., as set forth in SEQ ID NO: 1). In some embodiments, an amino acid substitution in any one of the variant AAV3B capsid proteins disclosed herein lies in a variable region as defined by wild-type AAV3B VP1 protein. It should be understood that any positioning of an amino acid as described herein is with respect to the sequence of the wild-type AAV3B VP1 sequence as set forth in SEQ ID NO: 1.

In some embodiments, a variant rAAV3B capsid comprises one or more amino acid substitutions in any one variable region (e.g., VRI, VRII, VRIII, VRIV, VRV, VRVI, VRVII, VRVIII or VRIX). In some embodiments, a variant rAAV3B capsid comprises one or more amino acid substitutions in more than one variable region (e.g., VRI and VRII, VRI and VRVII or VRIV, VRII).

Certain aspects of the modified AAV capsids and AAV virions of the present disclosure include the second nucleotide encoding variants of an AAV Cap protein as listed in Table 4 (whose sequences are numbered 2-86 (SEQ ID NOs: 32-116)).

In some aspects, the present disclosure provides novel infectious rAAV virions and viral particles, as well as expression constructs that encode novel AAV virions. The present disclosure further provides novel nucleic molecules encoding one or more selected diagnostic and/or therapeutic agents for delivery to a selected population of mammalian cells, such as human cells, wherein the nucleic acid molecules are comprised within the disclosed rAAV virions and viral particles.

The present disclosure provides improved rAAV-based expression constructs that encode one or more therapeutic agents useful in the preparation of medicaments for the prevention, treatment, and/or amelioration of one or more diseases, disorders or conditions resulting from a deficiency in one or more cellular components. In particular, the present disclosure provides virions comprising modified capsids, as generated after screening of one or more libraries of rAAV-based genetic constructs encoding one or more selected molecules of interest, such as, for example, one or more diagnostic or therapeutic agents (including, e.g., proteins, polypeptides, peptides, antibodies, antigen binding fragments, siRNAs, RNAis, antisense oligo- and poly-nucleotides, ribozymes, and variants and/or active fragments thereof), for use in the diagnosis, prevention, treatment, and/or amelioration of symptoms of mammalian diseases, disorders, conditions, deficiencies, defects, trauma, injury, and such like.

In some embodiments, the novel capsids of the infectious virions disclosed herein may have an improved efficiency in transducing one or more of a variety of cells, tissues and organs of interest, when compared to wild-type, unmodified capsids. The improved rAAV capsids provided herein may transduce one or more selected host cells at higher-efficiencies (and often much higher efficiencies) than conventional, wild type (i.e., unmodified) rAAV capsids.

The virions as described herein may be of different AAV serotypes, and the mutation of one or more of the sequences described herein may result in improved viral vectors, which are capable of higher-efficiency transduction than that of the corresponding, non-substituted vectors from which the mutants were prepared. In some embodiments, the virions as described herein may be of an AAV1, AAV2, AAV3, AAV4, AAV5, AAV6, AAV7, AAV8, AAV9, AAV10, AAV11, AAV12, or AAV13 serotype.

The present disclosure further provides populations and pluralities of the disclosed rAAV virions, infectious viral particles, and mammalian host cells that include one or more nucleic acid segments encoding them. The disclosed vectors and virions may be comprised within one or more diluents, buffers, physiological solutions or pharmaceutical vehicles, or formulated for administration to a mammal in one or more diagnostic, therapeutic, and/or prophylactic regimens. The disclosed viral particles, virions, and pluralities thereof may also be provided in excipient formulations that are acceptable for veterinary administration to selected livestock, exotics, domesticated animals, and companion animals (including pets and such like), as well as to non-human primates, zoological or otherwise captive specimens, and such like.

Preferably, the mammalian host cells will be human host cells, including, for example blood cells, stem cells, hematopoietic cells, CD34 cells, liver cells, cancer cells, vascular cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, retinal cells or any one or more selected tissues of a mammal for which viral-based gene therapy is contemplated.

The present disclosure further provides compositions and formulations that include one or more of the host cells or viral particles of the present disclosure together with one or more pharmaceutically acceptable buffers, diluents, or carriers. Such compositions may be included in one or more diagnostic or therapeutic kits, for diagnosing, preventing, treating or ameliorating one or more symptoms of a mammalian disease, injury, disorder, trauma or condition.

The present disclosure further includes methods for providing a mammal in need thereof with a diagnostically- or therapeutically-effective amount of a selected biological molecule, the method comprising providing to a cell, tissue or organ of a mammal in need thereof, an amount of an rAAV expression construct; and for a time effective to provide the mammal with a diagnostically- or a therapeutically-effective amount of the selected biological molecule.

The present disclosure further provides methods for diagnosing, preventing, treating, or ameliorating at least one or more symptoms of a disease, a disorder, a condition, an injury, an abnormal condition, or trauma in a mammal. In an overall and general sense, the methods include at least the step of administering to a mammal in need thereof one or more of the disclosed rAAV constructs, in an amount and for a time sufficient to diagnose, prevent, treat or ameliorate the one or more symptoms of the disease, disorder, condition, injury, abnormal condition, or trauma in the mammal.

The present disclosure also provides methods of transducing a population of mammalian cells. In an overall and general sense, the methods include at least the step of introducing into one or more cells of the population, a composition that comprises an effective amount of one or more of the rAAV virions disclosed herein.

In other aspects, the present disclosure provides compositions, as well as therapeutic and/or diagnostic kits that include one or more of the disclosed AAV compositions, formulated with one or more additional ingredients, or prepared with one or more instructions for their use.

In some aspects, the present disclosure provides methods for using the disclosed improved rAAV virions in a variety of ways, including, for example, ex situ, ex vivo, in vitro and in vivo applications, methodologies, diagnostic procedures, and/or gene therapy regimens. Because many of the improved vectors described herein are also resistant to proteasomal degradation, they possess significantly increased transduction efficiencies in vivo making them particularly well suited for viral particle-based human gene therapy regimens, and in particular, for delivering one or more genetic constructs to selected mammalian cells in vivo and/or in vitro.

In one aspect, the present disclosure provides compositions comprising AAV virions, viral particles, and pharmaceutical formulations thereof, useful in methods for delivering genetic material encoding one or more beneficial or therapeutic product(s) to mammalian cells and tissues. In particular, the compositions and methods of the present disclosure provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and conditions.

Contemplated herein are also variant rAAV capsid proteins of serotypes other than serotype 3B. In some embodiments, any one of the amino acid substitutions described herein are in a variable region of the capsid protein of a serotype other than serotype 3B that is homologous to the variable region of AAV3B. In some embodiments, a variant rAAV capsid protein of a serotype other than serotype 3B is of any serotype other than AAV3B (e.g., 1, 2, 3, 4, 5, 6, 7, 8, 9, 10, 11, 12 or 13). In some embodiments, a variant rAAV capsid protein of a serotype other than serotype 3B is of a closely related serotype (e.g., AAV3).

Library Design And Construction

In another aspect, the present disclosure concerns libraries of rAAV capsid variants that demonstrate improved properties useful in the delivery of one or more therapeutic agents to selected mammalian cells, and particularly for use in the prevention, treatment, and/or amelioration of one or more disorders in a mammal into which the vector construct may be introduced. In some embodiments, the disclosed libraries comprise rAAV3 capsid variants.

Comparison of the AAV VP3 structure among various serotypes has revealed highly homologous sequences interspersed with more evolutionary divergent areas. These amino acid stretches are commonly designated as VRs I through IX (variable regions I-IX; also known as "loops"). VRs are localized at the surface of the assembled capsid and are assumed to be responsible for the capsid interaction with cell surface receptors and other host factors. Because of their location, VRs are also predicted to be less critical for capsid assembly. Therefore, the guiding principle of the library's design was to modify only surface VRs while keeping the backbone sequence unchanged to maintain the integrity of the assembling scaffold. All candidate positions for mutagenesis in the AAV3 background, were selected from the alignment of known variants, which can be evaluated on a three dimensional model of the AAV3 capsid. The amino acid diversity of VR-I, VR-IV, VR-V, VR-VI, VR-VII and VR-VIII is shown in FIG. 4. AAV3 wildtype VR-II, VR-III and VR-IX and non-variable regions of VP3 were incorporated in the plasmid library. The wild-type AAV3B sequence is set forth in SEQ ID NO: 1.

The AAV3B library of the present disclosure was built in three steps: first, VR parent sub-libraries were prepared each containing mutations in only one VR (B: VR-IV, C: VR-VII, D: VR-VIII) or a subset of VRs (A: VR-I+VR-V+VR-VI), then, structurally compatible sequences were combined to generate master libraries (A+B+C: VRs I, IV, V, VI, VII) and (D: VR-VIII), and finally the master libraries were packaged. See Example 1 and FIG. 5. Methods for generating and assembling DNA fragments for the library are disclosed in International Publication Nos. WO 2015/048534 and WO 2017/070476, and U.S. Pat. No. 7,220,577, each of which are incorporated herein by reference. The completed master library comprised $10^7$ variants.

The amino acid substitutions in the wild-type AAV3B capsid proteins disclosed herein are epistatic, i.e. that they interact with one another, e.g., synergistically. The disclosed substitutions may be grouped into motifs of substitutions. In designing the disclosed library, motifs were introduced to the capsids simultaneously and stochastically, rather than once at a time. The substitutions in each capsid variant were determined to be epistatic and act synergistically on capsid binding and transduction behavior. These motifs confer unexpectedly enhanced transduction efficiencies and an ability to evade neutralizing antibodies relative to wild-type capsids of the prior art.

Tissue-Specific or Cell-Specific Virions

The master library may be used to select virions having capsids containing degenerate or otherwise modified Cap protein (i.e., Cap protein that differs from wildtype serotype 3 at least at one amino acid position) that are targeted to particular tissue or cell types. For example, virions made according to the present disclosure include those that exhibit a new tropism, e.g., those capable of infecting cells normally non-permissive to AAV infection in general or at least non-permissive to AAV3 infection, as well as those that exhibit an increased or decreased ability to infect a particular cell or tissue type. As another example, virions made according to the present disclosure include those that lack the ability to infect cells normally permissive to AAV infection in general or at least normally permissive to AAV3 infection. To select for virions having a particular cell- or tissue-specific tropism, a packaged master library is introduced into a target cell. Preferably, the target cell is also infected with a helper virus (e.g., adenovirus, or Ad). The target cell is cultured under conditions that allow for the production of virions, resulting in a population of virions that are harvested from the target cell. This population of virions has been selected for having a tropism for that target cell.

As controls in a typical experiment in which virions having a particular tropism are selected, cells in different flasks or dishes may be simultaneously infected with WT AAV3 or rAAV using the same conditions as used for the library. After a suitable time post-infection, cells may be harvested, washed and the virions purified using a suitable purification method. See Gao et al., *Hum. Gene Ther.* 9:2353-62, 1998; U.S. Pat. No. 6,146,874; and Zolotukhin et al., *Gene Ther.* 6:973-85, 1999, each of which are incorporated herein by reference. AAV and helper virions (e.g., Ad) from each infection may be titered, e.g., by real-time PCR, and the AAV virions may then be further propagated, resulting in a stock of selected virions.

Once the selected population of virions having a desired tropism is isolated, nucleic acid from the virions is isolated and the sequence of the nucleotide sequence encoding the at least one AAV Cap protein is determined. Virions constructed and selected according to the present disclosure (e.g., virions comprising DE5) that can specifically target diseased cells or tissues over non-diseased cells or tissues are particularly useful.

Alternatively, tissue- or cell-specific virions may be selected using an in vivo approach. For example, mice (or other suitable host) may be injected with a suitable amount of viral preparation (e.g., $1 \times 10^{10}$ to $1 \times 10^{11}$ vector genomes (vg) in the case of mice) via the tail vein. More than one round of selection may be performed by injecting original master library for the first round and target-enriched libraries in subsequent rounds. Hosts are euthanized after an incubation period (3 to 4 days for mice), and episomal DNA is purified from the target cells or tissue and used as a template to amplify capsid DNA sequences. Target-enriched libraries may then be generated, purified and quantified. After several rounds of selection, amplified capsid DNA may be inserted into an appropriate vector for cloning and random clones may be analyzed by sequencing.

Expression Constructs

In some aspects, the present disclosure provides polynucleotide expression constructs that encode one or more of the disclosed capsids as described herein. The expression construct may be comprised within a plasmid. These plasmids may comprise one or more nucleotide substitutions to the nucleic acid sequence that encodes a wild-type AAV3B capsid, e.g., one or more nucleotide substitutions in one or more variable regions.

In some embodiments, the nucleic acid vector comprises one or more transgenes comprising a sequence encoding a protein or polypeptide of interest operably linked to a promoter, wherein the one or more transgenes are flanked on each side with an ITR sequence. In some embodiments, the nucleic acid vector further comprises a region encoding a Rep protein as described herein, either contained within the region flanked by ITRs or outside the region or nucleic acid) operably linked to a promoter, wherein the one or more nucleic acid regions. The ITR sequences can be derived from any AAV serotype (e.g., 1, 2, 3, 4, 5, 6, 7, 8, 9, or 10) or can be derived from more than one serotype. In some embodiments, the ITR sequences are derived from AAV2 or AAV3. In other embodiments, the ITR sequences of the first serotype are derived from AAV1, AAV5, AAV6, AAV7, AAV8, AAV9 or AAV10. In some embodiments, the ITR sequences are the same serotype as the capsid (e.g., AAV3 ITR sequences and AAV3 capsid, etc.).

ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, et al. Proc Natl Acad Sci USA. 1996; 93(24):14082-7; and Curtis A. Machida, Methods in Molecular Medicine™ Viral Vectors for Gene Therapy Methods and Protocols. 10.1385/1-59259-304-6:201 Humana Press Inc. 2003: Chapter 10, Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

In other aspects, the present disclosure provides rAAV nucleic acid vectors that may comprise a nucleic acid segment further comprises a promoter, an enhancer, a post-transcriptional regulatory sequence, a polyadenylation signal, or any combination thereof, operably linked to the nucleic acid segment that encodes he selected polynucleotide of interest. Preferably, the promoter is a heterologous promoter, a tissue-specific promoter, a cell-specific promoter, a constitutive promoter, an inducible promoter, or any combination thereof. Preferably, the expression constructs of the present disclosure further include at least promoter capable of expressing, or directed to primarily express, the nucleic acid segment in a suitable host cell (e.g., a liver cell) comprising the vector.

In certain embodiments, nucleic acid segments cloned into one or more of the novel rAAV nucleic acid vectors described herein will preferably express or encode one or more transgenes of interest. Such transgenes of interest may comprise polypeptides, peptides, ribozymes, peptide nucleic acids, siRNAs, RNAis, antisense oligonucleotides, antisense polynucleotides, antibodies, antigen binding fragments, or any combination thereof.

In certain embodiments, the transgene of interest is ATP7B (e.g., human ATPB7B, UniProtKB accession number: P35670). In some embodiments, the transgene of interest encodes a P-type ATPase. In certain embodiments, the transgene comprises the F8 gene (e.g., the human F8 gene), which encodes coagulation factor VIII in humans (UniProtKB accession number: P00451). In certain embodiments, the transgene comprises the GAA gene (e.g., the human GAA gene), which encodes lysosomal acid alpha-glucosidase enzyme in humans (UniProtKB accession number: P10253). In certain embodiments, the transgene comprises the UGT1A1 gene (e.g., the human UGT1A1 gene), which encodes bilirubin uridine diphosphate glucuronosyl transferase in humans (UniProtKB accession number: Q5DT03).

Therapeutic agents useful in the disclosed vectors may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

In exemplary embodiments, the rAAV nucleic acid vectors obtained by the disclosed methods may encode at least one diagnostic or therapeutic protein or polypeptide selected from the group consisting of a molecular marker, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinases inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

In certain applications, the rAAV nucleic acid vectors of the present disclosure may comprise one or more nucleic acid segments that encode a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(I87A), viral IL-10, IL-11, IL-12, IL-13, IL-14, IL-15, IL-16, IL-17, IL-18, and any combination thereof.

The rAAV nucleic acid vectors of the present disclosure may optionally further include one or more enhancer sequences that are each operably linked to the nucleic acid segment. Exemplary enhancer sequences include, but are not limited to, one or more selected from the group consisting of a CMV enhancer, a synthetic enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, retinal-specific enhancer and an islet cell-specific enhancer.

Exemplary promoters useful in the practice of the present disclosure include, without limitation, one or more heterologous, tissue-specific, constitutive or inducible promoters, including, for example, but not limited to, a promoter selected from the group consisting of a CMV promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, a retinal-specific promoter, an elafin promoter, a cytokine promoter, an interferon promoter, a growth factor promoter, an $\alpha_1$-antitrypsin promoter, a brain cell-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter, a VP1 6-LexA promoter, or any combination thereof. In exemplary embodiments, the promoter may include a mammalian or avian β-actin promoter.

The vector-encoding nucleic acid segments may also further include one or more post-transcriptional regulatory sequences or one or more polyadenylation signals, including, for example, but not limited to, a woodchuck hepatitis virus post-transcription regulatory element (WPRE), a poly-adenylation signal sequence, or any combination thereof.

In some aspects, the present disclosure concerns geneti-cally-modified, improved-transduction-efficiency rAAV nucleic acid vectors that include at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, conditions, disorders, or diseases. In certain embodiments, the defect may be caused by injury or trauma to the mammal for which treatment is desired. In other embodiments, the defect may be caused the over-expression of an endogenous biological compound, while in other embodiments still; the defect may be caused by the under-expression or even lack of one or more endogenous biological compounds.

The rAAV nucleic acid vectors of the present disclosure may also further optionally include a second distinct nucleic acid segment that comprises, consists essentially of, or consists of, one or more enhancers, one or more regulatory elements, one or more transcriptional elements, or any combination thereof, that alter, improve, regulate, and/or affect the transcription of the nucleotide sequence of interest expressed by the modified rAAV vectors.

For example, the rAAV nucleic acid vectors of the present disclosure may further include a second nucleic acid segment that comprises, consists essentially of, or consists of, a CMV enhancer, a synthetic enhancer, a cell-specific enhancer, a tissue-specific enhancer, or any combination thereof. The second nucleic acid segment may also further comprise, consist essentially of, or consist of, one or more intron sequences, one or more post-transcriptional regulatory elements, or any combination thereof.

The vectors of the present disclosure may also optionally further include a polynucleotide that comprises, consists essentially of, or consists of, one or more polylinkers, restriction sites, and/or multiple cloning region(s) to facilitate insertion (cloning) of one or more selected genetic elements, genes of interest, or therapeutic or diagnostic constructs into the rAAV construct at a selected site within the construct.

The disclosed nucleic acid vectors may be self-comple-mentary (i.e., scrAAV nucleic acid vectors). In other embodiments, the vectors may be single-stranded.

The expression constructs and nucleic acid vectors of the present disclosure may be prepared in a variety of compositions, and may also be formulated in appropriate pharmaceutical vehicles for administration to human or animal subjects.

Host Cells

The present disclosure also concerns host cells that comprise at least one or more of the disclosed virus particles or virions (e.g., virions comprising DE5), or one or more of the disclosed rAAV expression constructs. Such host cells are particularly mammalian host cells, with human host cells being particularly preferred, and may be either isolated, in cell or tissue culture. In the case of genetically modified animal models, the transformed host cells may even be comprised within the body of a non-human animal itself. In some embodiments, the host cells comprise humanized host cells. In particular embodiments, the host cells comprise humanized hepatocytes.

Examples of suitable host cells include hepatocytes, such as H2.35, HUH-7 and HepG2, HEK293 embryonic kidney cells, HeLa cells, Cos cells, U87 cells, KB cells, and Vero cells. In certain embodiments, the modified AAV3B virions of the present disclosure are incorporated into HUH-7 and/or HepG2 cells. In particular embodiments, virions comprising the DE5 variant are incorporated into HUH-7 and/or HepG2 cells.

As described above, the exogenous polynucleotide will preferably encode one or more proteins, polypeptides, peptides, ribozymes, or antisense oligonucleotides, or a combination of these. The exogenous polynucleotide may encode two or more such molecules, or a plurality of such molecules as may be desired. When combinational gene therapies are desired, two or more different molecules may be produced from a single rAAV expression construct, or alternatively, a selected host cell may be transfected with two or more unique rAAV expression constructs, each of which will provide unique transgenes encoding at least two different such molecules.

Use of rAAV Virions in Prophylaxis, Diagnosis, or Therapy

The present disclosure also provides for uses of the compositions disclosed herein as a medicament, or in the manufacture of a medicament, for treating, preventing or ameliorating the symptoms of a disease, disorder, condition, injury or trauma, including, but not limited to, the treatment, prevention, and/or prophylaxis of a disease, disorder or condition, and/or the amelioration of one or more symptoms of such a disease, disorder or condition.

In particular embodiments, the disease, disorder or condition is Wilson's Disease. Wilson's disease is a rare inherited disorder that causes copper to accumulate in vital organs such as the liver. It is an autosomal recessive condition due to a mutation in the ATP7B gene, which encodes a P-type ATPase that transports copper into bile and incorporates it into ceruloplasmin. Left untreated, Wilson's Disease can be fatal.

In some embodiments, the disease, disorder or condition is hemophilia, which is often caused by a mutation in the F8 gene. In other embodiments, the disorder is a lysosomal storage disorder, such as Pompe Disease, which is often caused by a mutation in the GAA gene that encodes the acid alpha-glucosidase enzyme. In other embodiments, the disorder is Crigler-Najjar syndrome. Crigler-Najjar syndrome is often caused by a mutation in the UGT1A1 gene. UGT1A1 provides instructions for making the bilirubin uridine diphosphate glucuronosyl transferase (bilirubin-UGT) enzyme, which is found primarily in liver cells and is necessary for the removal of bilirubin from the body.

In certain embodiments, the creation of recombinant non-human host cells, humanized host cells, and/or isolated recombinant human host cells that comprise one or more of the disclosed rAAV virions (e.g., virions comprising DE5) is also contemplated to be useful for a variety of diagnostic, and laboratory protocols, including, for example, means for the production of large-scale quantities of the virions described herein. Such virus production methods may comprise improvements over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

The present disclosure provides methods of transducing a hepatic cell with a transgene of interest, the method comprising providing to the hepatic cell any of the variant recombinant AAV particles of the disclosure. In some embodiments, the hepatic cell is a human hepatocyte.

Additional aspects of the present disclosure concern methods of use of the disclosed virions, expression constructs, compositions, and host cells in the preparation of medicaments for diagnosing, preventing, treating or ameliorating at least one or more symptoms of a disease, a condition, a disorder, an abnormal condition, a deficiency, injury, or trauma in an animal, and in particular, in a vertebrate mammal, e.g., Wilson's Disease. Such methods generally involve administration to a mammal in need thereof, one or more of the disclosed virions, host cells, compositions, or pluralities thereof, in an amount and for a time sufficient to diagnose, prevent, treat, or lessen one or more symptoms of such a disease, condition, disorder, abnormal condition, deficiency, injury, or trauma in the affected animal. The methods may also encompass prophylactic treatment of animals suspected of having such conditions, or administration of such compositions to those animals at risk for developing such conditions either following diagnosis, or prior to the onset of symptoms.

The present disclosure also provides a method for treating or ameliorating the symptoms of such a disease, injury, disorder, or condition in a mammal. Such methods generally involve at least the step of administering to a mammal in need thereof, one or more of the rAAV virions as disclosed herein, in an amount and for a time sufficient to treat or ameliorate the symptoms of such a disease, injury, disorder, or condition in the mammal. Such treatment regimens are particularly contemplated in human therapy, via administration of one or more compositions either intramuscularly, intravenously, subcutaneously, intrathecally, intraperitoneally, or by direct injection into an organ or a tissue of the mammal under care.

The present disclosure also provides a method for providing to a mammal in need thereof, a therapeutically-effective amount of an rAAV composition of the present disclosure, in an amount, and for a time effective to provide the patient with a therapeutically-effective amount of the desired therapeutic agent(s) encoded by one or more nucleic acid segments comprised within the rAAV virion, e.g., a virion comprising DE5. Exemplary therapeutic agents include, but are not limited to, a polypeptide, a peptide, an antibody, an antigen-binding fragment, a ribozyme, a peptide nucleic acid, an siRNA, an RNAi, an antisense oligonucleotide, an antisense polynucleotide, or a combination thereof.

Because the rAAV capsid variants of the disclosure possess enhanced ability to reduce seroreactivity and evade neutralizing antibodies, the compositions and methods provided herein facilitate the re-dosing or re-administration of an rAAV particle comprising any of the disclosed capsid variants to a subject who has been administered an rAAV particle previously, e.g., as part of a therapeutic regimen. This reduced seroreactivity likewise facilitates the first administration of an rAAV particle to a subject who had exposure to rAAVs previously naively, or outside of the context of a therapeutic regimen. In some embodiments, these subject are human.

Accordingly, the present disclosure provides re-dosing regimens of rAAV. In some aspects of the disclosure, methods of re-administration of rAAV particles (or virions) are provided. Such methods may comprise a first administration, followed by a subsequent (or second) administration of an rAAV particle comprising any of the disclosed capsid variants. In some embodiments, such methods comprise re-administering the recombinant AAV particle or a composition comprising such a particle to the subject, e.g., a human subject in need thereof whom has previously been administered the recombinant AAV particle or the composition.

Pharmaceutical Compositions and Kits

In further aspects, the present disclosure provides compositions comprising one or more of the disclosed rAAV virions (e.g., virions comprising DE5), expression constructs, infectious AAV particles, or host cells. In some embodiments, provided herein are compositions of rAAV virions that further comprise a pharmaceutically acceptable carrier for use in therapy, and for use in the manufacture of medicaments for the treatment of one or more mammalian diseases, disorders, conditions, or trauma (e.g., Wilson's Disease). Such pharmaceutical compositions may optionally further comprise one or more diluents, buffers, liposomes, a lipid, a lipid complex, a microsphere or a nanoparticle.

In some embodiments, the disclosure provides pharmaceutical compositions that comprise a modified rAAV vector as disclosed herein, and further comprise a pharmaceutical excipient, and may be formulated for administration to host cell ex vivo or in situ in an animal, and particularly a human. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Such compositions may be formulated for use in a variety of therapies, such as for example, in the amelioration, prevention, and/or treatment of conditions such as peptide deficiency, polypeptide deficiency, peptide overexpression, polypeptide overexpression, including for example, conditions, diseases or disorders as described herein.

In some embodiments, the number of rAAV particles administered to a subject may be on the order ranging from $10^6$ to $10^{14}$ particles/mL or $10^3$ to $10^{13}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In some embodiments, rAAV particles in an amount of between $10^{11}$ and $4\times10^{12}$ particles/mL are administered. In one embodiment, rAAV particles of higher than $10^{13}$ particles/mL are administered. In some embodiments, the number of rAAV particles administered to a subject may be on the order ranging from $10^6$ to $10^{14}$ vector genomes (vgs)/mL or $10^3$ to $10^{15}$ vgs/mL, or any values there between for either range, such as for example, about $10^6$, $10^7$, $10^8$, $10^9$, $10^{10}$, $10^{11}$, $10^{12}$, $10^{13}$, or $10^{14}$ vgs/mL. In some embodiments, a dose of between $1\times10^{11}$ and $2\times10^{11}$ vgs/ml (or between $5\times10^{10}$ and $1\times10^{11}$ vgs/kg of subject) is administered to the subject. In some embodiments, a dose of between $1\times10^{12}$ and $4\times10^{12}$ vgs/ml (or between $5\times10^{11}$ to $2\times10^{12}$ vgs/kg of the subject) is administered to the subject.

The rAAV particles can be administered as a single dose, or divided into two or more administrations as may be required to achieve therapy of the particular disease or disorder being treated.

In some embodiments, where a second nucleic acid vector encoding the Rep protein within a second rAAV particle is administered to a subject, the ratio of the first rAAV particle to the second rAAV particle is 1:100, 1:50, 1:40, 1:30, 1:20, 1:10, 1:5, 1:2 or 1:1. In some embodiments, the Rep protein is delivered to a subject such that target cells within the subject receive at least two Rep proteins per cell.

In some embodiments, the disclosure provides formulations of compositions disclosed herein in pharmaceutically acceptable carriers for administration to a cell or an animal, either alone or in combination with one or more other modalities of therapy, and in particular, for therapy of human cells, tissues, and diseases affecting man.

If desired, rAAV particle or preparation, Rep proteins, and nucleic acid vectors may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles or preparations, Rep proteins, and nucleic acid vectors may thus be delivered along with various other agents as required in the particular instance. Such compositions may be purified from host cells or other biological sources, or alternatively may be chemically synthesized as described herein.

The formulation of pharmaceutically acceptable carriers is well-known to those of skill in the art, as is the development of suitable dosing and treatment regimens for using the particular compositions described herein in a variety of treatment regimens, including e.g., oral, parenteral, intravenous, intranasal, intra-articular, and intramuscular administration and formulation.

Typically, these formulations may contain at least about 0.1% of the therapeutic agent (e.g., rAAV particle or preparation, Rep protein, and/or nucleic acid vector) or more, although the percentage of the active ingredient(s) may, of course, be varied and may conveniently be between about 1% or 2% and about 70% or 80% or more of the weight or volume of the total formulation. Naturally, the amount of therapeutic agent(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV particles or preparations, Rep proteins, and/or nucleic acid vectors in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection.

The pharmaceutical forms of the compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The pharmaceutical compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Ed., 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles or preparations, Rep proteins, and/or nucleic acid vectors, in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Ex vivo delivery of cells transduced with rAAV particles or preparations, and/or Rep proteins is also contemplated herein. Ex vivo gene delivery may be used to transplant rAAV-transduced host cells back into the host. A suitable ex vivo protocol may include several steps. For example, a segment of target tissue or an aliquot of target fluid may be harvested from the host and rAAV particles or preparations, and/or Rep proteins may be used to transduce a nucleic acid vector into the host cells in the tissue or fluid. These genetically modified cells may then be transplanted back into the host. Several approaches may be used for the reintroduction of cells into the host, including intravenous injection, intraperitoneal injection, or in situ injection into target tissue. Autologous and allogeneic cell transplantation may be used according to the invention.

The amount of rAAV particle or preparation, Rep protein, or nucleic acid vector compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle or preparation, Rep protein, or nucleic acid vector compositions, either over a relatively short, or a relatively prolonged period of time, as may be determined by the medical practitioner overseeing the administration of such compositions.

Toxicity and efficacy of the compositions utilized in methods of the disclosure can be determined by standard pharmaceutical procedures, using either cells in culture or experimental animals to determine the $LD_{50}$ (the dose lethal to 50% of the population). The dose ratio between toxicity and efficacy the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an $ED_{50}$ with little or no toxicity. The dosage may vary within this range depending upon the dosage form employed and the route of administration utilized.

The present disclosure provides compositions including one or more of the disclosed rAAV virions (e.g., virions comprising DE5) comprised within a kit for diagnosing, preventing, treating or ameliorating one or more symptoms of a mammalian disease, injury, disorder, trauma or condition. In some embodiments, the disease or disorder is Wilson's Disease. Such kits may also be useful in the diagnosis, prophylaxis, and/or therapy or a human disease, and may be particularly useful in the treatment, prevention, and/or amelioration of one or more symptoms of Wilson's Disease, wet age-related macular degeneration, dry age-related macular degeneration, glaucoma, retinitis pigmentosa, diabetic retinopathy, orphan ophthalmological diseases, cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory condition, stroke, ischemia, alpha 1-antitrypsin (AAT) deficiency, Transthyretin-Related Familial Amyloid Polyneuropathy, Ornithine Transcarbamylase Deficiency, Batten's disease, Alzheimer's disease, sickle cell disease, β-thalassemia, Huntington's disease, Parkinson's disease, skeletal disease, trauma, pulmonary disease in a human.

Kits comprising one or more of the disclosed rAAV virions, transformed host cells or pharmaceutical compositions comprising such vectors; and instructions for using such kits in one or more therapeutic, diagnostic, and/or prophylactic clinical embodiments are also provided by the present disclosure. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, condition, and/or injury, or may include components for the large-scale production of the viral vectors themselves, such as for commercial sale, or for use by others, including e.g., virologists, medical professionals, and the like.

Methods of Making rAAV3B Particles

Various methods of producing rAAV particles (e.g., particles comprising DE5) and nucleic acid vectors are known (see, e.g., Zolotukhin et al. *Methods* 28 (2002) 158-167; and U.S. Patent Publication Nos. US 2007/0015238 and US 2012/0322861, each of which are incorporated herein by reference; and plasmids and kits available from ATCC and Cell Biolabs, Inc.). In some embodiments, a vector (e.g., a plasmid) comprising a transgene of interest may be combined with one or more helper plasmids, e.g., that contain a rep gene (e.g., encoding Rep78, Rep68, Rep52 and Rep40) and a cap gene (encoding VP1, VP2, and VP3, including a modified VP region as described herein), and transfected into a recombinant cells, called helper or producer cells, such that the nucleic acid vector is packaged or encapsidated inside the capsid and subsequently purified.

Non-limiting examples of mammalian helper cells include HEK293 cells, COS cells, HeLa cells, BHK cells, or CHO cells (see, e.g., ATCC® CRL-1573TM, ATCC® CRL-1651™, ATCC® CRL-1650™, ATCC® CCL-2, ATCC® CCL-10™, or ATCC® CCL-61™). A non-limiting example of an insect helper cells is Sf9 cells (see, e.g., ATCC® CRL-1711™). A helper cell may comprises rep and/or cap genes that encode the Rep protein and/or Cap proteins. In some embodiments, the packaging is performed in vitro (e.g., outside of a living organism).

In some embodiments, a nucleic acid vector (e.g., a plasmid) containing the transgene of interest (e.g., ATP7B) is combined with one or more helper plasmids, e.g., that contain a rep gene of a first serotype and a cap gene of the same serotype or a different serotype, and transfected into helper cells such that the rAAV particle is packaged. In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG(R484E/R585E), and pDP8. ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, J. Virol., Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), *J Virology*, 6:3096-3101).

Inverted terminal repeat (ITR) sequences and plasmids containing ITR sequences are known in the art and are commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, et al., Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/ 1-59259-304-6:201 © Humana Press Inc. 2003. Chapter 10. Targeted Integration by Adeno-Associated Virus. Matthew D. Weitzman et al.; U.S. Pat. Nos. 5,139,941 and 5,962,313, all of which are incorporated herein by reference).

Genbank reference numbers for sequences of AAV serotype 3B are listed in patent publication WO 2012/064960, which is incorporated herein by reference in its entirety.

A non-limiting method of rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes, cap genes, and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. As an example, HEK293 cells (available from ATCC®) are transfected via CaPO$_4$-mediated transfection, lipids or polymeric molecules such as Polyethylenimine (PEI) with the helper plasmid(s) and a plasmid containing a nucleic acid vector. The HEK293 cells are then incubated for at least 60 hours to allow for rAAV particle production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus (e.g., Ad5) and herpesvirus.

Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation. See US Patent Publication No. 2017/0130208, incorporated herein by reference.

Methods for large-scale production of AAV using a herpesvirus-based system are also known. See for example, Clement et al. (*Hum Gene Ther.* 2009, 20(8):796-806).

Methods of producing exosome-associated AAV, which can be more resistant to neutralizing anti-AAV antibodies, are also known (Hudry et al., Gene Ther. 2016, 23(4):380-92; Macguire et al., *Mol Ther.* 2012, 20(5):960-71).

Methods for producing and using pseudotyped rAAV vectors are also known in the art (see, e.g., Duan et al., J. Virol., 75:7662-7671, 2001; Halbert et al., *J. Virol.,* 74:1524-1532, 2000; Zolotukhin et al., *Methods,* 28:158-167, 2002; and Auricchio et al., *Hum. Molec. Genet.,* 10:3075-3081, 2001).

Illustrative embodiments of the present disclosure are described below. In the interest of clarity, not all features of an actual implementation are described in this specification. It will be appreciated by one of skill in the art that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Exemplary Definitions

Unless otherwise defined, all technical terms used herein have the same meaning as commonly understood by one of ordinary skill in the art to which this present disclosure belongs. Commonly understood definitions of molecular biology terms can be found in Rieger et al., (1991) and Lewin (1994). Commonly understood definitions of virology terms can be found in Granoff and Webster (1999) and Tidona and Darai (2002).

In accordance with convention, the words "a" and "an" when used in this application, including the claims, denotes "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof, that is pharmaceutically acceptable for administration to the relevant animal. The use of one or more delivery vehicles for chemical compounds in general, and chemotherapeutics in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed chemotherapeutic compositions.

The term "e.g.," as used herein, is used merely by way of example, without limitation intended, and should not be construed as referring only those items explicitly enumerated in the specification.

As used herein, "an effective amount" would be understood by those of ordinary skill in the art to provide a therapeutic, prophylactic, or otherwise beneficial effect against the organism, its infection, or the symptoms of the organism or its infection, or any combination thereof.

The phrase "expression control sequence" refers to any genetic element (e.g., polynucleotide sequence) that can exert a regulatory effect on the replication or expression (transcription or translation) of another genetic element. Common expression control sequences include promoters, polyadenylation (polyA) signals, transcription termination sequences, upstream regulatory domains, origins of replication, internal ribosome entry sites (IRES), enhancers, and the like. A "tissue specific expression control sequence" is one that exerts a regulatory effect on the replication or expression (transcription or translation) of another genetic element in only one type of tissue or a small subset of tissues.

The phrase "helper function" is meant as a functional activity performed by a nucleic acid or polypeptide that is derived from a virus such as Adenovirus (Ad) or herpesvirus and that facilitates AAV replication in a host cell.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity may be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetic ally).

As used herein, the terms "humanize" and "humanized" refers to the action of engrafting human cells or tissues into a non-human animal, such as a mouse. The present disclosure may refer to humanized murine models and/or subjects, such as mouse models humanized with primary human hepatic cells.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

As used herein, the term "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The terms "isolated" or "biologically pure" refer to material that is substantially, or essentially, free from components that normally accompany the material as it is found in its native state. Thus, isolated polynucleotides in accordance with the present disclosure preferably do not contain materials normally associated with those polynucleotides in their natural, or in situ, environment.

As used herein, the term "kit" may be used to describe variations of the portable, self-contained enclosure that includes at least one set of components to conduct one or more of the diagnostic or therapeutic methods of the present disclosure.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "library" refers to a collection of elements that differ from one another in at least one aspect. For example, a vector library is a collection of at least two vectors that differ from one another by at least one nucleotide. As another example, a "virion library" is a collection of at least two virions that differ from one another by at least one nucleotide or at least one capsid protein.

As used herein, the term "master library" or "combined library" refers to a pool of rAAV virions composed of chimeric rcAAV nucleic acid vectors encapsidated in cognate chimeric capsids (e.g., capsids containing a degenerate or otherwise modified Cap protein). As used herein, the term "rcAAV nucleic acid vector" refers to a replication-competent AAV-derived nucleic acid capable of DNA replication in a cell without any additional AAV genes or gene products.

As used herein, the term "parent sub-library" refers to a pool of rAAV virions composed of chimeric rcAAV nucleic acid vectors encapsidated in cognate chimeric capsids (e.g., capsids containing degenerate or otherwise modified Cap protein). More than one parent sub-library may be combined to create a master library or combined library.

When referring to a nucleic acid molecule or polypeptide, the term "native" refers to a naturally-occurring (e.g., a WT) nucleic acid or polypeptide.

The terms "naturally-occurring" or "native," as used herein refers to the fact that the described molecule may be found in nature. For example, a polypeptide or polynucleotide sequence that is present in an organism (including viruses) that may be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, the phrase "nucleic acid" means a chain of two or more nucleotides such as RNA (ribonucleic acid) and DNA (deoxyribonucleic acid). Conventional nomenclature exists in the art for polynucleotide and polypeptide structures. For example, one-letter abbreviations are widely employed to describe nucleotides: Adenine (A), Guanine (G), Cytosine (C), Thymine (T), Uracil (U), Purine, i.e. A or G (R), Pyrimidine, i.e. C or T (Y), any nucleotide (N), Weak, i.e. A or T (W), Strong, i.e. G or C (S), Amino, i.e. A or C (M), Keto, i.e. G or T (K), not A, i.e. G or C or T (B), not G, i.e. A or C or T (H), not C, i.e. A or G or T (D) and not T, i.e. A or G or C (V).

In accordance with the present disclosure, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

The phrases "cap nucleic acid," "cap gene," and "capsid gene" as used herein mean a nucleic acid that encodes a Cap protein. Examples of cap nucleic acids include "wild-type" (WT) Cap-encoding nucleic acid sequences from AAV serotypes 1, 2, 3, 4, 5, 6, 7, 8, 9, 10, 11, 12, 13; a native form cap cDNA; a nucleic acid having sequences from which a cap cDNA can be transcribed; and/or allelic variants and homologs of the foregoing.

"VR", "VRs", "variable region" or "variable regions" refer to amino acid stretches of capsid protein that do not have a high degree of homology between AAV variants. These amino acid stretches are commonly designated as VRs I through IX (also known as "loops"). VRs are localized at the surface of the assembled capsid and interact with host cell surface receptors and other host factors.

The phrase "pharmaceutically acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

As used herein, the term "plasmid" or "vector" refers to a genetic construct that is composed of genetic material (i.e., nucleic acids). Typically, a plasmid or a vector contains an origin of replication that is functional in bacterial host cells, e.g., Escherichia coli, and selectable markers for detecting bacterial host cells including the plasmid. Plasmids and vectors of the present disclosure may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Additional conventions include: Asn or Asp (B; Asx), Gln or Glu (Z; Glx), Leu or Ile (J; Xle), Selenocysteine (U; Sec), Pyrrolysine (O; Pyl) and Unknown (X; Unk). Amino acid residues described herein are preferred to be in the "L" isomeric form. However, residues in the "D" isomeric form may be substituted for any L-amino acid residue provided the desired properties of the polypeptide are retained.

The term "promoter," as used herein refers to a region or regions of a nucleic acid sequence that regulates transcription.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from two to about 20 amino acid residues in length, oligopeptides from about 10 to about 100 amino acid residues in length, and longer polypeptides including those of about 100 or more amino acid residues in length. Furthermore, the term is also intended to include enzymes, i.e., functional biomolecules including at least one amino acid polymer. Polypeptides and proteins of the present disclosure also include polypeptides and proteins that are or have been post-translationally modified, and include any sugar or other derivative(s) or conjugate(s) added to the backbone amino acid chain.

The term "pseudotyped" is meant a nucleic acid or genome derived from a first AAV serotype that is encapsidated (packaged) into an AAV capsid containing at least one AAV Cap protein of a second serotype differing from the first serotype.

The term "recombinant" indicates that the material (e.g., a polynucleotide or a polypeptide) has been artificially or synthetically (non-naturally) altered by human intervention. The alteration may be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75% sequence identity as compared to a selected reference nucleic acid or amino acid sequence. More typically, the selected sequence and the reference sequence will have at least about 80, 81, 82, 83, 84 or even 85% sequence identity, and more preferably, at least about 86, 87, 88, 89, 90, 91, 92, 93, 94, or 95% sequence identity. More preferably still, highly homologous sequences often share greater than at least about 96, 97, 98, or 99% sequence identity between the selected sequence and the reference sequence to which it was compared.

The percentage of sequence identity may be calculated over the entire length of the sequences to be compared, or may be calculated by excluding small deletions or additions which total less than about 25% or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

As used herein, the term "structural gene" is intended to generally describe a polynucleotide, such as a gene, that is expressed to produce an encoded peptide, polypeptide, protein, ribozyme, catalytic RNA molecule, or antisense molecule.

As used herein, the term "spheroid" refers to a three-dimensional spherical cellular aggregate culture model. Spheroids (e.g., hepatospheres) may better simulate a live cell's environmental conditions compared to a two-dimensional culture model, specifically with respect to reactions between cells.

The term "subject," as used herein, describes an organism, including a mammal such as a human primate, to which treatment with one or more of the disclosed compositions may be provided. Mammalian species that may benefit from the disclosed treatment methods include, without limitation, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like. The term "host" refers to any host organism that may receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner.

As used herein, the terms "terminal repeat" or "TR" mean a nucleic acid sequence derived from an AAV that is required in cis for replication and packaging of AAV.

"Transcriptional regulatory element" refers to a polynucleotide sequence that activates transcription alone or in combination with one or more other nucleic acid sequences. A transcriptional regulatory element may include, for example, one or more promoters, one or more response elements, one or more negative regulatory elements, one or more enhancers, or any combination thereof.

As used herein, a "transcription factor recognition site" and a "transcription factor binding site" refer to a polynucleotide sequence(s) or sequence motif(s) that are identified as being sites for the sequence-specific interaction of one or more transcription factors, frequently taking the form of direct protein-DNA binding. Typically, transcription factor binding sites may be identified by DNA footprinting, gel mobility shift assays, and the like, and/or may be predicted based on known consensus sequence motifs, or by other methods known to one of ordinary skill in the relevant molecular biological and virology arts.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral particle, a plasmid, or a recombinant DNA or RNA molecule) into a host cell or protoplast in which the exogenous polynucleotide is incorporated into at least a first chromosome or is capable of autonomous replication within the transformed host cell.

Transfection, electroporation, and "naked" nucleic acid uptake all represent examples of techniques used to transform a host cell with one or more polynucleotides.

As used herein, the terms "treat," "treating," and "treatment" refer to the administration of a composition to reduce the frequency or severity of at least one sign or symptom of a disease, disorder or condition experienced by a subject. These terms embrace prophylactic administration, i.e., prior to the onset of clinical symptoms of a disease state so as to prevent any symptom, aspect or characteristic of the disease state. The disclosed compositions may be administered to a subject in an effective amount, that is, an amount capable of producing a desirable result. The desirable result will depend upon the active agent being administered. For example, an effective amount of a rAAV particle may be an amount of the particle that is capable of transferring a heterologous nucleic acid to a host organ, tissue, or cell. In some embodiments, the disease, disorder or condition is Wilson's Disease. Such treating need not be absolute to be deemed medically useful. As such, the terms "treatment," "treat," "treated," or "treating" may refer to therapy, or the amelioration or reduction in the extent or severity of disease, disorder or condition, of one or more symptom thereof, whether before or after onset of the disease, disorder or condition.

As used herein, the term "vector" refers to a nucleic acid molecule capable of transporting another nucleic acid to which it has been linked, e.g., a plasmid. One type of preferred vector is an episome, i.e., a nucleic acid capable of extra-chromosomal replication. Preferred vectors are those capable of autonomous replication and/or expression of nucleic acids to which they are linked. An "rAAV nucleic acid vector" is a recombinant AAV-derived nucleic acid containing at least one terminal repeat (TR) sequence.

The use of "virion" is meant to describe a virus particle that contains a nucleic acid and a protein coat (capsid). An "rAAV virion" is a virion that includes nucleic acid sequences and/or proteins derived from a rAAV expression construct.

As used herein, the term "tropism" refers to the cells and/or tissues of a host which support growth of a particular serotype of AAV. Some serotypes may have a broad tissue tropism and can infect many types of cells and tissues. Other serotypes may infect primarily a single tissue or cell type.

As used herein, the term "variant" refers to a molecule (e.g., a capsid protein) having characteristics that deviate from what occurs in nature, e.g., a "variant" is at least about 80% identical, at least about 90% identical, at least about 95% identical, at least about 96% identical, at least about 97% identical, at least about 98% identical, at least about 99% identical, at least about 99.5% identical, or at least about 99.9% identical to the wild type capsid. Variants of a protein molecule, e.g., a capsid, may contain modifications to the amino acid sequence (e.g., having 1, 2, 3, 4, 5, 6, 7, 8, 9, 10, 10-15, or 15-20 amino acid substitutions) relative to the wild type protein sequence, which arise from point mutations installed into the nucleic acid sequence encoding the capsid protein. These modifications include chemical modifications as well as truncations.

By a protein (e.g., a capsid protein) comprising an amino acid sequence having at least, for example, 95% "identity" to a query amino acid sequence, it is intended that the amino sequence of the subject amino acid molecule is identical to the query sequence except that the subject amino acid molecule sequence may include up to five amino acid alterations per each 100 amino acids of the query sequence. In other words, to obtain a capsid having an amino sequence at least 95% identical to a reference (query) sequence, up to 5% of the amino acids in the subject sequence may be inserted, deleted, or substituted with another nucleotide. These alterations of the reference sequence may occur at the N- or C-terminus of the reference sequence or anywhere between those positions, interspersed either individually among amino acids in the reference sequence or in one or more contiguous groups within the reference sequence.

As a practical matter, whether any particular amino acid molecule is at least 80%, 85%, 90%, 95%, 96%, 97%, 98%, or 99% identical to, for instance, the amino acid sequence of a capsid protein, can be determined conventionally using known computer programs. A preferred method for determining the best overall match between a query sequence (e.g., a sequence of the present disclosure) and a subject sequence, also referred to as a global sequence alignment, can be determined using the FASTDB or blastn computer program based on the algorithm of Brutlag et al. (*Comp. App. Biosci.* 6:237-245 (1990)). In a sequence alignment the query and subject sequences are either amino acid sequence or both amino acid sequences. The result of said global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Whether a nucleotide is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present disclosure. For subject sequences truncated at the N- or C-terminus, relative to the query sequence, the percent identity is corrected by calculating the number of nucleotides of the query sequence that are positioned N- or C-terminus to the query sequence, which are not matched/ aligned with a corresponding subject nucleotide, as a percent of the total bases of the query sequence.

EXAMPLES

The following examples are included to demonstrate illustrative embodiments of the present disclosure. It should be appreciated by those of ordinary skill in the art that the techniques disclosed in these examples represent techniques discovered to function well in the practice of the present disclosure, and thus can be considered to constitute preferred modes for its practice. However, those of ordinary skill in the art should, in light of the present disclosure appreciate that many changes may be made in the specific embodiments which are disclosed and still obtain a like or similar result without departing from the spirit and scope of the present disclosure.

Strategies to improve AAV capsid design include (a) rational approach of mutagenizing known capsid residues critical for binding, entry, and/or intracellular trafficking, and (b) directed evolution to rapidly introduce molecular modifications into the AAV capsids, thus manipulating both diversity and selection. Using detailed knowledge of AAV capsid structures and the sequence of 150 naturally occurring AAV3 variants, a combinatorial capsid library was derived whereby only variable regions (VRs) on the surface of virion are modified.

Example 1

AAV Library Generation

The AAV icosahedral capsid is composed of three structural proteins (VP1, VP2, and VP3), of which, VP2 and VP3 are N-terminal truncated versions of VP127. VP3 is the most abundant capsid subunit, comprising a major part of the capsid surface, and hence the major determinant of antigenicity and cell tropism. The structure of VP3 contains a β-barrel core, with homologous β-strands linked by 9 highly variable extended loops called variable regions (VR-I to IX)[28]. Because of their surface location, VRs are predicted to be less critical for capsid assembly but essential for determining cell tropism and antigenicity[29]. For this study, a replication competent AAV3B capsid library was generated by modifying only surface VRs while keeping the backbone sequence unchanged to maintain the integrity of the assembling scaffold. 150 AAV naturally occurring variants in the AAV3B background were aligned as described earlier for AAV2[21], and out of all candidate positions for mutagenesis, residues that were clearly exposed to the surface were selected for modification. Only VR-I [amino acid (aa) residues 263-267 of the AAV3B VP1], VR-IV (aa 450-462), VR-V (aa 491-508), VR-VI (aa 528-533) and VR-VII (aa 546-557) were diversified, because mutagenizing other loops has been previously shown to be detrimental to the library's assembly and complexity[21]. In addition, each aa residue substitution was restricted to a subset of residues naturally occurring in this particular position when 150 wt serotypes are aligned as described by Marsic et al.[21]. Even with the described restrictions, the probabilistic sequence space (also known as theoretical complexity) would amount to $1.29 \times 10^{31}$ possible permutations, thus exceeding the practical limit of library design. To reduce the complexity and the occurrence of the potential dead-end variants, an approach of a stepwise structural selection library construction, as detailed below, was applied.

Figure 15:
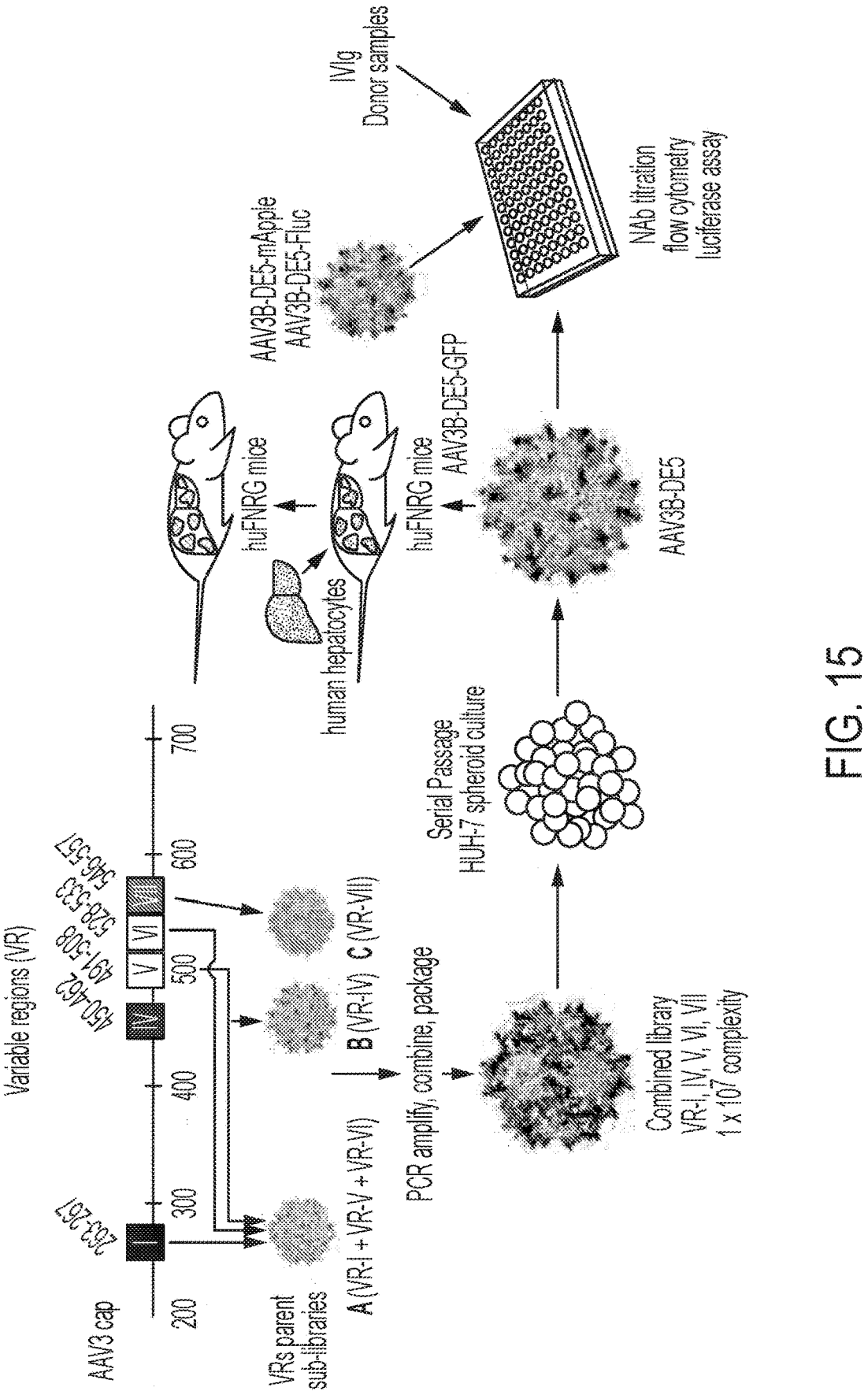
FIG. 15 shows the steps of the integrated approach taken by the inventors to generate and evaluate novel AAV3B variants. By integrating a combinatorial AAV3B capsid library platform with directed evolution in a hepatocellular carcinoma (HUH-7) cell line, they isolated candidate AAV3B-DE5. DE5 exhibited improved tropism in human hepatocytes (e.g., in humanized huFNRG mice) and reduced seroreactivity to preexisting AAV neutralizing antibodies in human serum and pooled intravenous immunoglobulin (IVIg).

First, the following sub-libraries were constructed (FIG. 15): A (VR-I+VR-V+VR-VI), B (VR-IV) and C (VR-VII). These three sub-libraries were constructed from overlapping synthetic oligonucleotides by PCR and isothermal DNA assembly, packaged, and purified separately to select structurally compatible parent viral sub-libraries (FIG. 15, Step 1). Next, using viral DNAs as PCR templates, the VRs from the sub-libraries A, B, and C were amplified and combined in one ABC library incorporating diversified I, IV, V, VI, and VII loops (FIG. 15, Step 2). A total of $2.5 \times 107$ plasmid molecules (extrapolated from colony counts) successfully contributed to creating the plasmid library, which was then used for large scale packaging of the final viral library. Steps 1 and 2 are described in further detail below.

Step 1: Sub-Libraries Assembly.

Using the plasmid pITR3-R3C3-AatII as a template, the following ten PCR reactions were conducted:

| Primers | PCR fragment size |
|---|---|
| A3CL-A (VRs-I, V, VI): | |
| 1. A3CL-F + A3CL-A1R (before VR-I) | 86 bp |
| 2. A3CL-A1F + A3CL-A2R (VR-I to most of VR-V) | 747 bp |
| 3. A3CL-A2F + A3CL-A3R (part of VR-V to VR-VI) | 136 bp |
| 4. A3CL-A3F + A3CL-R (after VR-VI) | 281 bp |

-continued

| Primers | PCR fragment size |
|---|---|
| A3CL-B (VR-IV): | |
| 5. A3CL-F + A3CL-B1R (before VR-IV) | 647 bp |
| 6. A3CL-B1F + A3CL-R (VR-IV to end) | 556 bp |
| A3CL-C (VR-VII): | |
| 7. A3CL-F + A3CL-C1R (before VR-VII) | 935 bp |
| 8. A3CL-C1F + A3CL-R (VR-VII to end) | 266 bp |
| A3CL-D (VR-VIII): | |
| 9. A3CL-F + A3CL-D1R (before VR-VIII) | 1055 bp |
| 10. A3CL-D1F + A3CL-R (VR-VIII to end) | 147 bp |

The respective PCR fragments were eluted from the agarose gel, mixed at equimolar ratios as indicated above for sub-libraries A, B, C, and D, and subjected to 15 cycles of overlap extension (OE) without primers, followed by 20 cycles of PCR using A3CL-F forward and A3CL-R reverse primers. The resulting fragments of 1140 bp for each of the A (I+V+VI), B (IV), C (VII), or D (VIII) sub-libraries were purified on agarose gel and eluted in small volume H2O. Using isothermal DNA assembly protocol, the respective fragments were individually sub-cloned into gel-purified pTR3-R3C3-AatII digested with AatII+ApaI. Four plasmid libraries A, B, C, and D, incorporating the respective VRs were derived. The estimated plasmid libraries' complexities were the following: A—$4.4 \times 10^7$; B—$1.7 \times 10^7$; C—$1 \times 10^8$; D—$1 \times 10^8$.

Step 2: Pre-Selecting Structurally Compatible Parent Viral Libraries.

Using plasmid libraries from Step 1, viral sub-libraries A, B, C, and D were packaged, AAV virus from each preparation was purified using iodixanol density gradients, and the viral DNAs were isolated. Next, using viral DNAs as templates, the following PCR reactions were conducted:

1. VR-I, primers A3CL-F+VR-I_IV-R, template A, size 644 bp.

2. VR-IV, primers VR-I_IV-F+VR-IV_V-R, template B, size 145 bp.

3. VR-V+VI, primers VR-IV_V-F+VR-VI_VII-R, template A, size 194 bp.

4. VR-VII, primers VR-VI_VR-VII-F+A3CL-R, template C, size 274 bp.

5. VR-VIII, primers A3CL-F and A3CL-R, template D, size 1140 bp.

The respective PCR fragments were gel-purified and used as the templates in the OE/PCR to derive two PCR fragments, each of 1140 bp: A+B+C (VR-I, IV, V, VI, VII) and D (VR-VIII).

Step 3: Packaging Master Libraries.

Figure 5:
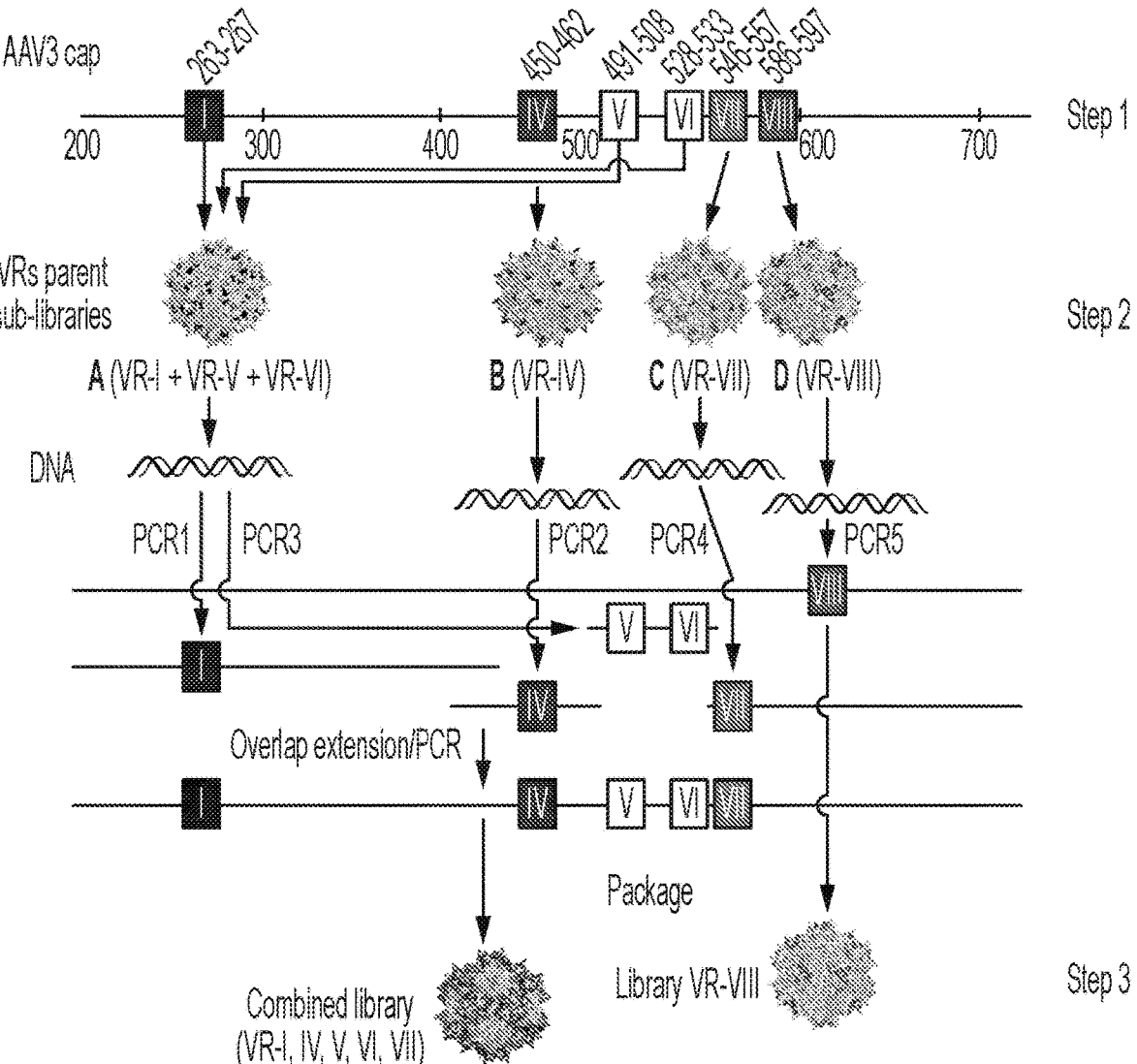
FIG. 5 is a flowchart illustrating design and construction of AAV3B (A3CL) combinatorial capsid libraries ABC and D. Step 1: Sub-libraries A, B and C were first assembled, each with mutations in different regions (VR-I, VR-V, VR-VI for A; VR-IV for B; VR-VII for C; and VR-VIII for D). Step 2: variable regions from the 3 sub-libraries (from DNA isolated from successfully assembled AAV particles) were recombined to generate the final library that has mutations in all 5 regions. Step 3: the plasmid library is packaged into the viral library.

Using isothermal DNA assembly protocol, the respective fragments were individually sub-cloned into gel-purified pTR3-R3C3-AatII digested with AatII+ApaI. The estimated plasmid library A+B+C complexity was $2.5 \times 10^7$, plasmid library D complexity was $4 \times 10^7$. Using these plasmid libraries, two final master viral libraries were packaged: ABC, with the titer of $5.7 \times 10^{12}$ DNase resistant particles per milliliter (DRP/ml), and D, with the titer of $8.7 \times 10^{12}$ DRP/ml. The assembly flowchart is shown in FIG. 5.

TABLE 1

Theoretical (calculated) complexities of A3CL for individual VRs and combinations of VRs. The VRs and VRs combinations constructed as sub-libraries are shown in bold font.

| VR | Complexity |
|---|---|
| I | 72 |
| IV | $2.1 \times 10^6$ |
| V | 27,648 |
| VI | 144 |
| VII | $4 \times 10^7$ |
| VIII | $5.44 \times 10^8$ |
| I + V | $1.99 \times 10^6$ |
| I + VI | $1.04 \times 10^4$ |
| I + V + VI | $2.87 \times 10^8$ |
| V + VI | $3.98 \times 10^6$ |

TABLE 1-continued

Theoretical (calculated) complexities of A3CL for individual VRs and combinations of VRs. The VRs and VRs combinations constructed as sub-libraries are shown in bold font.

| VR | Complexity |
|---|---|
| I + IV + V + VI + VII | $2.37 \times 10^{22}$ |
| I + IV + V + VI + VII + VIII | $1.29 \times 10^{31}$ |

TABLE 2

Theoretical (calculated) complexities of constructed sub-libraries A, B, C and D.

| Sub-library | VRs | Complexity |
|---|---|---|
| A3CL-A | I – V – VI | $2.9 \times 10^8$ |
| A3CL-B | IV | $2 \times 10^6$ |
| A3CL-C | VII | $4 \times 10^7$ |
| A3CL-D | VIII | $5.4 \times 10^8$ |

TABLE 3

Synthetic oligonucleotides used to assemble the AAV3B capsid library

| Name | Sequence |
|---|---|
| A3CL-F | GGCTGGGCGACAGAGTCATC (SEQ ID NO: 10) |
| A3CL-A1R | GCTGGAGATTTGCTTGTAGAGATG (SEQ ID NO: 11) |
| A3CL-A1F | CATCTCTACAAGCAAATCTCCAGCVVMDCAGGAGCTASCAACGACAACCACTACTTTGGC (SEQ ID NO: 12) |
| A3CL-A2R | CCAAGGAAASTYACTGTTGTTGTTSYSGBYGKVGRYTKTTGAAAGTCTCTGTTGCC (SEQ ID NO: 13) |
| A3CL-A2F | AACAACAACAGTRASTTTCCTTGGMCAGCGGCCAGCAMATATCATCTCAATG (SEQ ID NO: 14) |
| A3CL-A3R | GATTGCCGTGCATAGGGAAAAATYTSYCSKYATCGTCCYYGTGACTGGCCATAGCTGG (SEQ ID NO: 15) |
| A3CL-A3F | ATTTTTCCCTATGCACGGCAATC (SEQ ID NO: 16) |
| A3CL-R | CATCCGIGTGAGGAATCTTTGC (SEQ ID NO: 17) |
| A3CL-B1R | TTGCGTTCTGTTCAGGTAGTACAGA (SEQ ID NO: 18) |
| A3CL-B1F | CTGTACTACCTGAACAGAACGCAARGCAMCVCNRGCGGAACARCCRVCMHSMRSVVSCTGVNGTTTAGCCAGGCTGGGCC (SEQ ID NO: 19) |
| A3CL-C1R | TTTGCCAAATATTAGATTGCC (SEQ ID NO: 20) |
| A3CL-C1F | CGGCAATCTAATATTTGGCAAASAARRCRSCRVSRVARVCRATRYCGMSDWCGRSVRSGTAATGATTACGGATGAAGAAG (SEQ ID NO: 21) |
| A3CL-D1R | CTGCAAGTTATTTGCCACAGTTC (SEQ ID NO: 22) |
| A3CL-D1F | GAACTGTGGCAAATAACTTGCAGRVSVVSMRSRVCVVSCCCACGDHTVVSRNSGTCVMSCATCAGGGGGCCTTACCTG (SEQ ID NO: 23) |
| VR-I_IV-F | CAGTATCTGTACTACCTGAACAGAACGC (SEQ ID NO: 24) |
| VR-I_IV-R | GCGTTCTGTTCAGGTAGTACAGATACTG (SEQ ID NO: 25) |
| VR-IV_V-F | CCTGGGCCCTGCTACCGGCAACAGAG (SEQ ID NO: 26) |
| VR-IV_V-R | CTCTGTTGCCGGTAGCAGGGCCCAGG (SEQ ID NO: 27) |
| VR-VI_VII-F | CCCTATGCACGGCAATCTAATATTIGGC (SEQ ID NO: 28) |
| VR-VI_VII-R | GCCAAATATTAGATTGCCGTGCATAGGG (SEQ ID NO: 29) |

AAV Library Characterization

Figures 16A, 16B:
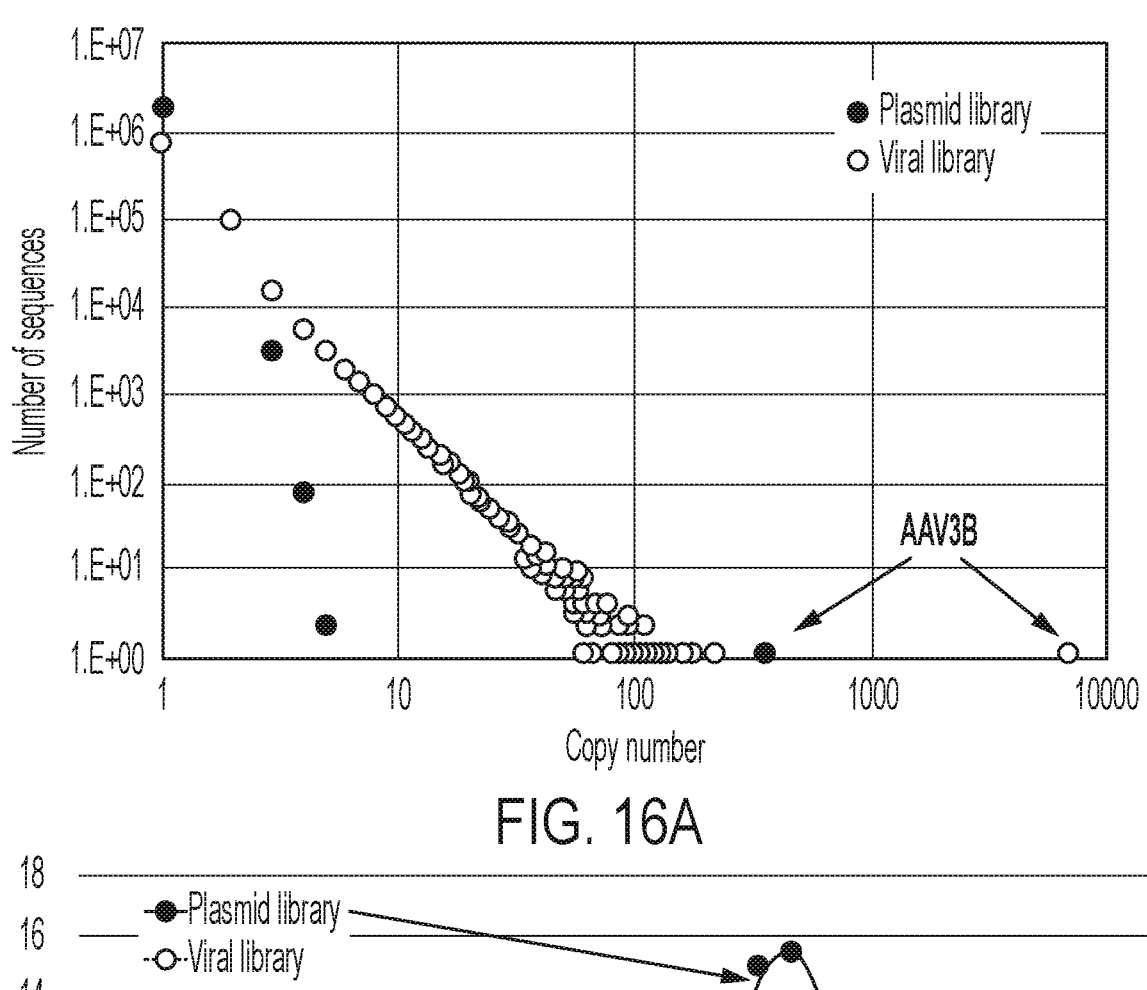
FIGS. 16A-16C show NGS analysis of plasmid and viral AAV libraries.
Figure 16C:
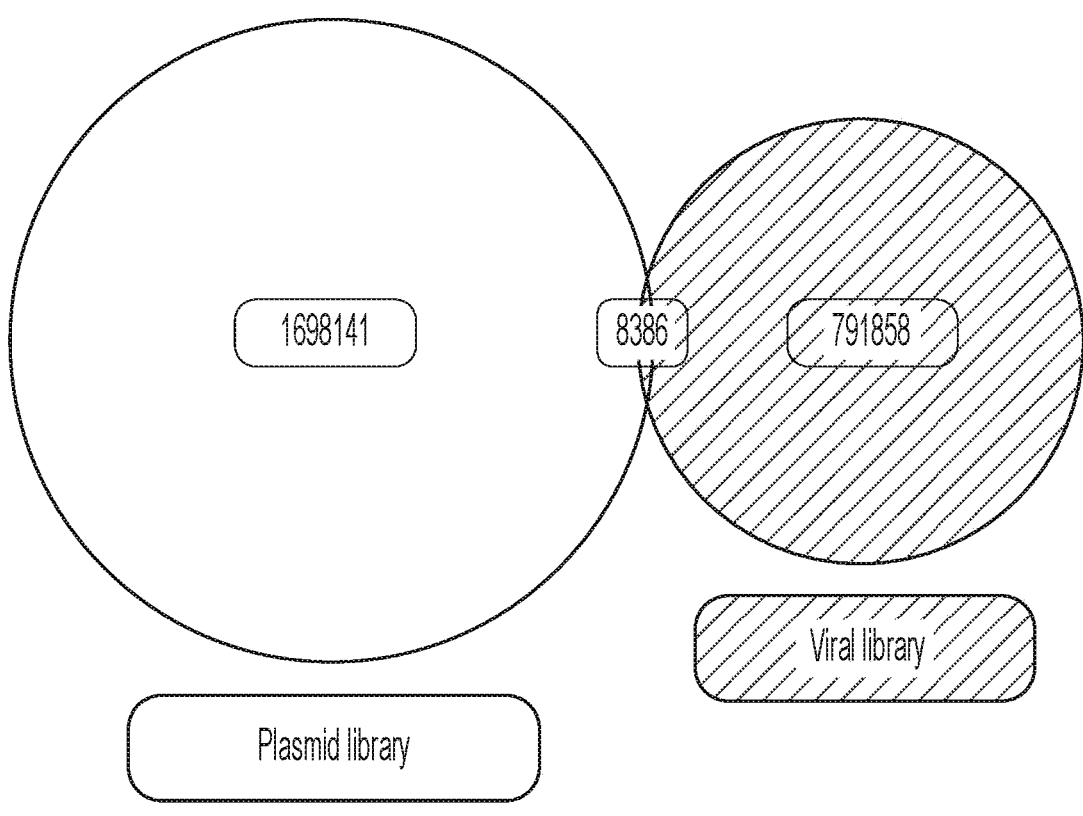

Both plasmid and viral libraries were subjected to Next-Generation Sequencing (NGS). The Illumina platform was chosen because of its higher throughput and lower error rate than PacBio. Due to read length limits, a 393-nucleotide region encompassing VR-IV to VR-VII only (34 of the total 37 diversified amino acid positions) was sequenced from both ends. Reads were subjected to a high stringency filtering to remove sequencing errors and translated into protein sequences. All calculations were performed on the variable regions only of the filtered protein sequences (results shown in Table 1 and FIGS. 16A-16C). A limited sequence bias increase between plasmid and viral libraries was observed (FIG. 16A), resulting in only 76.85% of sequences in the viral library being distinct (i.e., different from one another), as opposed to 94.24% in the plasmid library. In both cases, the outlier sequence was wt AAV3b contamination, but even at more than 7000 times the frequency of most other sequences in the viral library, it only represented 0.69% of the total sequences. The distribution of mutation abundance per sequence was very similar between the plasmid and the viral libraries (FIG. 16B) with only a slight decrease (21.56 vs 23.26 mutations per sequence on average respectively in the viral and plasmid libraries). Sequence comparison between plasmid and viral libraries shows very little overlap (FIG. 16C), suggesting that the actual complexity was much higher than the size of the sequenced sample. Taken together, the NGS data reasonably supports a viral complexity in the order of $1\times10^7$.

Next-Generation (NGS) Sequencing:

Number of sequences processed: 1817050

Number of distinct sequences (complexity): 1708473 (0.94)

| Copy number distribution: | |
| --- | --- |
| Copy number | Number of sequences |
| 1 | 1603700 |
| 2 | 101430 |
| 3 | 3257 |
| 4 | 83 |
| 5 | 2 |
| 377 | 1 |

TABLE 4

Examples of the most representative variants within VRs IV, V, VI, and VII from the master viral library ABC as deduced from the NGS sequencing (the dots in each of Examples 1-86 below represent amino acid residues that are identical to those listed in wild type as shown below). The sequences for Wildtype and Example 1 in Table 4 correspond to SEQ ID NOs: 30 and 31. The sequences for Examples 2-86 in Table 4 correspond to SEQ ID NOs: 32-116, respectively.

| | 450 | 491 | 528 | 546 | cn | % |
| --- | --- | --- | --- | --- | --- | --- |
| Wild type | GTTSGTTNQSRLL | KTANDNNNSNFPWTAASK | KDDEEK | EGTTASNAELDN | | |
| 1 | ............. | .................. | ....... | ............ | 377 | 0.0 |
| 2 | .N.G...SP...R | .IYDR...........T | G..TGR | Q..GEG.V.VGK | 5 | 0.0 |
| 3 | S......G.RK.A | .AYGH....D...P...T | G...DR | ODSGENDVAIGR | 5 | 0.0 |
| 4 | ..A....AN.N.K | ..YS.............. | G..DDR | ...DGA.V.I.R | 4 | 0.0 |
| 5 | ..P...AAHKT.E | ..SAE............. | G..AGR | .DAEGGD.AIGG | 4 | 0.0 |
| 6 | S.AG..AT.KA.T | .VHAH............. | E..TGR | QDA.R..VAFEE | 4 | 0.0 |
| 7 | .NP....GLRG.T | T.D.E........P.... | ...AG. | Q..DGN.IAFGE | 4 | 0.0 |
| 8 | .N.....SKRP.M | T...E...........T | E..N.R | .DAKGTDT.F.R | 4 | 0.0 |
| 9 | SNA....GIHQ.K | TAPDR....E........ | E..NGR | QNGATADT.VER | 4 | 0.0 |
| 10 | SN.G...AMRE.E | .AP......K.......T | E..TG. | .S.AETDV.DGR | 4 | 0.0 |
| 11 | SNA...AGLQ..K | .IPDQ............. | ...NG. | QSGG.ADIDNG. | 4 | 0.0 |
| 12 | .NP....APH... | TIH.G........P...T | ...DGR | QDGGT..IDI.G | 4 | 0.0 |
| 13 | ..P....DLRE.A | .IP..............T | E...DR | ............ | 4 | 0.0 |
| 14 | SNP...A.PRT.M | .IDAH....E...P...T | E..NG. | QSS.TGDV.D.D | 4 | 0.0 |
| 15 | .NA....DTK..T | .ASGG...........T | ...DD. | ..SNRDD..V.R | 4 | 0.0 |
| 16 | .N.G...DIR..R | ..HSE....E.......T | ...N.R | QD.RETDVAI.R | 4 | 0.0 |
| 17 | .NA...AGMRE.M | .A..H............. | E...D. | .SGS.DDVAIGR | 4 | 0.0 |
| 18 | SN.G..ATPKQ.Q | .ASAH....E........ | .....R | ..S.RNDIANEH | 4 | 0.0 |
| 19 | SN.G..A.IKE.T | ..S..............T | R..ND. | QSASKNDI.YEQ | 4 | 0.0 |
| 20 | SNAG...SNRE.R | T.SSQ...........T | R..DDR | QDAGGNDV.VGD | 4 | 0.0 |

TABLE 4-continued

Examples of the most representative variants within VRs IV, V, VI, and VII from the master viral library ABC as deduced from the NGS sequencing (the dots in each of Examples 1-86 below represent amino acid residues that are identical to those listed in wild type as shown below). The sequences for Wildtype and Example 1 in Table 4 correspond to SEQ ID NOs: 30 and 31. The sequences for Examples 2-86 in Table 4 correspond to SEQ ID NOs: 32-116, respectively.

| | 450 | 491 | 528 | 546 | cn | % |
|---|---|---|---|---|---|---|
| 21 | SN....ATT.A.K | ..YGH............ | G..T.. | Q.GS.N.V.VES | 4 | 0.0 |
| 22 | SNAG..AATN... | .IYDR...........T | R...D. | ..GEKG.VDI.R | 4 | 0.0 |
| 23 | S.P....ATKG.T | TAHTG............ | G..DG. | ..S..TDVAIGS | 4 | 0.0 |
| 24 | .N.G...DLR..M | T.D.H....E...P...T | G..KGR | .NGAKNDIAFEG | 4 | 0.0 |
| 25 | S......TLKA.Q | .IP.R...........T | G...DR | .NSKGA.T.I.E | 4 | 0.0 |
| 26 | .......DPKD.V | T.HG.....D.......T | ...DD. | .D.A.D.V.FGR | 4 | 0.0 |
| 27 | S.AG...TIKD.V | .VPD.....K........ | E..D.R | QDSG.T.V.FGR | 4 | 0.0 |
| 28 | ...G...TMRK.G | .VYGG...........T | E..A.R | QSSGRNDV.YGD | 4 | 0.0 |
| 29 | .N.G..ASTR..T | .IPDQ........P.... | E...GR | QSAEKGDI.YGR | 4 | 0.0 |
| 30 | .N.....ATHT.A | .IHSR....D...P.... | E..AG. | Q.A..G.IDVEQ | 4 | 0.0 |
| 31 | SNPG...SIRG.Q | TIP.R........P...T | R..TD. | Q.GG.G.TDF.H | 4 | 0.0 |
| 32 | S.....AAPRG.V | TVYGH....E........ | ....GR | ..AG...VAIEE | 4 | 0.0 |
| 33 | .NA...ATKQG.M | .VP.Q....D........ | ...DDR | QSSDKN...D.S | 4 | 0.0 |
| 34 | SNAG..ATT.Q.R | TAPAE........P...T | R..ADR | .SGRGD.VDFEK | 4 | 0.0 |
| 35 | SN.G..AGIRA.Q | .VDTG....D.......T | E..T.. | .NSARND.DIGR | 4 | 0.0 |
| 36 | .NA...AA.NG.R | .IP.E....K.......T | ....G. | .SSSGDD..FGG | 4 | 0.0 |
| 37 | SN....AGPQQ.R | ..HAQ............ | E..TG. | ..AR.NDIAF.Q | 4 | 0.0 |
| 38 | S.P....SMRT.E | .APAR....E.......T | R..AG. | Q.SRENDT.F.G | 4 | 0.0 |
| 39 | S.AG...ALKG.K | TI.DH....E...P...T | R..K.. | .DS.GA.IAD.R | 4 | 0.0 |
| 40 | S.P...ASTRT.M | ..H.H....E.......T | ....D. | ...E.T.VAIGG | 4 | 0.0 |
| 41 | .NPG....NQA.R | .IHGQ....D.......T | R..ND. | ..SARGDVAYEK | 4 | 0.0 |
| 42 | SNA....DTRE.V | TI.D.....E.......T | R..TD. | Q.SAGADV.VEK | 4 | 0.0 |
| 43 | SNPG....LRE.R | TIHTE....E.......T | R..KDR | Q.GGGT.V.IGS | 4 | 0.0 |
| 44 | ...G..A.NNT.. | .I.SG............T | ...KGR | ..AEKNDTAVG. | 4 | 0.0 |
| 45 | .......DKQQ.M | ..H.G....D........ | E..TG. | QSAEGN.VAY.G | 4 | 0.0 |
| 46 | ..AG..ATL.T.V | .ISAG....D........ | G..NG. | QNS...DVAI.G | 4 | 0.0 |
| 47 | SN....AGLRT.T | .ADA.....D...P...T | G..NG. | .DASGN.V.DGR | 4 | 0.0 |
| 48 | SNA...ATP.T.R | ..DTH....E...P.... | R..NDR | ..ARG..IDVGD | 4 | 0.0 |
| 49 | S.A...ASLRA.M | .VP.R...........T | G..ND. | .NAR..D..V.R | 4 | 0.0 |
| 50 | ..A...ATTKG.. | .ISTQ............ | E..AD. | Q.GETD.VDVGD | 4 | 0.0 |
| 51 | ..A...AALKQ.A | .ADS.............T | E..ADR | Q.GETG.I.Y.G | 4 | 0.0 |
| 52 | .NA...ATT.N.M | .ADDR...........T | ....DR | Q.AKR.DTAVEE | 4 | 0.0 |
| 53 | ..AG..A.MKD.R | T..SE....D.......T | E..KD. | ..ANGGDVAIGQ | 4 | 0.0 |
| 54 | S.PG...TIRD.K | TVST.....D...P...T | ...DDR | ..SGRN.VAVEE | 4 | 0.0 |
| 55 | S.P...A.INT.R | ..P.R...........T | E...GR | QSA.KDDVDIGG | 4 | 0.0 |
| 56 | .N.G..AGLQK.M | ..HGG........P...T | ...DG. | QSSRGNDVAV.D | 4 | 0.0 |

TABLE 4-continued

Examples of the most representative variants within VRs IV, V, VI, and VII from
the master viral library ABC as deduced from the NGS sequencing (the dots in each
of Examples 1-86 below represent amino acid residues that are identical to those
listed in wild type as shown below). The sequences for Wildtype and Example 1 in
Table 4 correspond to SEQ ID NOs: 30 and 31. The sequences for Examples 2-86 in
Table 4 correspond to SEQ ID NOs: 32-116, respectively.

| | 450 | 491 | 528 | 546 | cn | % |
|---|---|---|---|---|---|---|
| 57 | .N.....TPRT.A | .IPSH....E........ | ...... | Q.SNG..I.FGS | 4 | 0.0 |
| 58 | SNAG..AGLRQ.T | .APAE....D.......T | E..AG. | ..GGGA.IAVEE | 4 | 0.0 |
| 59 | ..A...AAK.T.V | .ISTR...........T | E..... | ...SKNDV.VE. | 4 | 0.0 |
| 60 | .......TTR..M | .IYGG...........T | E..AGR | Q..ATA.V.VES | 4 | 0.0 |
| 61 | ..AG..AGMRE.A | TIYTG............ | ....GR | ..SSTGD.DVGR | 4 | 0.0 |
| 62 | S..G..A.PKE.R | TA..H....E.......T | E...D. | Q.AGE..VAI.G | 4 | 0.0 |
| 63 | .......GT.T.R | ..DTG............ | G....R | ..AGTAD.AV.G | 4 | 0.0 |
| 64 | .NAG....KRD.. | TAYTR....D.......T | ...D.. | Q..GKTD.DNGG | 4 | 0.0 |
| 65 | .NA....DMKH.T | .ISDR........P...T | R..N.R | QS.RGG...I.G | 4 | 0.0 |
| 66 | SN.G..ADLRD.. | TIPTQ....E........ | ...NDR | QSAK.NDV.V.R | 4 | 0.0 |
| 67 | S.A....ATQQ.V | T.DSQ....E.......T | R..NDR | .NAEGG.V.IGQ | 4 | 0.0 |
| 68 | .NAG...ANKT.M | .I.AH....E.......T | R..DG. | QDSS.D.I.YGK | 4 | 0.0 |
| 69 | .NAG...GTKE.R | TI..E...........T | ...D.. | .DAKRN.VDY.G | 4 | 0.0 |
| 70 | SNP....GK.S.K | ..S.E............ | ...NG. | .DSR.GD.DFEK | 4 | 0.0 |
| 71 | .N....ASIRQ.Q | ..PDG....K........ | R..NGR | ..S.EG.I.IEG | 4 | 0.0 |
| 72 | .N.G...TL.A.G | TAHTQ............ | R..ND. | QSS.GGDTAF.G | 4 | 0.0 |
| 73 | SNP....TTQ..Q | ..D......D...P...T | R..TDR | ..S.GGD..IER | 4 | 0.0 |
| 74 | SNA....TMRK.G | TISSG........P.... | G..N.. | QDSSENDVADER | 4 | 0.0 |
| 75 | S.AG..ATMQ..M | T.DTG...........T | R..N.R | Q.GEGGDI.D.R | 4 | 0.0 |
| 76 | ..AG..ATTRD.Q | T.DDH....D........ | ...NGR | Q.GRGA.TAYEG | 4 | 0.0 |
| 77 | ...G..AAM.A.R | T.DDG....K...P.... | ...... | .DGGT...AIGD | 4 | 0.0 |
| 78 | .N.....TNRE.M | .IP.............T | R...D. | .D.GRADV.VGR | 4 | 0.0 |
| 79 | SNAG..ADKQD.V | TAHSE............ | E..DDR | Q.AAGGDI.VGS | 4 | 0.0 |
| 80 | .NA...AATHE.. | T.HDH....D........ | R..A.R | ..GAK.DVDFGS | 4 | 0.0 |
| 81 | SNA...ADTRH.M | T.PGE....D...P...T | G..TG. | Q.SATTDI.YGE | 4 | 0.0 |
| 82 | SN.....A..K.Q | .IH.R....D.......T | R..DDR | Q.AEG.DVAVGD | 4 | 0.0 |
| 83 | .NP...AD.RA.Q | .IPTG....D.......T | R..T.. | Q..GG.DI.IGG | 4 | 0.0 |
| 84 | SNA...AGLNA.K | .AYTH....D.......T | G..D.R | .NAK.G..AI.G | 4 | 0.0 |
| 85 | .NP.....LQ..M | .IDDQ........P...T | ....D. | .SGGTADVAV.K | 4 | 0.0 |
| 86 | ......ASIQ..Q | ..YA.....E.......T | ....D. | .SAAG.DT.V.G | 4 | 0.0 |

Calculated plasmid library complexity based on colony count ($2.5 \times 10^7$) and NGS sequencing (0.94 of unique sequences) is $2.35 \times 10^7$. The degree of wt AAV3B contamination is 0.02%.

| Q5 PCR: | |
|---|---|
| 50 µl: | 10 µl 5xB Q5 |
| | 0.4 µl 25 mM dNTPs |
| | 2.5 µl F |
| | 2.5 µl R |
| | 1 µl (1 ng) pITR3-R3C3-AatII |
| | 0.5 µl Q5 Pol |
| | H₂O up to 50 µl |
| 98° C. 30 sec | |
| 98° C. 10 sec | |

-continued

| Q5 PCR: | |
|---|---|
| 65° C. 20 sec | 30 cycles |
| 72° C. 30 sec | |
| 72° C. 2 min | |

Figure 6:
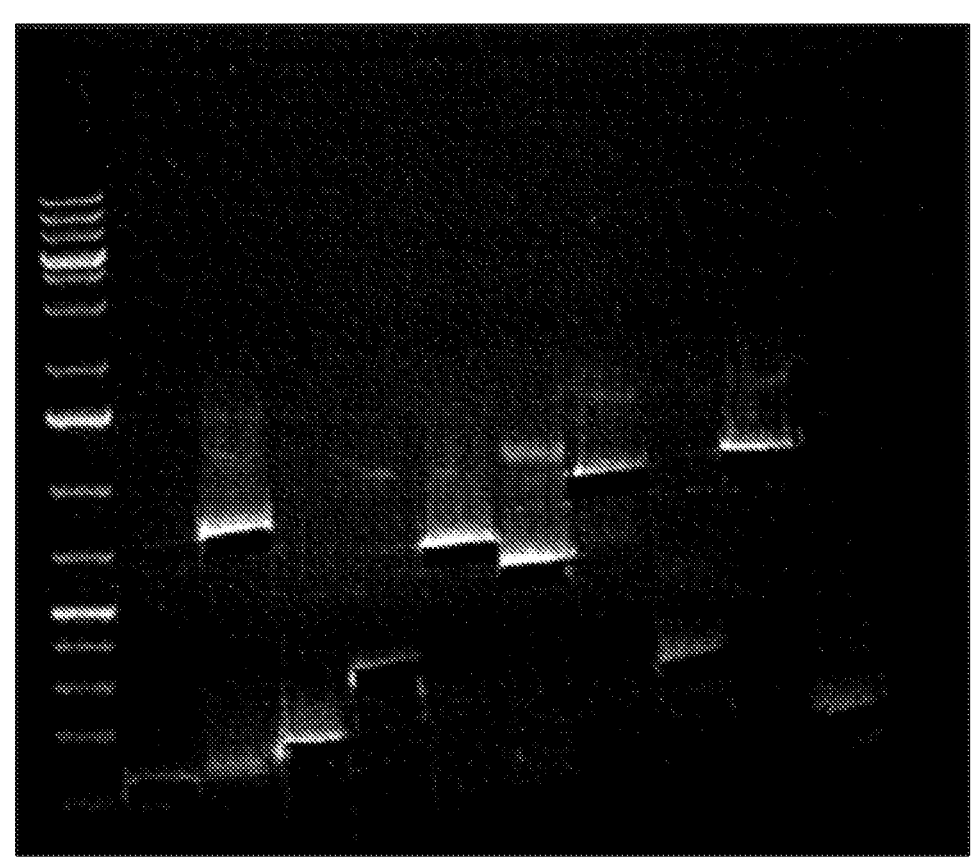
FIGS. 6-9 are photographs of agarose gels showing products of PCR reactions as per Example 2.

See FIG. 6.

TABLE 5

| | Fragment | Size (bp) | Conc. (µg/ml) | nM | µl/5 × 10⁹ copies |
|---|---|---|---|---|---|
| A | 1 | 86 | 10.4 | 186 | 2.2 |
| I + V + VI | 2 | 747 | 33.3 | 69 | 6 |
| | 3 | 136 | 13.2 | 149 | 2.8 |
| | 4 | 281 | 35.4 | 194 | 2.1 |
| B | 5 | 647 | 48 | 114 | 3.6 |
| IV | 6 | 556 | 29.4 | 81 | 5.1 |
| C | 7 | 935 | 22.5 | 37 | 11.2 |
| VII | 8 | 266 | 11.2 | 65 | 6.4 |
| D | 9 | 1055 | 38.8 | 57 | 7.3 |
| VIII | 10 | 147 | 35.9 | 376 | 1.1 |

TABLE 6

| OE Q5 PCR | | | | | | | | | | |
|---|---|---|---|---|---|---|---|---|---|---|
| | | | | | 0 | xB | NTP | 3CL-F | 3CL-R | 5 | ₂O |
| .2 | .8 | .1 | | | 0 | .4 | .5 | .5 | .5 | 6 |
| | .6 | .1 | | | 0 | .4 | .5 | .5 | .5 | 0.4 |
| | | 1.2 | 4 | | 0 | .4 | .5 | .5 | .5 | 1.5 |
| | | | .3 | .1 | 0 | .4 | .5 | .5 | .5 | 0.7 |

1. Assays A, B, C, and D are assembled without primers, substituting H₂O for the primers' volumes (5 µl) and subjected to the following overlap extension:

| 98° C. 30 sec | |
|---|---|
| 98° C. 10 sec | |
| 65° C. 20 sec | 15 cycles |
| 72° C. 60 sec | |
| 72° C. 2 min | |

2. 40 µl each A, B, C, and D from Step 1 transferred to 10 µl containing:

| | X5 |
|---|---|
| 2.5 µl A3CL-F | 12.5 |
| 2.5 µl A3CL-R | 12.5 |
| 2 µl 5xB Q5 | 10 |
| 0.08 µl dNTPs | 0.4 |
| 0.1 µl Q5 | 0.5 |
| 2.82 µl H₂O | 14.1 |

Assays are subjected to the following PCRs:

| 98° C. 30 sec | |
|---|---|
| 98° C. 10 sec | |
| 59° C. 20 sec | 20 cycles |
| 72° C. 60 sec | |
| 72° C. 2 min | |

Figure 7:
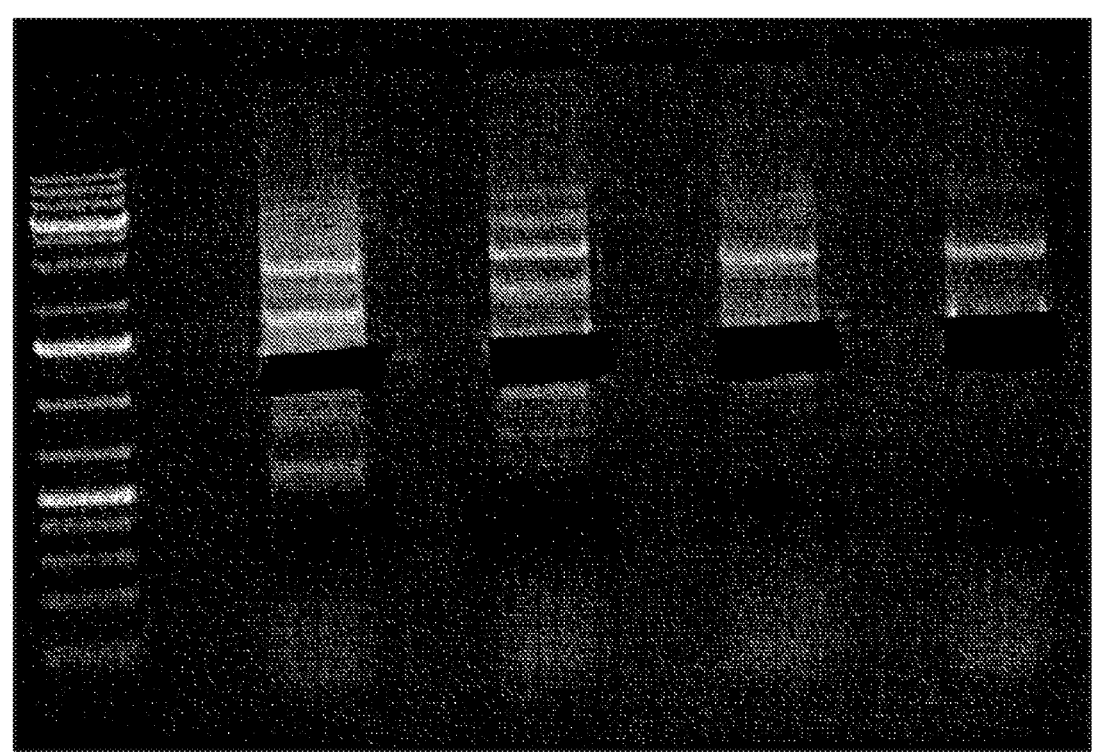

See FIG. 7: Eluted in 50 µl each A, B, C, or D; pTR3-R3C3-AatIVAatII+ApaI eluted in 75 µl.

TABLE 7

| | Size (bp) | Conc. (ng/µl) | Molarity (nM) | Conc. (pmoles/µl) | µl/40 µl assay | pmoles/ 40 µl assay (3:1) |
|---|---|---|---|---|---|---|
| A | 1091 | 47.5 | 67 | 0.067 | 2.1 (100 ng) | 0.144 |
| B | 1091 | 58.3 | 82 | 0.082 | 1.8 (100 ng) | 0.144 |
| C | 1091 | 49.9 | 70 | 0.07 | 2.1 (100 ng) | 0.144 |
| D | 1091 | 60.9 | 86 | 0.086 | 1.7 (100 ng) | 0.144 |
| pITR3-R3C3- AatII AatII-ApaI cut | 6594 | 54.3 | 13 | 0.013 | 3.7 (200 ng) | 0.048 |

| IDA | A | B | C | D | pITR3 | H₂O | |
|---|---|---|---|---|---|---|---|
| 40 µl assay: | 2.1 | | | | 3.7 | 14.2 | A |
| 20 µl 2×Gibson | | 1.8 | | | 3.7 | 14.5 | B |
| Master Mix | | | 2.1 | | 3.7 | 14.2 | C |
| (NEB) + | | | | 1.7 | 3.7 | 14.6 | D |

Large-Scale IDA for the Loop A

300 µl assay:

150 µl 2×Gibson Master Mix 27.6 µl pITR3-R3C3-AatII AatII-ApaI cut (1.5 µg)

15.8 µl A (0.75 µg)

106.6 µl H₂O

Incubated 2 h, 50° C., Zymo-purified, eluted in 100 µl H₂O, combined with 47.5 µl of A from the pilot IDA above. Total—1.7 µg of vector plasmid DNA.

Lucigen competent cells were prepared from 4 L LB, resuspended in 8.5 ml H₂O final volume. The cell density (10 µl in 3 ml H₂O) was $A_{550}$=0.79.

Combined DNA (147.5 µl) was mixed with the whole volume of competent cells and aliquoted (385 µl/aliquot, ~10 ng plasmid DNA/50 µl competent cells) into electroporation cuvettes (total of ~20, with outside tall electrodes) and zapped at 2.9 KV.

Cells were transferred into 1 L LB, incubated shaking at 37° C. for 1 h. Carbenicillin was added up 100 µg/ml, cell were grown at 30° C., o/n.

Total complexity from the large-scale IDA/transformation is $4.4 \times 10^7$ clones.

Repeat IDA for the Loop C

100 µl assay:

50 µl 2×Gibson Master Mix 9.25 µl pITR3-R3C3-AatII AatII-ApaI cut (0.5 µg)

5.25 µl C (0.25 µg)

35.5 µl H₂O

Zymo, 50 µl H₂O.

Competent cells were prepared from 4 L LB (grown to $A_{550}$=0.6) and resuspended in a final volume 8 ml H₂O. The cell density (10 µl in 3 ml H₂O) was $A_{550}$=1.46.

180 ng vector with fragment B from the pilot IDA were electroporated with 1 ml of comp. cells, whereas 0.68 µg with fragment C—with 3 ml of cells.

After electroporation the complexity of B was $\sim 1.7 \times 10^7$ (~5 times over theoretical complexity), while C $\sim 1 \times 10^8$ (~2.5 times over theoretical complexity).

TABLE 8

| | Pilot | | | | Large-scale | | | |
|---|---|---|---|---|---|---|---|---|
| | A | B | C | D | A | B | C | D |
| Complexity total | $0.9 \times 10^5$ | $0.7 \times 10^5$ | $1.4 \times 10^5$ | $0.9 \times 10^5$ | $4.4 \times 10^7$ | $1.7 \times 10^7$ | $1 \times 10^8$ | $1 \times 10^8$ |
| Volume (µl) | 400 | 400 | 400 | 400 | 1000 | 100 | 500 | 1000 |
| Complexity/µl | 225 | 175 | 525 | 225 | $4.4 \times 10^4$ | $1.7 \times 10^5$ | $2 \times 10^5$ | $10^5$ |
| DNA concentration (ng/µl) | 342 | 220 | 241 | 334 | 1690 | 1100 | 2100 | 2000 |
| Copies/µl | $4.2 \times 10^{10}$ | $2.6 \times 10^{10}$ | $2.9 \times 10^{10}$ | $4 \times 10^{10}$ | $2 \times 10^{11}$ | $1.3 \times 10^{11}$ | $2.5 \times 10^{11}$ | $2.4 \times 10^{11}$ |
| Representation (copies/variant/ µl) | $1.9 \times 10^8$ | $1.5 \times 10^8$ | $0.6 \times 10^8$ | $1.8 \times 10^8$ | $4.5 \times 10^6$ | $7.6 \times 10^5$ | $1.3 \times 10^6$ | $2.4 \times 10^6$ |
| Dilution factor | 42.2 | 197.4 | 46.2 | 75 | | | | |
| Final DNA concentration after mixing equal volumes (µg/µl) | | | | | | 0.55 | 1.1 | 1 |
| Viral DNA concentration, 80 µl (µg/ml) | | | | | 27.6 | 22.8 | 23.2 | 85.5 |
| Titer (copies/µl) | | | | | | $4.5 \times 10^9$ | $4.6 \times 10^9$ | $1.6 \times 10^{10}$ |

Q5 PCR of Viral DNA

Conditions, as above, except: 50 ng viral DNA/50 μl assay, 20 PCR cycles 5 μl out of 50

1. Loop I, primers A3CL-F+VR-I_IV-R, template A, size 644 bp
2. Loop IV, primers VR-I_IV-F+VR-IV_V-R, template B, size 145 bp
3. Loops V+VI, primers VR-IV_V-F+VR-VI_VII-R, templ. A, size 194 bp
4. Loop VII, primers VR-VI_VR-VII-F+A3CL-R, template C, size 274 bp Remaining 45 μl were purified using preparative gel, all four gel cutouts were pooled in one tube and purified using one column, final volume 50 μl H$_2$O.

Figure 8:
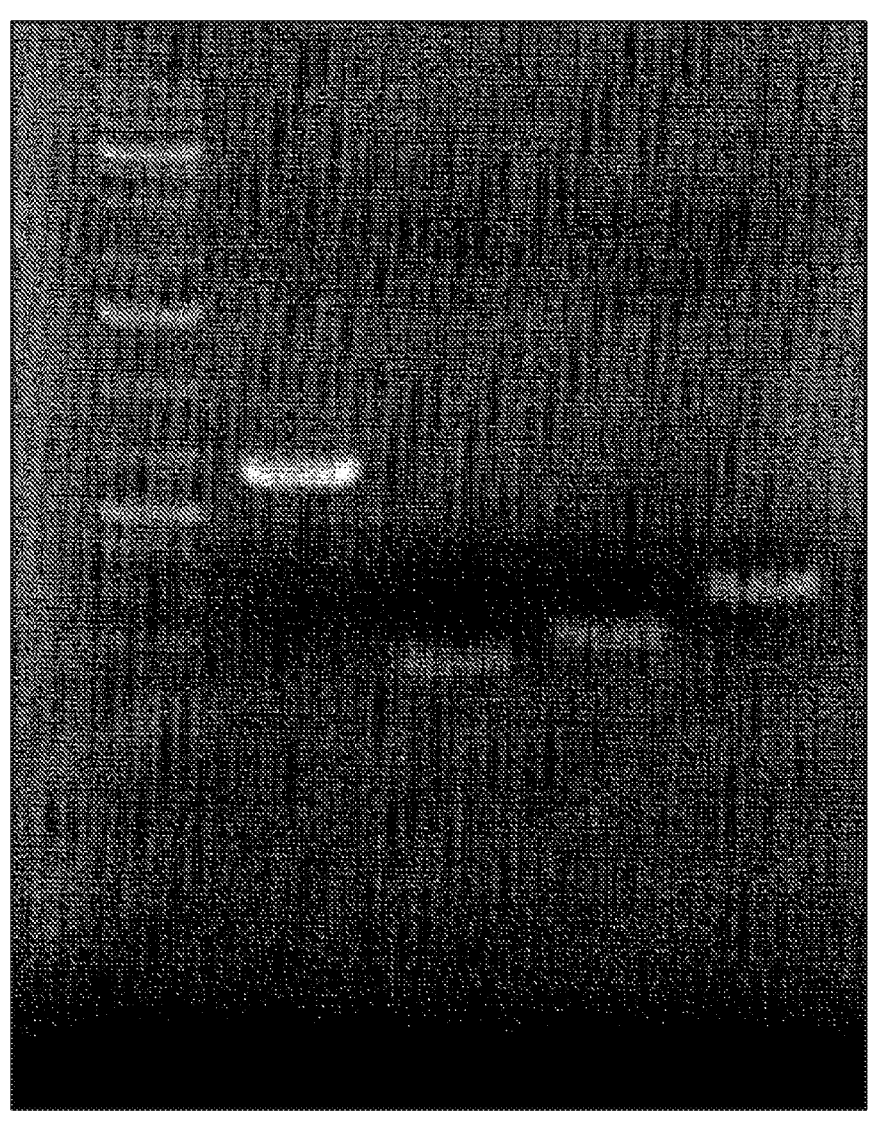

See FIG. 8.

Overlap Extension

Full-length fragment was assembled without primers, substituting H$_2$O for the primers' volumes (5 μl) and subjected to the following overlap extension:

| 50 μl: | 10 μl 5xB Q5 |
| | 0.4 μl 25 mM dNTPs |
| | 25 μl (out of 50 μl) individual |
| | overlap 4 fragments mix (p. 12) |
| | 0.5 μl Q5 Pol |
| | 14.1 μl H$_2$O |
| 98° C. 30 sec | |
| 98° C. 10 sec | |
| 65° C. 20 sec | 15 cycles |
| 72° C. 60 sec | |
| 72° C. 2 min | |

After primer-less extension, the assay was split into 2×25 μl assays supplemented with A3CL-F, and A3CL-R primers, DNTPs, and fresh Q5, total volume 50 μl each.

Assays are subjected to the following PCRs:

| 98° C. 30 sec | |
| 98° C. 10 sec | |
| 59° C. 20 sec | 20 cycles |
| 72° C. 60 sec | |
| 72° C. 2 min | |

ABC fragment was eluted in 50 μl, concentration 60 ng/μl (0.085 pmoles/μl).

D fragment was eluted in 50 μl, concentration 46 ng/μl (0.065 pmoles/μl).

Figure 9:
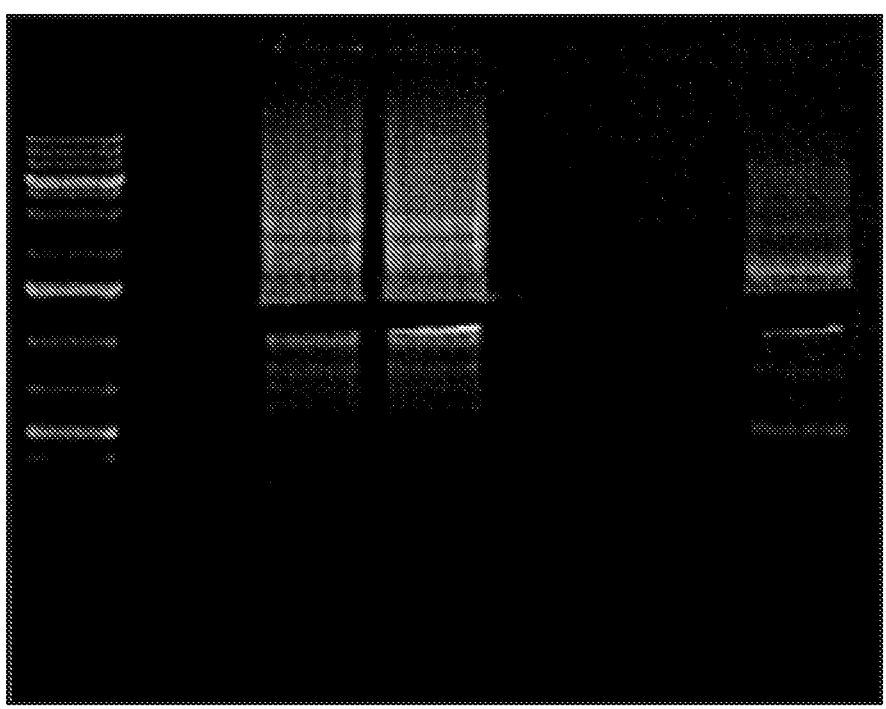

See FIG. 9.

IDA using NE Builder Master Mix

Total volume—200 μl, plasmid 1.5 μg (0.348 pmoles), insert—0.5 μg (0.7 pmoles), total DNA amount ~1 pmole/ 200 μl assay.

Reaction 60 min@50° C. Lucigen electrocompetent *E. coli* cells, 8 ml, final density 0.8 A550. Library's complexity 2.5×10$^7$.

Example 2

In Vitro Selection for Liver Targeted AAV Variants

The AAV3B library was selected for variants with enhanced adaptive survival and proliferation in a human hepatocellular carcinoma cell line (HUH-7). First, in order to mimic in vitro the 3-dimensional organoid structure of the liver, spheroid cultures were generated by culturing HUH-7 cells in ultra-low attachment plates (6 well) in DMEM/F12K media supplemented with epidermal growth factor (EGF, 20 ng/ml), fibroblast growth factor (10 ng/ml), B27 (1×). Spheroids formed from single cells within 5-7 days. All infections were performed at 7 days of spheroid formation.

3D HUH-7 spheroid cultures were generated in order to more closely mimic hepatocyte conditions in vivo[30]. Discrete spheroids (~100-500 μm) were observed within 5-7 days, and spheres were used on day 7 for serial selection of the AAV3B combinatorial capsid library. On day 7, spheres were centrifuged at 300 g for 5 min and re-suspended in 1ml of non-supplemented DMEM/F12K medium. Spheres were first incubated with Ad5 helper virus at a multiplicity of infection (MOI) that had previously generated 50% cytopathic effect (CPE). Incubation was carried out for 1 hr at 37° C. in a humidified CO$_2$ incubator. Spheres were then centrifuged in 30 ml of medium in order to remove unbound virus. Following this, spheres were then re-suspended in 1ml of medium and incubated with 1 MOI of the AAV3 library for 1 hr at 37° C. in the incubator. Following two to three centrifugations in 30 ml of medium in order to remove unbound virus, spheres were incubated for 72 hrs. This constituted the first cell passage of the AAV3B library.

The first selection passage (P-1) was carried out using a multiplicity of infection (MOI) of 1. Subsequent passages were carried out using 0.01 MOI in order to prevent loss of genotype-phenotype correlation. Altogether, 5 rounds of in vitro selection were carried out. Adenovirus 5 (Ad5) superinfection was performed at each round of selection based on similar studies for AAV library selection[23,31,32].

For subsequent cell passages (five in total), virus was released from cells and supernatant from P-1 by continuous freeze and thaw steps (three in total). Clarified supernatant from P-1 was then used to infect another batch of HUH-7 spheres, this time at 0.01 MOI, in order to prevent recombinant genome-capsid combinations from occurring. In accordance with this method, five passages of selection were carried out and AAV3B-DE5 identified as a dominant variant.

Samples collected after each round were sequenced (on the PacBio platform). Evolution of sequence frequencies is displayed in FIG. 17 (for clarity, only sequences present at more than 1% in at least one sample are shown individually). One sequence, shown as V1 in FIG. 17, was overwhelmingly selected and became predominant at round4. This sequence is referred to as AAV3B-DE5 (AAV3B directed evolution 5).

Figure 18D:
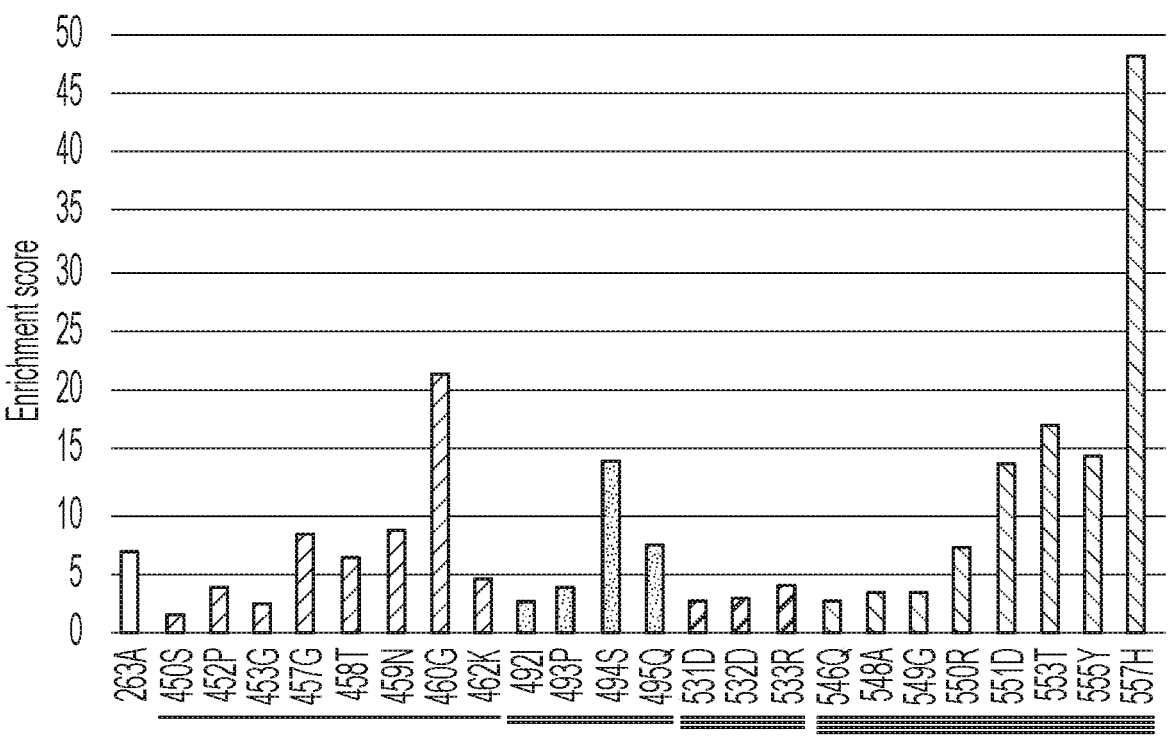

AAV3B-DE5 (more precisely its VR-IV to VR-VII region) was not detected in the original viral library, which means that its frequency was lower than 1 per million. Even the VR-IV region of AAV3B-DE5 itself could not be found in the original viral library, while the VR-V, VR-VI and VR-VII regions were present at frequencies of 0.11%, 3.43% and 0.01% respectively. AAV3B-DE5 contains 24 amino acid substitutions compared with AAV3B (FIG. 18A), distributed among all five variable regions, including 23 in VR-IV to VR-VII (slightly more than the library average of 21.56). All substitutions were part of the original library design. The positions of these mutations on the capsid surface are displayed in FIG. 18B. Enrichment scores, defined as the products of enrichment factors (FIG. 18C) between rounds of selection, were computed for each AAV3B-DE5 mutation (FIG. 18D). The enrichment factor ("%") refers to the percentage of all nucleotide sequence reads (or "copies") that are represented by the genome associated with a particular variant, in the particular screening round. (Reads are determined through next-generation sequencing (NGS) of the genomes.) The higher the value of this percentage, the better the variant is suited to target and infect the cell.

Mutations N557H, R460G, A553T, N494S, S551D and L555Y obtained the highest scores, suggesting they were the main drivers for selection, while mutations with lower scores are more likely passengers.

AAV3B-DE5 was further characterized in vitro and in vivo in the experiments of Example 3. Its sequence is deposited in GenBank under accession number MT396223.

Example 3

Characterization of AAV3B-DE5

In Vitro Characterization: Transduction Efficiency

Figure 12A:
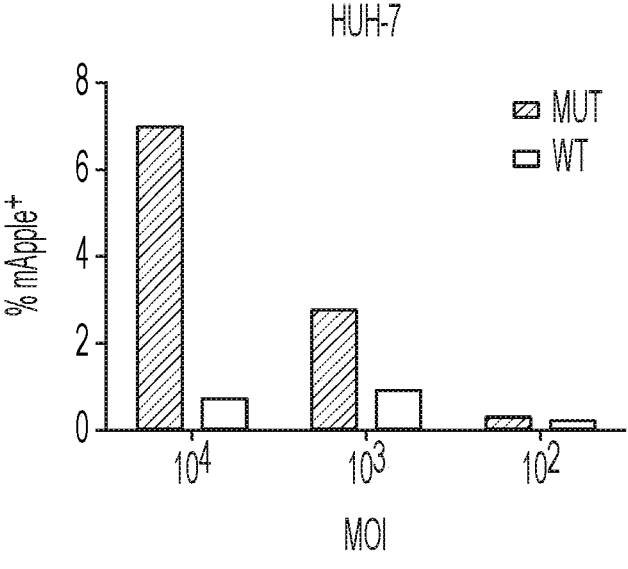
FIGS. 12A-12C are graphs showing results for transduction efficiencies in HUH-7 and HepG2 spheroid cell lines. HUH-7 and HepG2 were transduced with AAV virions comprising an mApple reporter tag and an AAV3B (WT) or DE5 (MUT) capsid, at varying multiplicities of infection (MOI). The percentage of cells transduced (mApple+) was quantified by flow cytometry.
Figure 12B:
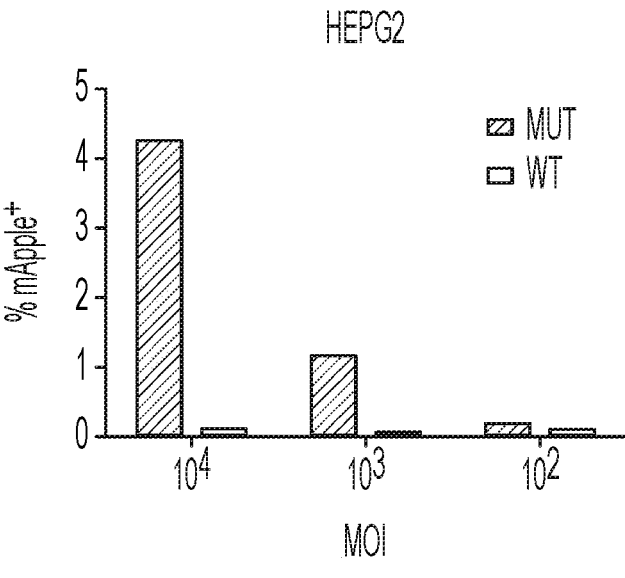
Figure 12C:
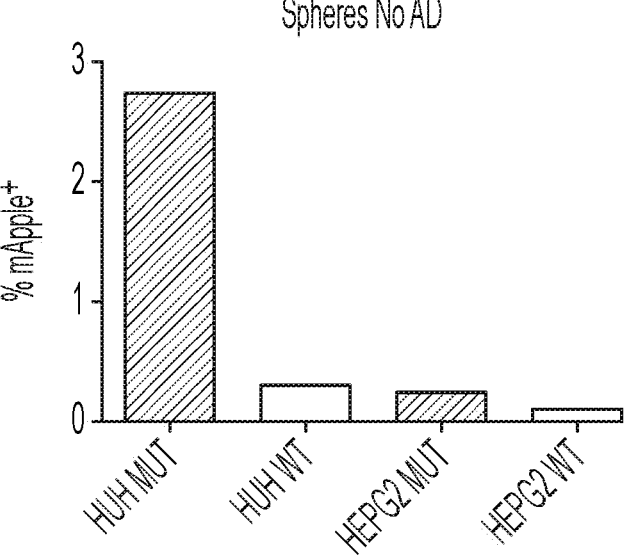
Figure 13A:
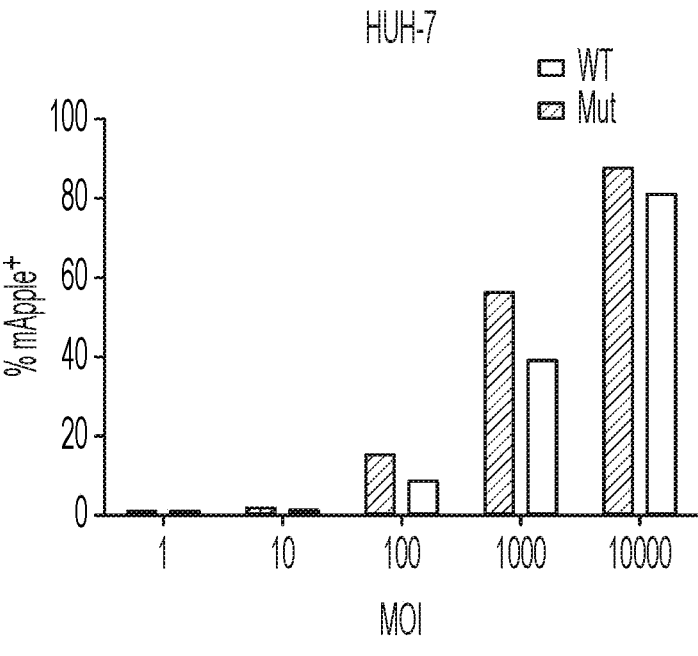
FIGS. 13A-13B are graphs showing results for results for transduction efficiencies in HUH-7 and HepG2 adherent cell lines, at five different MOIs.
Figure 13B:
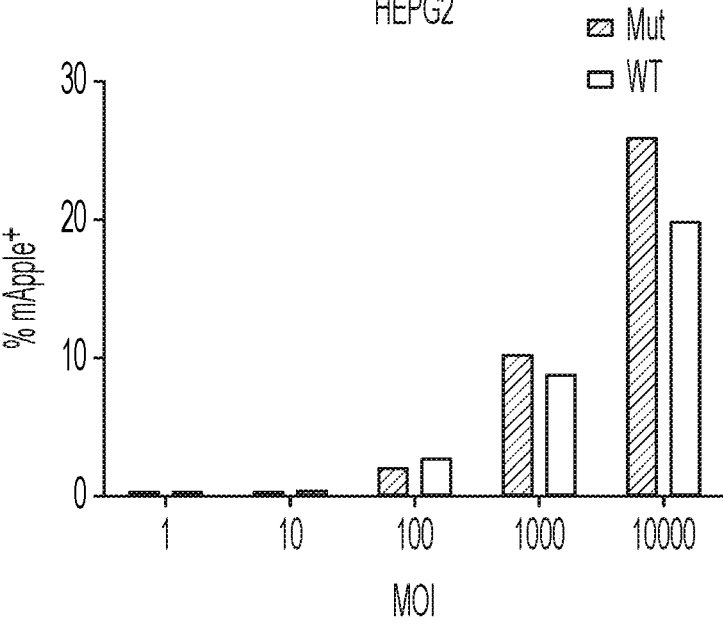

For comparing transduction efficiencies of AAV3B-DE5 with parent (wild-type) AAV3B in human and murine hepatocellular carcinoma cell lines, AAV3B and AAV3B-DE5 virions having an mApple reporter fluorescent tag were generated. These virions were then transduced into three different human and murine hepatocyte cell lines, i.e. HUH-7, HEPG2, and H2.35, with varying MOIs: $10^2$, $10^3$, and $10^4$. Both adherent (two-dimensional) cell lines (FIGS. 13A-13B) as well as cell lines grown as spheroids (FIGS. 12A-12C) were tested. Transduced cells were quantified by flow cytometry.

Figure 14:
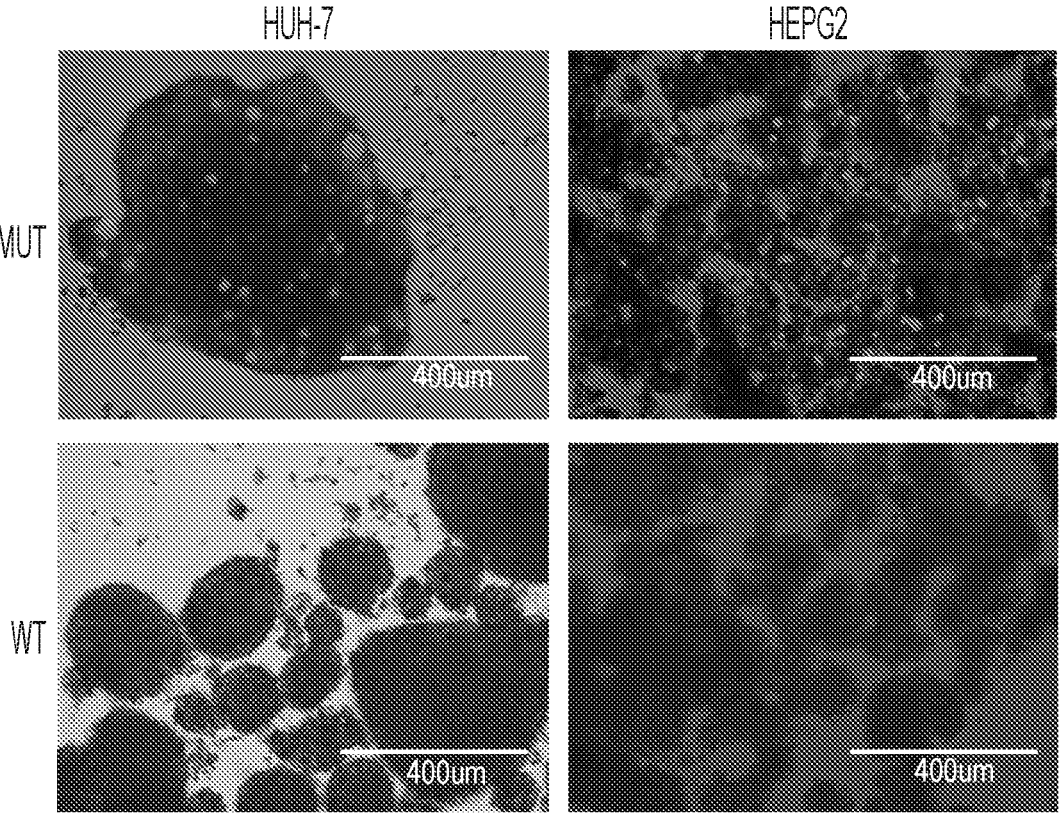
FIG. 14 depicts fluorescence images of HUH-7 and HEPG2 spheroid cultures transduced with wt AAV3B and AAV3B-DE5 ("MUT") vectors, expressing the mApple reporter transgene.

AAV3B-DE5 transduced a greater percentage of cells and showed higher mApple intensity (mFI), indicating increased transduction efficacy as compared to wild-type AAV3B. See FIGS. 12A-12C, 13A, 13B. mApple fluorescence intensity in spheroid cells is illustrated in FIG. 14.

Transduction efficiencies of the DE5 capsid was also assessed in primary hepatocytes pooled hepatocytes from multiple patients (sourced from BioIVT). Primary hepatocytes grown as adherent cells or as spheroids were transduced with Ad5 followed by AAV3B or AAV3B-DE5 viruses. The wild-type and mutant (DE5) virions transduced primary hepatocytes equally.

Figure 19A:
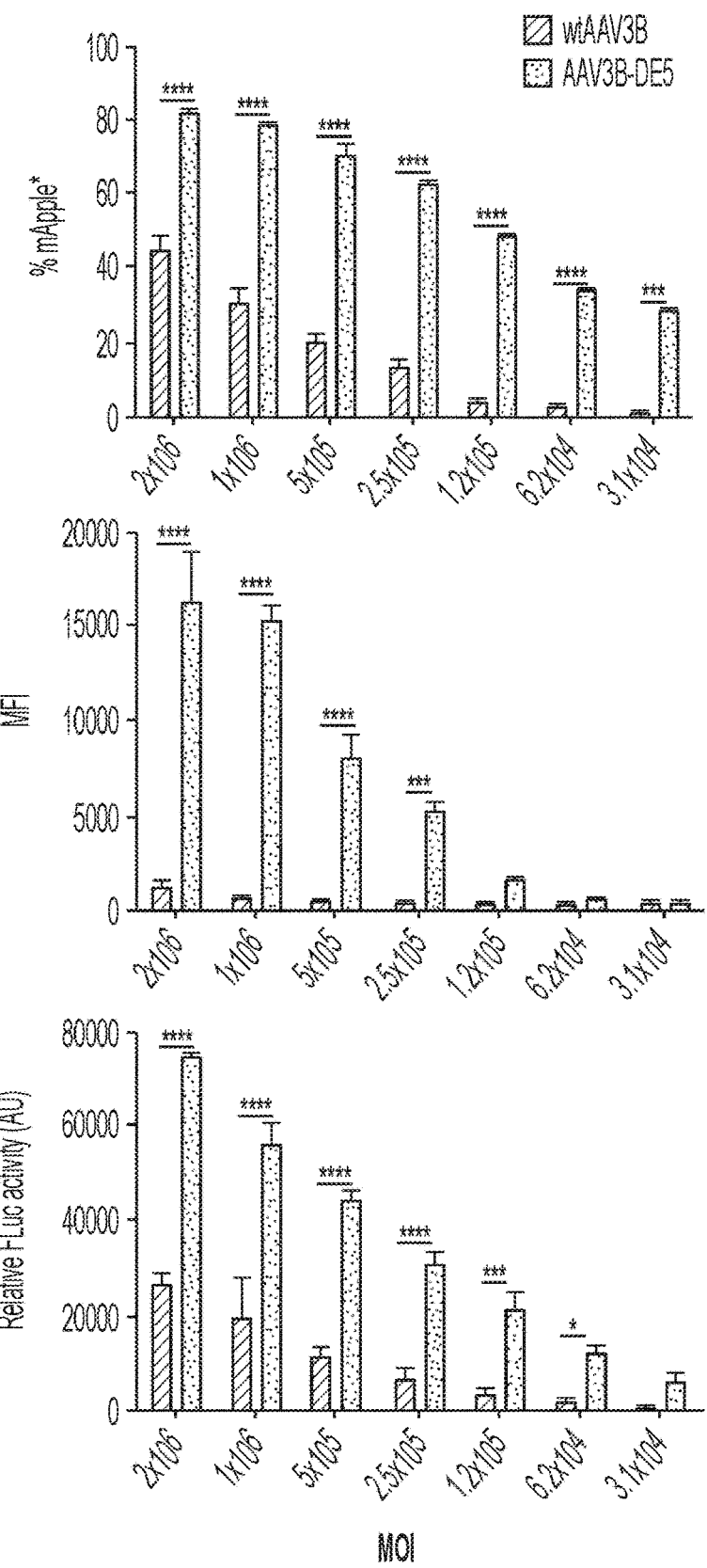
FIGS. 19A-19C show comparative transduction of human hepatocellular carcinoma cell lines in vitro.
Figure 19B:
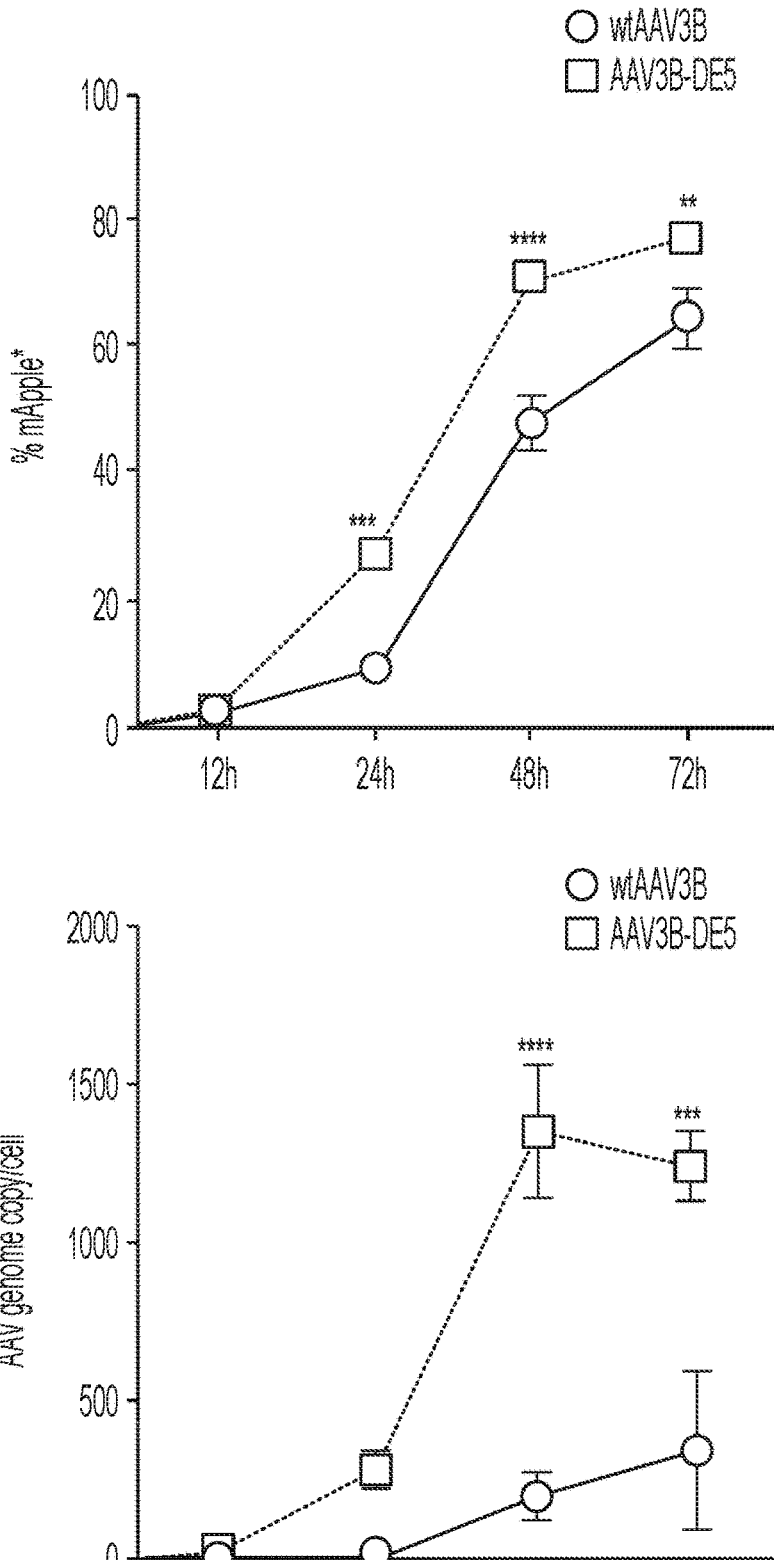
Figure 19C:
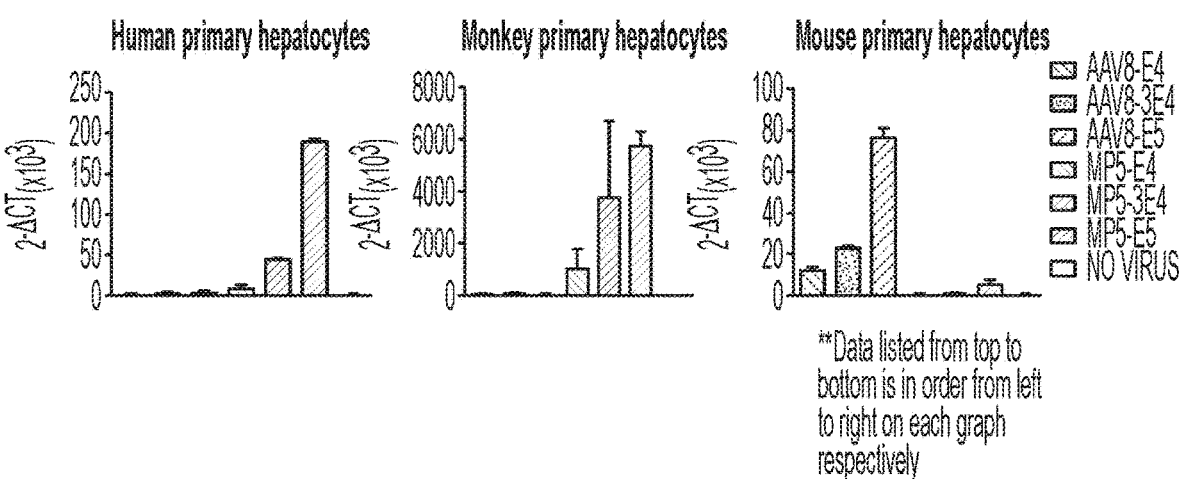

To confirm these transduction efficiencies, wt AAV3B and AAV3B-DE5 capsids were packaged with the pTR-UF50-BC transgene plasmid to express the firefly luciferase (FLuc) and mApple reporter transgenes (separated by a furin recognition site and self-cleaving 2-A peptide) under control of the CBA promoter, flanked by AAV2 ITRs. Transduction efficiencies in spheroid cultures derived from 2 human hepatocellular carcinoma cell lines HUH-7 and HEPG2 were compared. Increased transduction efficiencies at $1\times10^4$ MOI of the AAV3B-DE5 vector was observed in both cell types as visualized by fluorescence imaging for mApple (FIG. 14). AAV3B-DE5 transduced HUH-7 adherent monolayers at higher frequencies as compared to wt AAV3B at different MOIs. This was confirmed by % mApple+cells, mApple MFI, and relative luciferase (FLuc) activity (FIG. 19A). Kinetics of transduction frequencies (% mApple+) as well as AAV genome copies/transduced cell using an MOI of $5\times10^5$ further indicated increased transduction efficiency as well as genome copies per cell for the AAV3B-DE5 variant (FIG. 19B). Further, AAV3B-DE5 with AAV8 transduction (both expressing GFP transgene) in primary human, non-human primate, and murine hepatocytes. AAV8 has high tropism for murine livers but transduces human hepatocytes rather poorly[23, 33]. Increased in vitro transduction was confirmed by estimating transgene expression in AAV3B-DE5 transduced human and non-human primate primary hepatocytes, as compared to AAV8. In contrast, AAV3B-DE5 was unable to transduce murine primary hepatocytes, whereas AAV8 displayed high transduction of murine hepatocytes as determined by GFP mRNA transcript levels using real time RT-PCR (FIG. 19C).

In Vitro Characterization: Determination of NAb Titers

Since pre-existing humoral immunity can block vector transduction efficiency, two different methods were tested to assess vector capsid neutralization by pre-existing NAb from human sera.

Neutralizing Antibody Assay, Pooled Immunoglobulin

In order to test whether mutations in the AAV3B-DE5 variant affected neutralization by pre-existing anti-capsid antibodies that originate from natural infections in the human population, transduction levels by AAV3B or AAV3B-DE5 of HUH-7 cells were tested in the presence of varying concentrations of human intravenous immunoglobulin (IVIg, pooled sera from multiple samples). First, both viruses were incubated with different concentrations of IVIg, ranging from 100 µg/ml to 1000 µg/ml for 1 hr at 37° C. in a humidified $CO_2$ incubator. This virus-sera mixture was then overlaid on HUH-7 cells that had been pre-incubated with Ad5 in 96 well plate format for 1 hr at 37° C. in the incubator. The virus-sera mixture was then removed, fresh media was added, and cells were incubated for 72 hrs at 37° C. Cells were quantified after 72 hrs for mApple expression by flow cytometry.

Figure 10:
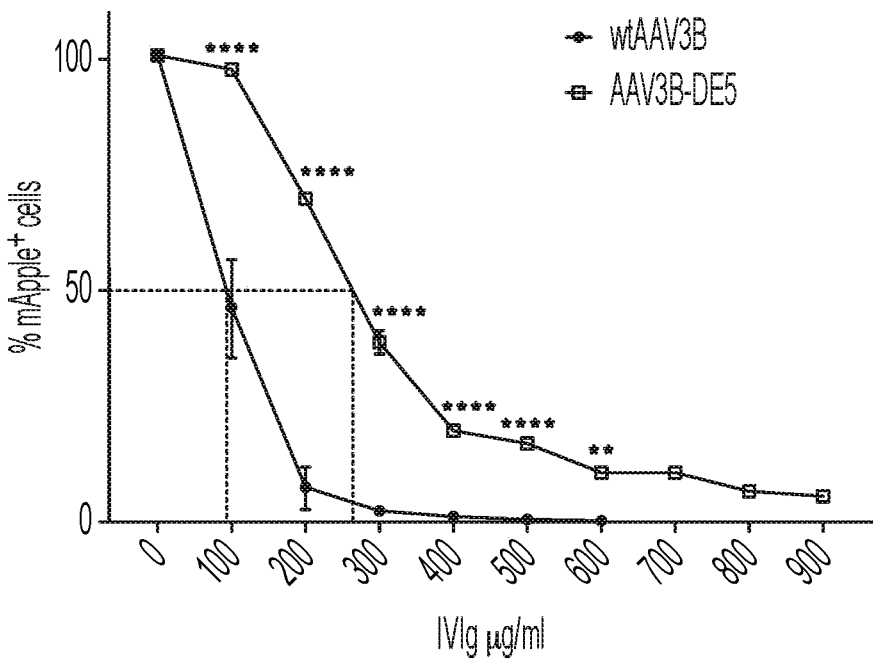
FIG. 10 is a graph showing results of an in vitro assay for neutralization of antibody against wild-type AAV3B and AAV3B-DE5. The graph shows determination of reciprocal NAb titers to wt AAV3B or AAV3B-DE5 by using increasing concentrations of pooled IVIg (100-1000 µg/mL). The IVIg concentration at which 50% mApple expression is reduced as compared to no IVIg control, is indicated with the red dotted lines. % mApple+cells are quantified by flow cytometry. Data are represented as mean±SD, with statistical significance between wt AAV3B and AAV3B-DE5 conducted by 2-way ANOVA with Sidak's multiple comparisons test. The results of the neutralization assay indicated that the AAV3B-DE5 capsid variant evaded neutralization at a concentration of intravenous immunoglobulin (IVIg) that effectively neutralized 50% transduction by the wild-type virus.

Transduction efficacy was normalized to 100% in the absence of IVIg. The concentration of IVIg at which 50% cell transduction was observed was determined to be the neutralization titer of each virus. The results of this assay indicate that the AAV3B-DE5 capsid variant evaded neutralizing antibodies at the concentration of IVIg (~200 µg/ml) that effectively neutralized 50% transduction by AAV3BWT. See FIG. 10. Thus, DE5 displayed a 2-fold increase in resistance to pooled immunoglobulin (IVIg) neutralization.

wt AAV3B with AAV3B-DE5 vectors expressing the mApple transgene were pre-incubated with serial dilutions of pooled IVIg and then used to transduce HUH-7 cell monolayers at $1\times10^4$ MOI. Percent transduced cells (mApple+) as determined by flow cytometry were normalized to AAV only controls (no IVIg). As compared to wt AAV3B, AAV3B-DE5 was significantly able to evade IVIg neutralization at all concentrations of IVIg tested (FIG. 10). Average reciprocal NAb titer for wt AAV3B was 85.1±0.6 µg/mL IVIg, while for AAV3B-DE5, it was 274.8±0.9 µg/mL IVIg, an average 3.2-fold difference in NAb titers.

Figure 20A:
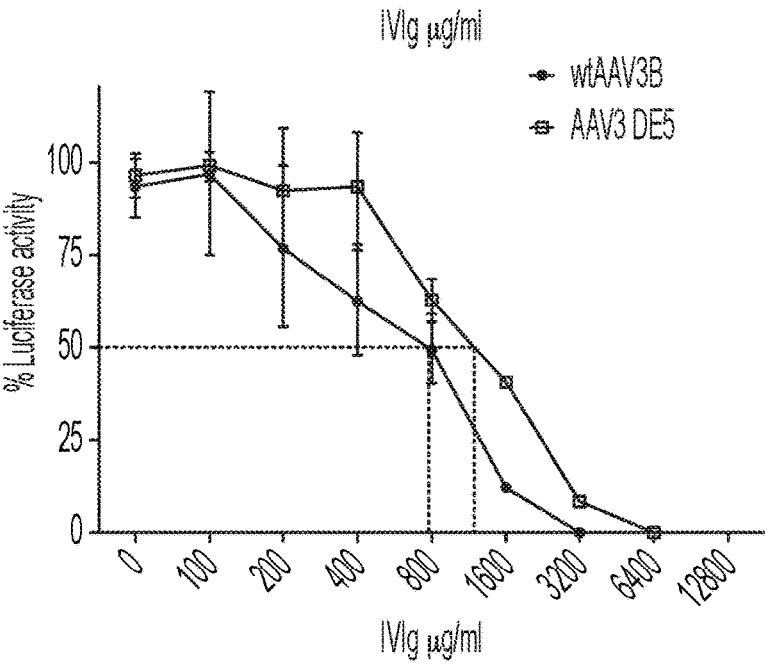
FIGS. 20A and 20B show additional in vitro assays for neutralization of transduction.
Figure 20B:
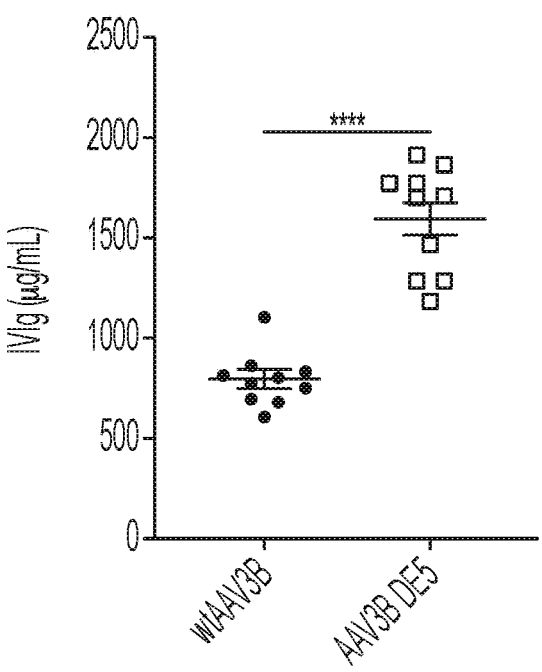

The sensitivity of anti-AAV NAb titer determination has been shown to depend on the reporter gene used in the assay. Therefore, the more sensitive luciferase reporter based neutralizing assay was used as previously described in published reports[34, 35]. $1.36\times10^5$ MOI of wt AAV3B or AAV3B-DE5 expressing the luciferase reporter transgene was pre-incubated with serial dilutions of pooled IVIg and overlaid on HUH-7 cell monolayers as described in methods. As observed in FIG. 10, substantial evasion was confirmed by AAV3-DE5 to anti-AAV NAb from pooled IVIg, as detailed in a representative figure (FIG. 20A). Average reciprocal NAb titers combined from 10 independent experiments was 793.3±42.7 µg/mL IVIg for wt AAV3B, and 1595±84 µg/mL IVIg for AAV3B-DE5, a 2-fold difference (FIG. 20B). The higher NAb titers observed in the luciferase neutralizing assay could be attributed to the higher MOI of AAV used and the increased sensitivity of detection.

Human Serum Samples

Figure 21A:
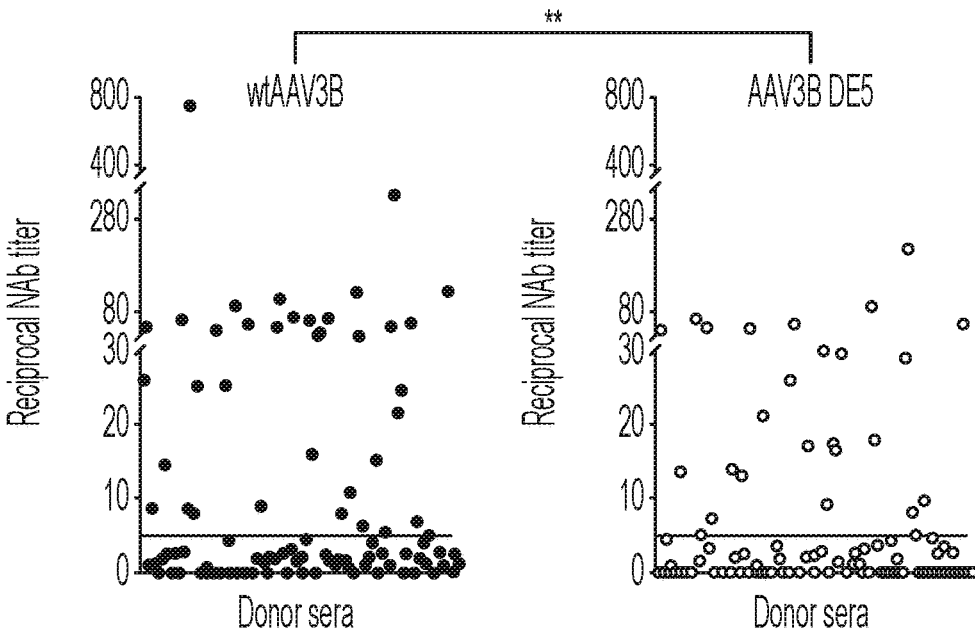
FIGS. 21A-21C show neutralization of individual serum samples.
Figure 21B:
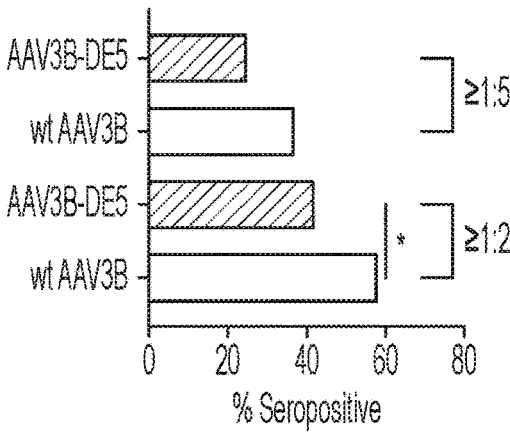

In another set of experiments, seroprevalence of wt AAV3B or AAV3B-DE5 were compared in individual serum samples using the luciferase based neutralizing assay. Serum from 100 healthy donors were tested for NAb titers to wt AAV3B or AAV3B-DE5. Using 1:5 serum dilution as a cut-off, pre-existing NAb to wt AAV3B was 37% and to AAV3B-DE5, 25%, an ~1.5 fold lower NAb incidence (p=0.033, FIG. 21A). Since even very low titers of AAV NAbs have been shown to block in vivo transduction in clinical trials and animal studies14, 15, frequencies of NAb titers >1:2 were looked at (FIG. 21B). On lowering the detection threshold to ≥1:2, 58% and 42% of healthy donor sera had pre-existing NAb to wt AAV3B and AAV3B-DE5 respectively.

Figure 21C:
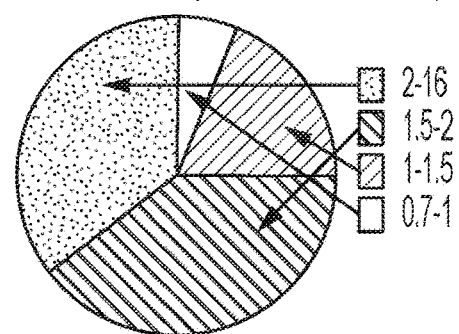

Of the serum samples that were seropositive for both wt AAV3B and AAV3B-DE5, 33% (16 samples) had 2- to 6-fold higher NAb titers for wt AAV3B as compared to AAV3B-DE5, while one individual sample had a 15-fold higher titer for wt AAV3B (FIG. 21C). The majority of serum samples (40%, 19 samples) had 1.5- to 2-fold higher NAb titers for wt AAV3B. 19% had 1- to 1.5 higher NAb titers for wt AAV3B compared to AAV3B-DE5, while only 3 samples (6.3%) has 0.7- to 1-fold difference. Importantly, none of the serum samples had 2-fold or higher titers for AAV3B-DE5 as compared to wt AAV3B. This indicates that original reactivities were maintained or significantly reduced in the AAV3B-DE5 variant, and that new antigenic determinants were not selected for or created.

Serotype Comparison in Human Liver Chimeric Mice.

Figure 22A:
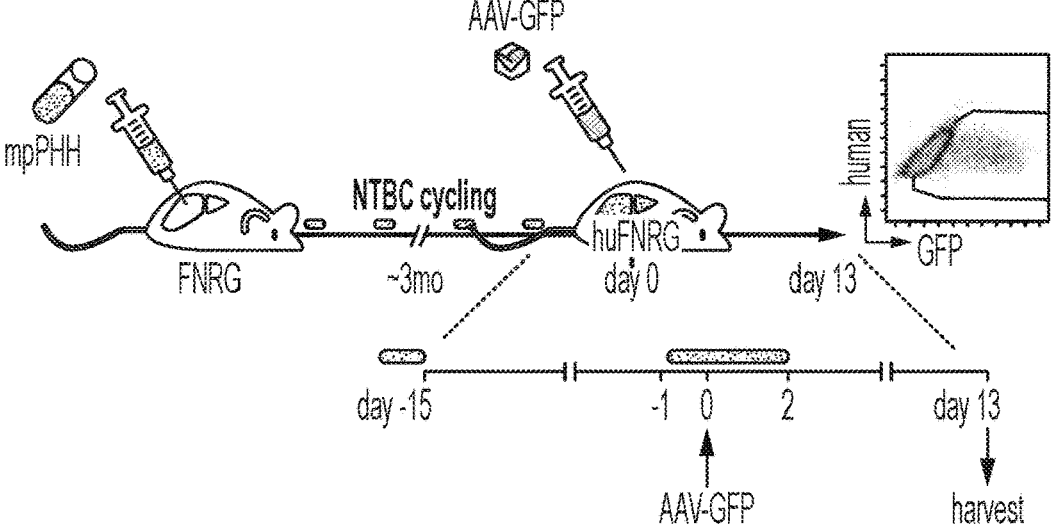
FIGS. 22A-22D show in vivo transduction efficiency in human liver chimeric mice.
Figure 22B:
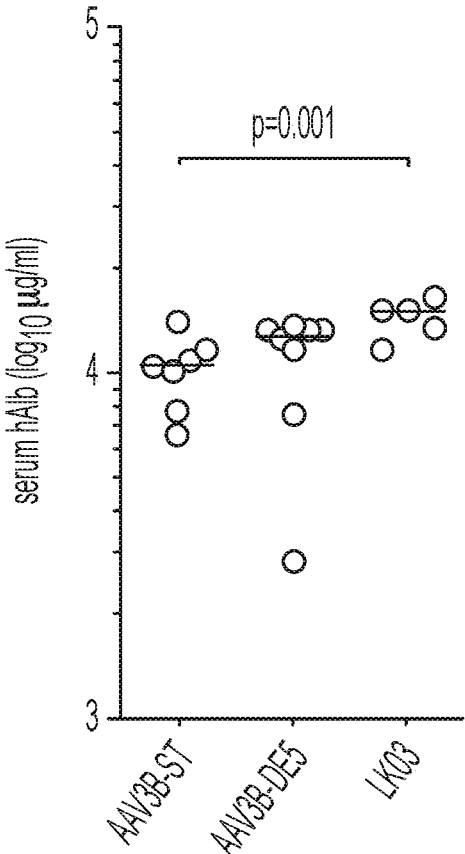

Liver chimeric mouse models allow for in vivo studies of primary human hepatocytes[36]. Given the stark species differences in AAV hepatocyte transduction, these human liver chimera models are increasingly applied to test engineered AAV serotypes[23, 33, 37]. Here, (Fah)$^{-/-}$ NOD Rag1$^{-/-}$ Il2rg$^{null}$ (FNRG) that were humanized with mouse-passaged primary human hepatocytes (huFNRG mice)[38, 39] were used. After transplantation, mice were cycled off the protective drug 2-(2-nitro-4-trifluoromethylbenzoyl)-1,3-cyclohexane-dione (NTBC or nitisinone) for approximately 3 months to expand the human graft. Chimerism was determined by human albumin (hAlb) quantification in mouse serum, which correlates well with humanization[40-42]. Once mice had reached peak hAlb levels they were challenged one day after restarting NTBC as illustrated by the experimental schematic (FIG. 22A). The plateau hAlb levels showed that most animals were >80% humanized (FIG. 22B). In order to test transduction of AAV3B-DE5 in vivo, three cohorts of huFNRG mice were created. The performance of the AAV3B-DE5 variant in transducing human hepatocytes with 2 other AAV vectors were compared, which have earlier been shown to transduce human hepatocytes with high efficiency.

Figures 22C, 22D:
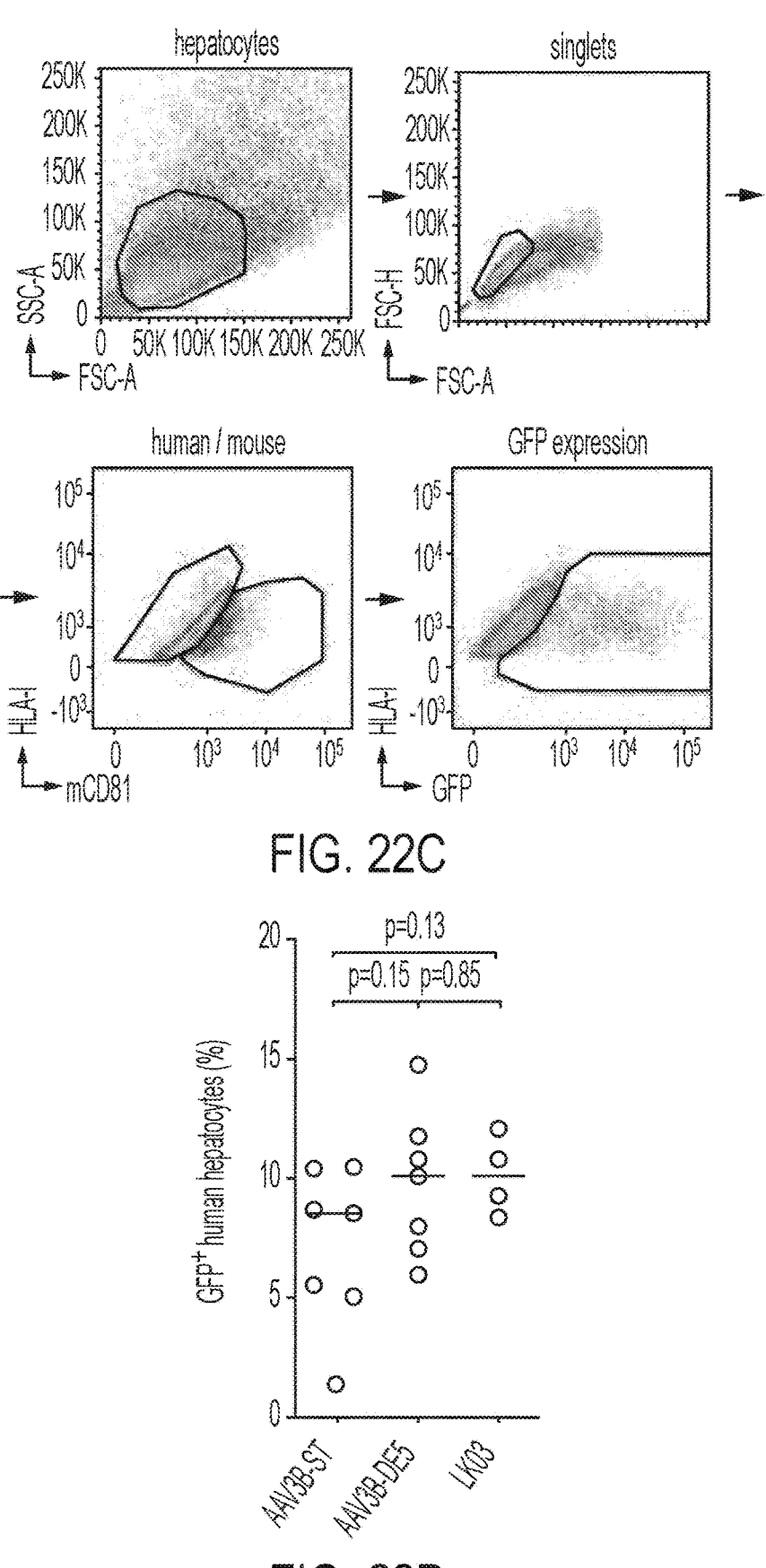

Animals were intravenously administered with 2×10$^{11}$ vg of either AAV3B-ST, LK03, or AAV3B-DE5, expressing the GFP transgene. Thirteen days later, hepatocytes were isolated from chimeric livers[38], and stained for human HLA-I. Mouse CD81 antibody was used to exclude non-human hepatocytes. After sequential gating (FIG. 22C) the GFP+ fraction of human hepatocytes was quantified. AAV3B-DE5 transduced minimally higher fractions of human hepatocytes than AAV3B-ST, although it did not reach statistical significance. The percentage of GFP+ transduced human hepatocytes was comparable to the previously reported bioengineered LK03 capsid (FIG. 22D). These data indicate that AAV3B-DE5 can transduce human hepatocytes in chimeric livers at efficiencies similar to LK03 and possibly slightly better than AAV3B-3ST. Transduction efficiency of mouse hepatocytes cannot be assessed in this highly humanized model because of low numbers, as well as the unhealthy condition of these cells due to NTBC withdrawal[39].

Discussion

The wide and continuous success of AAV as a therapeutic gene delivery vehicle has led to the quest for vectors with improved transduction efficiencies, higher tissue tropism, and lower immunogenicity. These properties are largely dependent on the viral capsid and differ broadly between AAV serotypes. Hepatic gene therapy via systemic AAV administration is an advantageous delivery strategy for long lived and sustained correction of genetic disorders such as hemophilia, Wilson's disease, lysosomal storage disorders or Crigler-Najjar syndrome, among others45. Identifying an optimal viral capsid with strong liver tropism for efficient transduction of human hepatocytes has thus been under active investigation.

Methodologies for generating novel AAVs specific for a particular application include generating combinatorial capsid libraries of a high complexity, which is constrained by sequence bias or limited diversity. A rational approach of introducing deliberate mutations into amino acid residues based on the understanding of the capsid structure also faces limits as in many cases, favorable mutations cannot be combined to produce additive effects. In this current study, a naturally existing serotype was used to generate a library, combining rational mutagenesis and directed evolution to enable us to select a variant specific to the intended application. A common challenge during library generation is contamination with the parental sequence, due to incomplete removal of template DNA after PCR steps. Such contamination can, depending on its extent, seriously limit the library usefulness by reducing its diversity. Here, parental (wt AAV3B) contamination was limited to 0.69%, which is an acceptable level. On the other hand, the parental sequence can be advantageously used as a control to validate library design, by comparing enrichment of competing variants during selection. Indeed, in the experiment, the frequency of wt AAV3B decreased to 0.49% after the first round of selection, and was undetectable in subsequent rounds, confirming that the library contained improved variants compared to wt AAV3B.

A recent study suggests that library-selected capsids such as LK03 can be further improved by additional site-directed mutagenesis47. Therefore, it is likely that the newly generated capsid with high tropism for hepatocytes can still be further improved. Earlier studies found that elimination of certain tyrosine residues on the surface of AAV2 capsid could improve transduction and reduce MHC I presentation of capsid antigen. The rationale for this approach was that the AAV capsid is phosphorylated by tyrosine kinases following cellular entry, which targets the capsid for ubiquitination and proteasomal degradation[25, 48-51]. Elimination of phosphorylation sites therefore enhances transfer to the nucleus and reduces presentation of peptides derived from proteasomal degradation, therefore reducing the likelihood of being targeted by capsid-specific CD8+ T cells[9, 50, 52, 53]. When attempting to optimize the AAV3B capsid, elimination of a serine and a threonine site (S663V+T492V mutations) was found more efficacious[33, 43, 44] for transduction of human and non-human primate hepatocytes. Here, T492 positions were diversified to include either of the following positions: T/I/A/V, while leaving S663 as in the wt AAV3B. Curiously, the selected AAV3B-DE5 had a T4921 mutation, which might have achieved the same purpose as T492V substitution. This position, as well as S663, and remaining antibodies-targeted capsid surface wt residues leave significant room for additional rational engineering of the derived AAV3B-DE5 variant to improve its efficiency and stealth.

The lack of standardized methods to measure vector and neutralizing antibody titers, and variability in testing have made it difficult to predict the lowest Nab titer that can preclude AAV delivery. Using the luciferase based neutralizing antibody detection assay, and a cut off of 1:5, the seroprevalence to wt AAV3B in the cohort of 100 individual serum samples was 37%. This was very similar to the 35% previously reported for a UK patient population[54] and 36% for a North American population[55] respectively. In a separate study, a similar number of North American patient samples were analyzed and a seroprevalence to AAV3B of 45% was found (I. Zolotukhin, unpublished data). While studies indicate better evasion of pre-existing NAb by AAV3B-DE5 from healthy donors in the 100 serum samples tested, it is important to note that in the 48 samples that were seropositive for both wt AAV3B and AAV3B-DE5, ~94% had NAb titers to wt AAV3B that was up to 15-fold higher than for the AAV3B-DE5 variant. In contrast, none of the samples had a titer against AAV3B-DE5 that was even 2-fold higher than for AAV3. Therefore, it appears that no new set of antigenic epitopes were generated by the engineered variant, as patient samples reacted either similarly or less compared to wt AAV3B.

In conclusion, it was found that molecular evolution using the combinatorial library platform accomplished at the same time the generation of a viral capsid with high tropism for the desired cell type and reduced neutralization that results from pre-existing immunity to AAV in the human population. This was accomplished without inclusion of human serum or immunoglobulin in the selection process but rather resulted from the more extensive changes in amino acid sequence as compared to site-directed mutagenesis approaches. Nonetheless, rational single amino acid changes can be combined with a library selection approach to achieve superior results.

Materials and Methods

Library Design

The guiding principle behind the library's design was to modify only the VRs while keeping the backbone sequence unchanged. Following the alignment of 150 AAV naturally occurring variants, candidate positions for mutagenesis were selected from VR-I, VR-IV, VR-V, VR-VI, VR-VII, and diversified. The AAV3B capsid gene fragments incorporating all nucleotide substitutions were assembled from synthetic oligonucleotides and inserted into a plasmid vector containing the AAV3B genome from which the corresponding wt sequence had been removed. The backbone plasmid vector for the library's design and construction incorporated all AAV3B sequences necessary for replication and packaging, including AAV3 ITRs, Rep, and Cap.

Three structurally compatible sub-libraries as described in the results section were constructed using synthetic oligonucleotides by PCR and isothermal DNA assembly, packaged, and purified separately. Next, using viral DNAs as PCR templates, the VRs from the sub-libraries A, B, and C were amplified and combined in one ABC library incorporating diversified I, IV, V, VI, and VII loops. Finally, the ABC library was packaged large scale, and amplicons generated from both the plasmid and viral libraries were subjected to Illumina sequencing.

Spheroid Generation and In Vitro Selection

Spheroid cultures were generated by culturing human hepatocellular carcinoma (HUH7) single cells in 6-well ultra-low attachment plates (Corning Inc. Corning, NY). Cells were cultured in DMEM/F12K media supplemented with epidermal growth factor (EGF, 20 ng/mL), fibroblast growth factor (FGF, 10 ng/mL), B27 (1×) (Gibco, Gaithersburg, MD). Discrete spheroids were observed within 5-7 days. In order to pre-determine MOI, cells were seeded on day 0 at 0.5 million cells/mL, dissociated on day 7, counted and viability determined (Cellometer Auto T4, Nexcelom Bioscience, Lawrence, MA). On day 7, spheres were centrifuged at 300 g for 5 min and resuspended in 1 mL of DMEM/F12K medium without FBS. Spheres were first incubated with Ad5 helper virus at an MOI that had been previously determined to have 50% cytopathic effect (CPE). Incubation was carried out for 1 hr at 37° C. in a humidified $CO_2$ incubator with intermittent manual shaking. Spheres were then centrifuged in 30 mL of medium in order to remove unbound Ad5 virus, resuspended in 1 mL of DMEM/F12K medium and incubated initially with 1 MOI of the recombinant AAV3B library for 1 h at 37° C. in a humidified $CO_2$ incubator. Spheres were then extensively washed by centrifugation in 30 mL of medium in order to remove unbound virus and incubated for 72h. This was passage 1 (P-1) of the recombinant AAV3B library.

For subsequent passages (5 total passages), P-1 cells were subjected to 3 quick freeze-thaw steps. Clarified supernatant from P-1 was then used to infect P-2 of HUH7 spheres, this time at an MOI of 0.01, in order to prevent genome-capsid combinations from occurring. 5 selection passages (P-1 to P-5) were thus carried out and subjected to NGS and analysis.

In Vitro Transduction Efficiency wt AAV3B and AAV3B-DE5 non replicating vectors were packaged with the FLuc and mApple double reporter transgene plasmid pTR-UF50-BC, under control of the CBA promoter, flanked by AAV2 ITRs. A furin recognition site and self-cleaving 2-A peptide sequence was cloned downstream of the FLuc gene, and upstream of the mApple gene. Transduction efficiency of wt AAV3B and AAV3B-DE5 in human hepatocyte HUH-7 cells was compared using $3\times10^4$, $6\times10^4$, $1\times10^5$, $2.5\times10^5$, $5\times10^5$, $1\times10^6$ and $2\times10^6$ MOI respectively. Cells were counted and seeded into 96 well plates overnight and the adherent monolayer was incubated with the indicated MOIs of wt AAV3B or AAV3B-DE5 for 1 h at 37° C. Virus was removed by inverting plates and cells in supplemented media were incubated for 12-72 h at 37° C. For FLuc estimation, cells were treated as above and quantification of luciferase expression was carried out using the Bright-G10™ Luciferase Assay System (Promega, Madison, WI) and measured on an ELISA reader with luminescence detection capacity (Synergy HTX, Biotek, Winooski, VT). The same transduction procedure was carried out for human hepatocyte HUH-7, and HEPG2 spheroids with incubation in individual 15 mL conical tubes, following which cells were resuspended in spheroid media and cultured in 48 well ultra-low attachment plates. After 72h, cells were trypsinized and frequencies of mApple+cells as well as MFI's were quantified by flow cytometry (LSR Fortessa, BD Biosciences, San Jose, CA) and analyzed on the FCS Express 7 software.

Real Time PCR

Genomic DNA was isolated from AAV transduced HUH-7 cells at indicated time-points following either wt AAV3B or AAV3B-DE5 transduction, using the genomic DNA isolation kit (Qiagen, Germantown, MD) according to manufacturer's instructions. 200ng of input genomic DNA was used to quantitate AAV vector genome copy numbers using AAV2 ITR specific primers56, and a standard curve generated from serial dilutions of an AAV5 standard of known concentration. PCR reaction was performed using the 2X SYBR green supermix (Biorad, Hercules, CA), using the following cycling conditions: 50° C. for 2 min, 95° C. for 10 min, 40 cycles at 95° C. for 15 s, 60° C. for 15 s, 72° C. for 30 s, using a CFX96 touch real time PCR detection system (Biorad, Hercules, CA). AAV genome copies were normalized to cell number (Countess II, Thermo Fisher) and number of transduced cells by running flow cytometry in parallel to quantify mApple+ cells, to derive AAV genome copy/cell.

RNA Extraction and Gene Expression Analysis

Primary human hepatocytes, primary non-human primate hepatocytes (*Macaca fascicularies*), and primary mouse hepatocytes were purchased from Innoprot (Bizkaia, Spain). Cells were seeded in MIL130 or MIL600 media with ADD221 or ADD222 additives on PLA137 collagen coated plates (Biopredic international, Saint Grégoire, France). Cells were transduced after 24h with AAV3B-DE5-GFP or AAV8-GFP at 3 different MOIs ($10^4$, $3 \times 10^4$, $10^5$ vg/cell) in duplicates. Cells were harvested at 96 hours post-transduction and RNA extracted (Maxwell RSC simply RNA, Promega, Madison, WI) for quantitative RT PCR analysis of GFP mRNA transcript levels. Extracted RNA was pre-treated with Turbo DNA Free (Ambion Inc, Austin, TX) and retro-transcribed into complementary DNA (cDNA) using M-MLV reverse-transcriptase (Invitrogen, Carlsbad, CA). Copies of GFP in cDNA were analyzed by qPCR using GoTaq® qPCR Mastermix (Promega, Madison, WI) in a CFX96 Real-Time Detection System (BioRad, Hercules, CA). eGFP expression was analyzed using the following primers: 5'-ATGGTCAGCAAGGGCGAGG-3' and 5'-TTGCCGGTGGTGCAGATGAA-3'. GFP expression levels were normalized to human, non-human primate and mouse GAPDH respectively.

Mice

FNRG female mice were used at the Rockefeller University under IACUC protocol 15814.

In Vivo Transduction Efficiency

Cryopreserved pediatric human hepatocytes were purchased from Celsis Inc. (Chicago, IL). Fresh human hepatoblasts were isolated from human fetal livers procured from Advanced Bioscience Resources (ABR) as described57. Human liver cell suspensions were injected intrasplenically ($0.5$-$1 \times 10^6$ cells per mouse) under anesthesia into female FNRG mice that were generated by 13-generation backcross of the fah$^{-/-}$ allele to NOD Rag1$^{-/-}$ Il2rg$^{null}$ (NRG) animals, respectively provided by M. Grompe (Oregon Health & Science University)[58] or obtained from Jackson Laboratories. Starting on the day of transplantation, mice were cycled off the liver protective drug NTBC (Yecuris, Tualatin, OR) as described by others[37]. Human albumin levels in mouse sera were measured by enzyme-linked immunosorbent assay (Bethyl Laboratories, Montgomery, TX). In vivo transduction efficiency of 3 vectors were compared: AAV3B-DES, LK03, and an engineered vector, AAV3-ST, in which one serine and one threonine residue in the AAV3 capsid is eliminated[44]. All AAV vectors expressed the GFP transgene and were injected through the tail vein at $1 \times 10^{11}$ vector genomes per mouse. Two weeks later, human-chimeric mouse livers were removed and processed for flow cytometry and immunohistochemistry.

Human Serum Samples

Individual human serum samples were obtained from Innovative Research (Novi, MI). These were de-identified and had tested negative for HBsAg, HCV, HIV-1, HIV-2, HIV-1Ag or HIV-1 NAT, ALT, and syphilis.

In Vitro Neutralization Assay by Flow Cytometry $1 \times 10^4$ MOI of either wt AAV3b or AAV3B-DE5 vector expressing mApple reporter transgene was incubated with varying concentrations of pooled human intravenous immunoglobulin (IVIg, Privigen, CSL Behring, Bradley, IL) ranging from 100-1000 µg/mL for 1 h at 37° C. in a humidified CO2 incubator. The vector-IVIg mixture was overlaid on Ad5 pre-treated HUH-7 monolayer cells in a 96 well plate for h at 37° C. The overlay was removed, fresh media added, and cells were incubated for 72 h at 37° C. Cells were then trypsinized and frequencies of mApple+ events were quantified by flow cytometry. The reciprocal of the highest dilution of IVIG that neutralized 50% of mScarlet expression relative to control wells (transduced in the absence of IVIg) was considered to be the neutralization titer.

In Vitro Neutralization Assay by Luciferase Activity $1.36 \times 10^5$ MOI of wt AAV3B or AAV3B-DE5 expressing the FLuc and mApple double reporter transgene were incubated with serial twofold dilutions of either pooled human IVIg (Privigen, CSL Behring, Bradley, IL) or 100 individual serum samples from donors as described above. HUH-7 cells were transduced as described, except that cells were not pre-treated with Ad5 infection. After 48 h of incubation, quantification of luciferase expression was carried out using the Bright-Glo™ Luciferase Assay System (Promega, Madison, WI) and measured on an ELISA reader with luminescence detection capacity (Synergy HTX, Biotek, Winooski, VT). The neutralization titer for each sample is defined as the serum dilution at which the FLuc expression is reduced by 50% compared to the no-serum control.

Statistics

For neutralization assays, reciprocal NAb titers were extrapolated by non-linear curve fitting methods and analyzed using 4-5 parameter $IC_{50}$ tests or $4^{th}$ order polynomial curve fitting in Graphpad prism 8. For neutralization assays based on luciferase reporter expression, effect size was first measured by Z-factor test. Comparison of 2 samples was carried out using the student's t-test with Welch's correction. For non-normal distribution of data, non-parametric Mann-Whitney test was carried out. Multiple samples were compared using 2-way-ANOVA with Sidak's multiple comparisons test. Seroprevalence rates between 2 treatment groups was calculated by the Fisher's exact test using a 2×2 contingency table (Graphpad Prism).

TABLE 9

| Library NGS summary (VR-IV to VR-VII only). | | |
|---|---|---|
| Library | Plasmid | Viral |
| Filtered sequences | 1810853 | 1041321 |
| Distinct sequences (%) | 1706527 (94.24%) | 800244 (76.85%) |
| wt (%) | 381 (0.02%) | 7148 (0.69%) |
| Mutations per sequence | 23.26 | 21.56 |
| % mutant VR-IV | 99.87 | 98.52 |
| % mutant VR-V | 99.03 | 91.91 |
| % mutant VR-VI | 98.11 | 90.25 |
| % mutant VR-VII | 98.03 | 93.95 |

REFERENCES

1. Anguela, X M, and High, K A (2019). Entering the Modern Era of Gene Therapy. Annu Rev Med 70: 273-288.

2. Herzog, R W (2020). Encouraging and Unsettling Findings in Long-Term Follow-up of AAV Gene Transfer. Mol Ther 28: 341-342.

3. Perrin, G Q, Herzog, R W, and Markusic, D M (2019). Update on clinical gene therapy for hemophilia. Blood 133: 407-414.

4. Mendell, J R, Al-Zaidy, S, Shell, R, Arnold, W D, Rodino-Klapac, L R, Prior, T W, Lowes, L, Alfano, L, Berry, K, Church, K, et al. (2017). Single-Dose Gene-Replacement Therapy for Spinal Muscular Atrophy. N Engl J Med 377: 1713-1722.

5. Bennett, J, Wellman, J, Marshall, K A, McCague, S, Ashtari, M, DiStefano-Pappas, J, Elci, O U, Chung, D C, Sun, J, Wright, J F, et al. (2016). Safety and durability of effect of contralateral-eye administration of AAV2 gene therapy in patients with childhood-onset blindness caused by RPE65 mutations: a follow-on phase 1 trial. Lancet 388: 661-672.

6. Samulski, R J, and Muzyczka, N (2014). AAV-Mediated Gene Therapy for Research and Therapeutic Purposes. Annu Rev Virol 1: 427-451.

7. Nathwani, A C, Gray, J T, McIntosh, J, Ng, C Y, Zhou, J, Spence, Y, Cochrane, M, Gray, E, Tuddenham, E G, and Davidoff, A M (2007). Safe and efficient transduction of the liver after peripheral vein infusion of self-complementary AAV vector results in stable therapeutic expression of human FIX in nonhuman primates. Blood 109: 1414-1421.

8. Martino, A T, Suzuki, M, Markusic, D M, Zolotukhin, I, Ryals, R C, Moghimi, B, Ertl, H C, Muruve, D A, Lee, B, and Herzog, R W (2011). The genome of self-complementary adeno-associated viral vectors increases Toll-like receptor 9-dependent innate immune responses in the liver. Blood 117: 6459-6468.

9. Verdera, H C, Kuranda, K, and Mingozzi, F (2020). AAV Vector Immunogenicity in Humans: A Long Journey to Successful Gene Transfer. Mol Ther 28: 723-746.

10. Boutin, S, Monteilhet, V, Veron, P, Leborgne, C, Benveniste, O, Montus, M F, and Masurier, C (2010). Prevalence of serum IgG and neutralizing factors against adeno-associated virus (AAV) types 1, 2, 5, 6, 8, and 9 in the healthy population: implications for gene therapy using AAV vectors. Hum Gene Ther 21: 704-712.

11. Blacklow, N R, Hoggan, M D, Kapikian, A Z, Austin, J B, and Rowe, W P (1968). Epidemiology of adenovirus-associated virus infection in a nursery population. Am J Epidemiol 88: 368-378.

12. Calcedo, R, Vandenberghe, L H, Gao, G, Lin, J, and Wilson, J M (2009). Worldwide epidemiology of neutralizing antibodies to adeno-associated viruses. J Infect Dis 199: 381-390.

13. Aronson, S J, Veron, P, Collaud, F, Hubert, A, Delahais, V, Honnet, G, de Knegt, R J, Junge, N, Baumann, U, Di Giorgio, A, et al. (2019). Prevalence and Relevance of Pre-Existing Anti-Adeno-Associated Virus Immunity in the Context of Gene Therapy for Crigler-Najjar Syndrome. Hum Gene Ther 30: 1297-1305.

14. Manno, C S, Pierce, G F, Arruda, V R, Glader, B, Ragni, M, Rasko, J J, Ozelo, M C, Hoots, K, Blatt, P, Konkle, B, et al. (2006). Successful transduction of liver in hemophilia by AAV-Factor IX and limitations imposed by the host immune response. Nat Med 12: 342-347.

15. Jiang, H, Couto, L B, Patarroyo-White, S, Liu, T, Nagy, D, Vargas, J A, Zhou, S, Scallan, C D, Sommer, J, Vijay, S, et al. (2006). Effects of transient immunosuppression on adenoassociated, virus-mediated, liver-directed gene transfer in rhesus macaques and implications for human gene therapy. Blood 108: 3321-3328.

16. Liu, Q, Huang, W, Zhang, H, Wang, Y, Zhao, J, Song, A, Xie, H, Zhao, C, Gao, D, and Wang, Y (2014). Neutralizing antibodies against AAV2, AAV5 and AAV8 in healthy and HIV-1-infected subjects in China: implications for gene therapy using AAV vectors. Gene Ther 21: 732-738.

17. Rutledge, E A, Halbert, C L, and Russell, D W (1998). Infectious clones and vectors derived from adeno-associated virus (AAV) serotypes other than AAV type 2. J Virol 72: 309-319.

18. Srivastava, A (2016). In vivo tissue-tropism of adeno-associated viral vectors. Curr Opin Virol 21: 75-80.

19. Ertl, H C J, and High, K A (2017). Impact of AAV Capsid-Specific T-Cell Responses on Design and Outcome of Clinical Gene Transfer Trials with Recombinant Adeno-Associated Viral Vectors: An Evolving Controversy. Hum Gene Ther 28: 328-337.

20. Agbandje-McKenna, M, and Kleinschmidt, J (2011). AAV capsid structure and cell interactions. Methods Mol Biol 807: 47-92.

21. Marsic, D, Govindasamy, L, Currlin, S, Markusic, D M, Tseng, Y S, Herzog, R W, Agbandje-McKenna, M, and Zolotukhin, S (2014). Vector design Tour de Force: integrating combinatorial and rational approaches to derive novel adeno-associated virus variants. Mol Ther 22: 1900-1909.

22. Li, C, and Samulski, R J (2020). Engineering adeno-associated virus vectors for gene therapy. Nat Rev Genet 21: 255-272.

23. Lisowski, L, Dane, A P, Chu, K, Zhang, Y, Cunningham, S C, Wilson, E M, Nygaard, S, Grompe, M, Alexander, I E, and Kay, M A (2014). Selection and evaluation of clinically relevant AAV variants in a xenograft liver model. Nature 506: 382-386.

24. Paulk, N K, Pekrun, K, Zhu, E, Nygaard, S, Li, B, Xu, J, Chu, K, Leborgne, C, Dane, A P, Haft, A, et al. (2018). Bioengineered AAV Capsids with Combined High Human Liver Transduction In vivo and Unique Humoral Seroreactivity. Mol Ther 26: 289-303.

25. Zhong, L, Li, B, Mah, C S, Govindasamy, L, Agbandje-McKenna, M, Cooper, M, Herzog, R W, Zolotukhin, I, Warrington, K H, Jr., Weigel-Van Aken, K A, et al. (2008). Next generation of adeno-associated virus 2 vectors: point mutations in tyrosines lead to high-efficiency transduction at lower doses. Proc Natl Acad Sci USA 105: 7827-7832.

26. Markusic, D M, Nichols, T C, Merricks, E P, Palaschak, B, Zolotukhin, I, Marsic, D, Zolotukhin, S, Srivastava, A, and Herzog, R W (2017). Evaluation of engineered AAV capsids for hepatic factor IX gene transfer in murine and canine models. J Transl Med 15: 94.

27. Rose, J A, Maizel, J V, Jr., Inman, J K, and Shatkin, A J (1971). Structural proteins of adenovirus-associated viruses. J Virol 8: 766-770.

28. Govindasamy, L, DiMattia, M A, Gurda, B L, Halder, S, McKenna, R, Chiorini, J A, Muzyczka, N, Zolotukhin, S, and Agbandje-McKenna, M (2013). Structural insights into adeno-associated virus serotype 5. J Virol 87: 11187-11199.

29. DiMattia, M A, Nam, H J, Van Vliet, K, Mitchell, M, Bennett, A, Gurda, B L, McKenna, R, Olson, N H, Sinkovits, R S, Potter, M, et al. (2012). Structural insight into the unique properties of adeno-associated virus serotype 9. J Virol 86: 6947-6958.

30. Kapalczynska, M, Kolenda, T, Przybyla, W, Zajaczkowska, M, Teresiak, A, Filas, V, Ibbs, M, Blizniak, R, Luczewski, L, and Lamperska, K (2018). 2D and 3D cell cultures—a comparison of different types of cancer cell cultures. Arch Med Sci 14: 910-919.

31. Pekrun, K, De Alencastro, G, Luo, Q J, Liu, J, Kim, Y, Nygaard, S, Galivo, F, Zhang, F, Song, R, Tiffany, M R, et al. (2019). Using a barcoded AAV capsid library to select for clinically relevant gene therapy vectors. JCI Insight 4.

32. Grimm, D, and Zolotukhin, S (2015). E Pluribus Unum: 50 Years of Research, Millions of Viruses, and One Goal—Tailored Acceleration of AAV Evolution. Mol Ther 23: 1819-1831.

33. Vercauteren, K, Hoffman, B E, Zolotukhin, I, Keeler, G D, Xiao, J W, Basner-Tschakarjan, E, High, K A, Ertl, H C, Rice, C M, Srivastava, A, et al. (2016). Superior In vivo Transduction of Human Hepatocytes Using Engineered AAV3 Capsid. Mol Ther 24: 1042-1049.

34. Meliani, A, Leborgne, C, Triffault, S, Jeanson-Leh, L, Veron, P, and Mingozzi, F (2015). Determination of anti-adeno-associated virus vector neutralizing antibody titer with an in vitro reporter system. Hum Gene Ther Methods 26: 45-53.

35. Mingozzi, F, Chen, Y, Edmonson, S C, Zhou, S, Thurlings, R M, Tak, P P, High, K A, and Vervoordeldonk, M J (2013). Prevalence and pharmacological modulation of humoral immunity to AAV vectors in gene transfer to synovial tissue. Gene Ther 20: 417-424.

36. Grompe, M, and Strom, S (2013). Mice with human livers. Gastroenterology 145: 1209-1214.

37. Bissig-Choisat, B, Wang, L, Legras, X, Saha, P K, Chen, L, Bell, P, Pankowicz, F P, Hill, M C, Barzi, M, Leyton, C K, et al. (2015). Development and rescue of human familial hypercholesterolaemia in a xenograft mouse model. Nat Commun 6: 7339.

38. Michailidis, E, Vercauteren, K, Mancio-Silva, L, Andrus, L, Jahan, C, Ricardo-Lax, I, Zou, C, Kabbani, M, Park, P, Quirk, C, et al. (2020). Expansion, in vivo-ex vivo cycling, and genetic manipulation of primary human hepatocytes. Proc Natl Acad Sci USA 117: 1678-1688.

39. Zou, C, Vercauteren, K O A, Michailidis, E, Kabbani, M, Zoluthkin, I, Quirk, C, Chiriboga, L, Yazicioglu, M, Anguela, X M, Meuleman, P, et al. (2020). Experimental Variables that Affect Human Hepatocyte AAV Transduction in Liver Chimeric Mice. Mol Ther Methods Clin Dev 18: 189-198.

40. Vanwolleghem, T, Libbrecht, L, Hansen, B E, Desombere, I, Roskams, T, Meuleman, P, and Leroux-Roels, G (2010). Factors determining successful engraftment of hepatocytes and susceptibility to hepatitis B and C virus infection in uPA-SCID mice. J Hepatol 53: 468-476.

41. Kawahara, T, Toso, C, Douglas, D N, Nourbakhsh, M, Lewis, J T, Tyrrell, D L, Lund, G A, Churchill, T A, and Kneteman, N M (2010). Factors affecting hepatocyte isolation, engraftment, and replication in an in vivo model. Liver Transpl 16: 974-982.

42. Billerbeck, E, Mommersteeg, M C, Shlomai, A, Xiao, J W, Andrus, L, Bhatta, A, Vercauteren, K, Michailidis, E, Dorner, M, Krishnan, A, et al. (2016). Humanized mice efficiently engrafted with fetal hepatoblasts and syngeneic immune cells develop human monocytes and NK cells. J Hepatol 65: 334-343.

43. Ling, C, Wang, Y, Zhang, Y, Ejjigani, A, Yin, Z, Lu, Y, Wang, L, Wang, M, Li, J, Hu, Z, et al. (2014). Selective in vivo targeting of human liver tumors by optimized AAV3 vectors in a murine xenograft model. Hum Gene Ther 25: 1023-1034.

44. Li, S, Ling, C, Zhong, L, Li, M, Su, Q, He, R, Tang, Q, Greiner, D L, Shultz, L D, Brehm, M A, et al. (2015). Efficient and Targeted Transduction of Nonhuman Primate Liver With Systemically Delivered Optimized AAV3B Vectors. Mol Ther 23: 1867-1876.

45. Baruteau, J, Waddington, S N, Alexander, I E, and Gissen, P (2017). Gene therapy for monogenic liver diseases: clinical successes, current challenges and future prospects. J Inherit Metab Dis 40: 497-517.

46. de Alencastro, G, Pekrun, K, Valdmanis, P, Tiffany, M, Xu, J, and Kay, M A (2020). Tracking Adeno-Associated Virus Capsid Evolution by High-Throughput Sequencing. Hum Gene Ther 31: 553-564.

47. Ran, G, Chen, X, Xie, Y, Zheng, Q, Xie, J, Yu, C, Pittman, N, Qi, S, Yu, F X, Agbandje-McKenna, M, et al. (2020). Site-Directed Mutagenesis Improves the Transduction Efficiency of Capsid Library-Derived Recombinant AAV Vectors. Mol Ther Methods Clin Dev 17: 545-555.

48. Zhong, L, Li, B, Jayandharan, G, Mah, C S, Govindasamy, L, Agbandje-McKenna, M, Herzog, R W, Weigel-Van Aken, K A, Hobbs, J A, Zolotukhin, S, et al. (2008). Tyrosine-phosphorylation of AAV2 vectors and its consequences on viral intracellular trafficking and transgene expression. Virology 381: 194-202.

49. Markusic, D M, Herzog, R W, Aslanidi, G V, Hoffman, B E, Li, B, Li, M, Jayandharan, G R, Ling, C, Zolotukhin, I, Ma, W, et al. (2010). High-efficiency transduction and correction of murine hemophilia B using AAV2 vectors devoid of multiple surface-exposed tyrosines. Mol Ther 18: 2048-2056.

50. Martino, A T, Basner-Tschakarjan, E, Markusic, D M, Finn, J D, Hinderer, C, Zhou, S, Ostrov, D A, Srivastava, A, Ertl, H C, Terhorst, C, et al. (2013). Engineered AAV vector minimizes in vivo targeting of transduced hepatocytes by capsid-specific CD8+ T cells. Blood 121: 2224-2233.

51. Buning, H, and Srivastava, A (2019). Capsid Modifications for Targeting and Improving the Efficacy of AAV Vectors. Mol Ther Methods Clin Dev 12: 248-265.

52. Shirley, J L, de Jong, Y P, Terhorst, C, and Herzog, R W (2020). Immune Responses to Viral Gene Therapy Vectors. Mol Ther 28: 709-722.

53. Shirley, J L, Keeler, G D, Sherman, A, Zolotukhin, I, Markusic, D M, Hoffman, B E, Morel, L M, Wallet, M A, Terhorst, C, and Herzog, R W (2020). Type I IFN Sensing by cDCs and CD4(+) T Cell Help Are Both Requisite for Cross-Priming of AAV Capsid-Specific CD8(+) T Cells. Mol Ther 28: 758-770.

54. Perocheau, D P, Cunningham, S, Lee, J, Antinao Diaz, J, Waddington, S N, Gilmour, K, Eaglestone, S, Lisowski, L, Thrasher, A J, Alexander, I E, et al. (2019). Age-Related Seroprevalence of Antibodies Against AAV-LK03 in a UK Population Cohort. Hum Gene Ther 30: 79-87.

55. Wang, L, Bell, P, Somanathan, S, Wang, Q, He, Z, Yu, H, McMenamin, D, Goode, T, Calcedo, R, and Wilson, J M (2015). Comparative Study of Liver Gene Transfer With AAV Vectors Based on Natural and Engineered AAV Capsids. Mol Ther 23: 1877-1887.

56. Aurnhammer, C, Haase, M, Muether, N, Hausl, M, Rauschhuber, C, Huber, I, Nitschko, H, Busch, U, Sing, A, Ehrhardt, A, et al. (2012). Universal real-time PCR for the detection and quantification of adeno-associated virus serotype 2-derived inverted terminal repeat sequences. Hum Gene Ther Methods 23: 18-28.

57. Andrus, L, Marukian, S, Jones, C T, Catanese, M T, Sheahan, T P, Schoggins, J W, Barry, W T, Dustin, L B, Trehan, K, Ploss, A, et al. (2011). Expression of paramyxovirus V proteins promotes replication and spread of hepatitis C virus in cultures of primary human fetal liver cells. Hepatology 54: 1901-1912.

58. Brehm, M A, Cuthbert, A, Yang, C, Miller, D M, Dilorio, P, Laning, J, Burzenski, L, Gott, B, Foreman, O, Kavirayani, A, et al. (2010). Parameters for establishing humanized mouse models to study human immunity: analysis of human hematopoietic stem cell engraftment in three immunodeficient strains of mice bearing the IL2rgamma(null) mutation. Clin Immunol 135: 84-98.

What is claimed is:

1. A variant recombinant adeno-associated virus (rAAV) serotype 3B (AAV3B) capsid protein comprising each of the following sets of sequences and/or substitutions in the wild-type AAV3B VP1 sequence of SEQ ID NO: 1:

(a) $STX_4X_5GTTGTX_8X_9LX_{10}$ (SEQ ID NO: 7) in variable region (VR) IV wherein $X_4$ is P; $X_5$ is G; $X_8$ is N; $X_9$ is G; and $X_{10}$ is K;

(b) $X_{11}X_{12}X_{13}X_{14}NNNSNFPWTAASX_{15}$ in VR V, wherein $X_{11}$ is I or T; $X_{12}$ is A or P; $X_{13}$ is S; $X_{14}$ is D or Q; and $X_{15}$ is K or T;

(c) $KDDX_{16}X_{17}X_{18}$ in VR VI, wherein $X_{16}$ is E or D; $X_{17}$ is D; and $X_{18}$ is K or R; and (d) one of QSSNTAPTTRTVND (SEQ ID NO: 6) or QNGRDNPTFRDVQH (SEQ ID NO: 8) in VR VIII.

2. The variant of claim 1 comprising one or more of (a) STPGGTTGTNGLK (SEQ ID NO: 3) in VR IV, (b) IPSQNNNSNFPWTAASK (SEQ ID NO: 4) in VR V, (c) KDDDDR (SEQ ID NO: 9) in VR VI, and (d) QSSNTAPT-TRTVND (SEQ ID NO: 6) in VR VIII.

3. The variant of claim 1 further comprising GKQGAGRDNTEYDH (SEQ ID NO: 5) in VR VII.

4. The variant of claim 1 further comprising the substitution Q263A.

5. The variant of claim 1 further comprising one or more of the substitutions R460G, N494S, S551D, A553T, L555Y, and N557H in SEQ ID NO: 1.

6. The variant of claim 1 further comprising the substitutions R460G, N494S, S551D, A553T, L555Y, and N557H in SEQ ID NO: 1.

7. The variant of claim 1, wherein the capsid protein comprises the amino acid sequence set forth in SEQ ID NO: 2.

8. A variant recombinant AAV3B particle comprising the recombinant AAV capsid protein of claim 1.

9. The variant recombinant AAV3B particle of claim 8, further comprising a nucleic acid comprising a transgene of interest.

10. The variant recombinant AAV3B particle of claim 9, wherein the transgene is selected from F8, ATP7B, GAA and UGT1A1.

11. The variant recombinant AAV3B particle of claim 8, wherein the nucleic acid is single stranded or self-complementary.

12. A composition comprising a plurality of the variant recombinant AAV3B particle of claim 9, optionally wherein the composition further comprises a pharmaceutical carrier, optionally wherein the plurality is in an amount of between $1\times10^{11}$ vgs/ml and $2\times10^{11}$ vgs/ml, or between $1\times10^{12}$ and $4\times10^{12}$ vgs/ml.

13. A method of transducing a hepatic cell with a transgene of interest, the method comprising providing to the hepatic cell the variant recombinant AAV particle of claim 9, wherein the hepatic cell is a human hepatocyte.

14. A method of treating a disease or disorder comprising administering the variant recombinant AAV particle of claim 8, to a subject in need thereof.

15. The method of claim 14, wherein the disease or disorder is selected from Wilson's Disease, hemophilia, a lysosomal storage disorder, and Crigler-Najjar syndrome.

16. The method of claim 14, wherein the step of administering provides an about 1.5-fold, a 2-fold, a 2.5-fold, a 3-fold, a 3.2-fold, a 3.5-fold, a 4-fold, a 5-fold, a 6-fold, a 10-fold, a 12-fold or a 15-fold decrease in seroreactivity to neutralizing anti-AAV antibodies in the subject, relative to a wild-type recombinant AAV3B particle, and/or wherein the step of administering provides about a 15%, a 30%, a 50%, a 100%, a 200%, a 300%, a 400%, a 500%, a 750%, or a 1000% increase in transduction of the transgene of interest in hepatic cells in the subject, relative to a wild-type recombinant AAV3B particle.

17. The method of claim 14, wherein the step of administering provides about a 15%, a 30%, a 50%, a 100%, or more than a 100% increase in transduction of the transgene of interest in hepatic cells in the subject, relative to a recombinant AAV3-ST particle.

18. The method of claim 14, wherein the subject is a primate, optionally wherein the subject is a human.

19. The method of claim 14 further comprising re-administering the recombinant AAV particle.

20. A method comprising administering the variant recombinant AAV particle of claim 8, to a subject in need thereof whom has previously been administered the recombinant AAV particle.

* * * * *